United States Patent
Griebenow et al.

(10) Patent No.: US 11,130,768 B2
(45) Date of Patent: Sep. 28, 2021

(54) BICYCLIC PYRAZOLE DERIVATIVES

(71) Applicant: Bayer Animal Health GMBH, Leverkusen (DE)

(72) Inventors: Nils Griebenow, Dormagen (DE); Wei Zhuang, Monheim (DE); Daniel Kulke, Leverkusen (DE); Adeline Köhler, Langenfeld (DE); Thomas Ilg, Monheim (DE); Claudia Welz, Düsseldorf (DE); Hans-Georg Schwarz, Dorsten (DE); Ulrich Görgens, Ratingen (DE); Walter Hübsch, Wuppertal (DE); Johannes Köbberling, Neuss (DE)

(73) Assignee: Bayer Animal Health GmbH, Monheim am Rhein (DE)

( * ) Notice: Subject to any disclaimer, the term of this patent is extended or adjusted under 35 U.S.C. 154(b) by 0 days.

(21) Appl. No.: 16/608,744

(22) PCT Filed: Apr. 23, 2018

(86) PCT No.: PCT/EP2018/060313
§ 371 (c)(1),
(2) Date: Oct. 25, 2019

(87) PCT Pub. No.: WO2018/197401
PCT Pub. Date: Nov. 1, 2018

(65) Prior Publication Data
US 2020/0190111 A1    Jun. 18, 2020

(30) Foreign Application Priority Data

Apr. 27, 2017   (EP) ..................... 17168558

(51) Int. Cl.
C07D 513/04    (2006.01)
A61P 33/10    (2006.01)

(52) U.S. Cl.
CPC ............ *C07D 513/04* (2013.01); *A61P 33/10* (2018.01)

(58) Field of Classification Search
CPC ...................... C07D 513/00; C07D 513/04
See application file for complete search history.

(56) References Cited

U.S. PATENT DOCUMENTS

| | | | |
|---|---|---|---|
| 7,662,826 B2 | 2/2010 | Seno |
| 7,872,036 B2 | 1/2011 | Toriyabe |
| 8,536,340 B2 | 9/2013 | Iwasa |
| 8,697,867 B2 | 4/2014 | Hamamoto |
| 8,729,264 B2 | 5/2014 | Yamamoto |
| 8,946,234 B2 | 2/2015 | Maue |
| 9,717,242 B2 | 8/2017 | Kagabu |
| 2011/0086882 A1 | 4/2011 | Shin |
| 2014/0213448 A1 | 7/2014 | Buysse |
| 2014/0275503 A1 | 9/2014 | Giampietro |

FOREIGN PATENT DOCUMENTS

| | | |
|---|---|---|
| CN | 101715774 A | 6/2010 |
| CN | 101337937 B | 12/2010 |
| CN | 102391261 A | 3/2012 |
| CN | 101337940 B | 5/2012 |
| CN | 103265527 B | 8/2014 |
| CN | 103109816 B | 9/2014 |
| CN | 103232431 B | 11/2014 |
| CN | 103524422 B | 5/2015 |
| EP | 1918291 A1 | 5/2008 |
| EP | 2647626 A1 | 10/2013 |
| JP | 2010018586 A | 1/2010 |
| JP | 5034880 B2 | 7/2012 |
| WO | WO2001016138 A1 | 3/2001 |
| WO | WO2003091256 A1 | 11/2003 |
| WO | WO2003106457 A1 | 12/2003 |
| WO | WO2004099160 A1 | 11/2004 |
| WO | WO2006003494 A2 | 1/2006 |
| WO | WO2006043635 A1 | 4/2006 |

(Continued)

OTHER PUBLICATIONS

Agrawal, V.K. et al. (1985). "Combination Therapy in the Treatment of Helminth Diseases," Medicinal Research Reviews, 5(3)333-369.
Alper, P. et al. (2014). "Discovery of structurally novel, potent and orally efficacious GPR119 agonists," Bioorganic & Medicinal Chemistry Letters, 24:2383-2387.
Berge et al. (1977). "Pharmaceutical Salts," J. Pharm. Sci. 66(1):1-19.
Bindi, S. et al. (2010). "Thieno[3,2-c]pyrazoles: A novel class of Aurora inhibitors with favorable antitumor activity," Bioorganic & Medicinal Chemistry, 18:7113-7120.
Blad, C.C. et al. (2012). "Novel 3,6,7-Substituted Pyrazolopyrimidines as Positive Allosteric Modulators for the Hydroxycarboxylic Acid Receptor 2 (GPR109A)," Journal of Medicinal Chemistry, 55: 3563-3567.
Cross et al. (1976). "International Union of Pure and Applied Chemistry: Organic Chemistry Division Commission on Nomenclature of Organic Chemistry" Pure & Appl. Chem. 45:11-30.

(Continued)

*Primary Examiner* — Valerie Rodriguez-Garcia

(57) ABSTRACT

The present invention covers bicyclic pyrazole compounds of general formula (I): in which G, A, $R^1$, $R^2$, $R^3$, and Q are as defined herein, methods of preparing said compounds, intermediate compounds useful for preparing said compounds, pharmaceutical compositions and combinations comprising said compounds and the use of said compounds for manufacturing pharmaceutical compositions for the treatment, control and/or prevention of diseases, in particular of helminth infections, as a sole agent or in combination with other active ingredients.

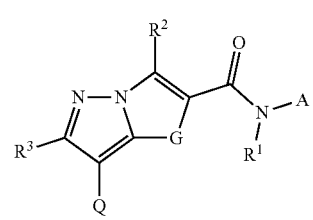

(I)

13 Claims, No Drawings

(56) References Cited

FOREIGN PATENT DOCUMENTS

| | | |
|---|---|---|
| WO | WO2007040280 A1 | 4/2007 |
| WO | WO2007040282 A1 | 4/2007 |
| WO | WO2009041663 A1 | 4/2009 |
| WO | WO2010051926 A2 | 5/2010 |
| WO | WO2010052161 A2 | 5/2010 |
| WO | WO2011085575 A1 | 7/2011 |
| WO | WO2012029672 A1 | 3/2012 |
| WO | WO2012034403 A1 | 3/2012 |
| WO | WO2012112363 A1 | 8/2012 |
| WO | WO2013050317 A1 | 4/2013 |
| WO | WO2013144213 A1 | 10/2013 |
| WO | WO2013162715 A2 | 10/2013 |
| WO | WO2013162716 A2 | 10/2013 |
| WO | WO2015058021 A1 | 4/2015 |
| WO | WO2015058028 A1 | 4/2015 |
| WO | WO2017178416 A1 | 10/2017 |

OTHER PUBLICATIONS

FCH Group. (Apr. 20, 2017). Chemical Catalogue, Registry No. 2092685-77-1, Pyrazolo[5,1-b]thiazole-2carboxylic acid, 7-bromo-6methyl-3-(1-methylethly), created Apr. 20, 2017, 1 page.

Greene, T. et al. (1999) "Protective Groups in Organic Synthesis," 3rd edition,John Wiley & Sons, Inc.

Gregg, B.T. et al. (2007). "Pyrazolo[1,5-a]pyrimidines. Identification of the Privileged Structure and Combinatorial Synthesis of 3-(Hetero)arylpyrazolo[1,5-a]pyrimidine-6-carboxamides," J. Comb. Chem. 9:507-512.

Holden-Dye, L. et al. (2014). "Anthelmintic drugs and nematicides: studies in Caenorhabditis elegans," Wormbook, ed. The C. elegans Research Community.

Maltais, F. et al. (2009). "In Vitro and In Vivo Isotope Effects with Hepatitis C Protease Inhibitors: Enhanced Plasma Exposure of Deuterated Telaprevir versus Telaprevir in Rats," J. Med. Chem.; 52(24):7993-8001.

Mehlhom et al. (2016). Encyclpaedic Reference of Parasitology 4th edition, Springer-Verlag, Berlin Heidelberg, (ISBN 978-3-662-43978-4).

Mutlib, A.E. et al. (2000). "The Species-Dependent Metabolism of Efavirenz Produces a Nephrotoxic Glutathione Conjugate in Rats," Toxicology and Applied Pharmacology, 169:102-113.

Perrin, C. et al. (2005). "Stereochemistry of β-Deuterium Isotope Effects on Amine Basicity," J. Am. Chem. Soc.; 127 (26):9641-9647.

Perrin, C. et al. (2007). "Secondary Deuterium Isotope Effects on the Acidity of Carboxylic Acids and Phenols," J. Am. Chem. Soc.; 129(14):4490-4497.

Rosman, K. et al. (1998). "Isotopic Compositions of the Elements 1997," Pure & Appl. Chem., 70(1):217-235.

Schneider, F. et al. (2006). Enhanced Plasma Concentration by Selective Deuteration of Rofecoxib in Rats, Arzneim.-Forsch./Drug Res.; 56(4):295-300.

Sharma, A. et al. (2013). "Nevirapine Bioactivation and Covalent Binding in the Skin," Chem. Res. Toxicol.; 26:410-421.

Shen, H.C. et al. (2008). "Discovery of pyrazolopyrimidines as the first class of allosteric agonists for the high affinity nicotinic acid receptor GPR109A," Bioorganic & Medicinal Chemistry Letters 18:4948-4951.

Tayar, N. et al. (1984) "The lipophilicity of deuterium atoms. A comparison of shake-flask and HPLC methods," Int J Pharm; 19(3), 271-281.

The Pesticide Manual 16th Ed., British Crop Protection Council 2012.

Wenthur, C. et al. (2013). "Discovery of (R)-(2-Fluoro-4-((-4-methoxyphenyl)ethynyl)phenyl) (3-Hydroxypiperidin-1-yl) methanone (ML337), An mGlu3 Selective and CNS Penetrant Negative Allosteric Modulator (NAM)," J. Med. Chem.; 56:5208-5212.

Wood, A. (2019). "Compendium of Pesticide Common Names," located at http://www.alanwood.net/pesticides/, last visited on Sep. 20, 2019, 2 pages.

BICYCLIC PYRAZOLE DERIVATIVES

CROSS REFERENCE TO RELATED APPLICATIONS

This application is a national stage application under 35 U.S.C. § 371 of International Application No. PCT/EP2018/060313, filed internationally on Apr. 23, 2018, which claims the benefit of European Application No. 17168558.9, filed Apr. 27, 2017.

The present invention covers new bicyclic pyrazole derivatives of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the control, treatment and/or prevention of diseases, in particular for the control, treatment and/or prevention of infections with helminths, more particularly of infections with gastro-intestinal and extra-intestinal nematodes, in animals and humans, formulations containing such compounds and methods for the control, treatment and/or prevention of infections with helminths, more particularly of infections with gastro-intestinal and extra-intestinal nematodes, in animals and humans as a sole agent or in combination with other active ingredients.

BACKGROUND

The occurrence of resistances against all commercial anthelmintics seems to be a growing problem in the area of veterinary medicine. The extensive utilisation of anthelmintics to manage the control of nematodes resulted in significant selection of highly resistant worm populations. Therefore, the spread of resistance against all anthelmintic drug classes threatens effective worm control in cattle, goats, sheep and horses. Furthermore, successful prevention of heartworm disease in dogs, which currently solely relies on the utilisation of macrocyclic lactones, is in danger as loss of efficacy for multiple macrocyclic lactones has been described for some regions of the United States of America—especially in those areas where the heartworm challenge for infection is high. Finally, experimental infection studies with *Dirofilaria immitis* larvae from suspected loss of efficacy field cases in the Lower Mississippi Delta provided in vivo confirmation of the existence of macrocyclic lactone resistance.

Although resistance of human helminths against anthelmintics seems currently to be rare, the spread of anthelmintic resistance in the veterinary field as mentioned before needs to be considered in the treatment of human helminthosis as well. Persistent underdosed treatments against filariosis may lead to highly resistant genotypes and resistances have already been described for certain anthelmintics (e.g. praziquantel, benzimidazole and niclosamide).

Therefore, resistance-breaking anthelmintics with new molecular modes of action are urgently required.

It is an object of the present invention to provide compounds which can be used as anthelmintics in the medical, especially veterinary, field with a satisfactory or improved anthelmintic activity against a broad spectrum of helminths, particularly at relatively low dosages, for the control, treatment and/or prevention of infections with helminths in animals and humans, preferably without any adverse toxic effects to the treated organism.

Certain pyrazolopyrimidine carboxamides are related to their activity increasing the efficacy of the endogenous ligand 3-hydroxybutyrateas as described in Journal of Medicinal Chemistry, 55, (7), 3563-3567. Other pyrazolopyrimidine carboxamides are described as allosteric agonists for the high affinity nicotinic acid receptor GPR109A as in Bioorganic & Medicinal Chemistry Letters, 18, (18), 4948-4951. Furthermore, pyrazolopyrimidine carboxamides are known as protein kinase modulators (EP1918291), as active ingredients for treatment or prevention of skin diseases (WO 2009041663) or as NAD(P)H oxidase inhibitors (WO 2003091256). A certain method for a library synthesis process of said compounds is described in Journal of Combinatorial Chemistry, 9, (3), 507-512. Sulfonylphenylpyrazole compounds are also known as COX-2 inhibitors (WO 2001/16138). Further imidazopyrazole coupler for the use in image formation methods in silver halide color photographic materials are known (JP05034880A).

However, the state of the art does not describe the new bicyclic pyrazole derivatives of general formula (I) of the present invention as described and defined herein.

It has now been found, and this constitutes the basis of the present invention, that the compounds of the present invention have surprising and advantageous properties.

In particular, the compounds of the present invention have surprisingly been found to effectively interact with Slo-1 of nematodes. This interaction is characterized by achieving paralysis/inhibition in particular of gastro-intestinal nematodes, of free-living nematodes, and of filariae, for which data are given in the biological experimental section. Therefore the compounds of the present invention may be used as anthelmintics for the control, treatment and/or prevention of gastro-intestinal and extra-intestinal helminth infections, in particular gastro-intestinal and extra-intestinal infections with nematodes, including filariae.

DESCRIPTION OF THE INVENTION

In accordance with a first aspect, the present invention covers compounds of general formula (I):

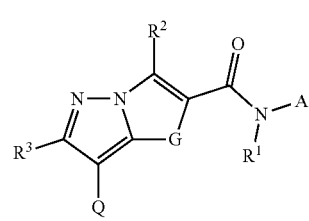

(I)

in which:
A is A1 or A2,

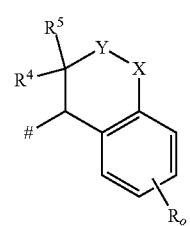

A1

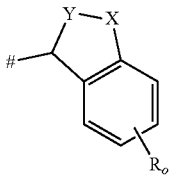

A2 o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms, X, Y are independently selected from the group consisting of $CR^6R^7$, O, S, and N—$R^8$, wherein at least one of X and Y is $CR^6R^7$, or X, Y together a ring member selected from the group consisting of —C(O)—O—, —C(O)—$NR^8$—, —S(O)—$NR^8$—, —$SO_2$—$NR^8$— and —$SO_2$—O—, G is S, O, N—$R^8$ $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;

phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —C(O)—NH($C_3$-$C_6$-cycloalkyl), —C(O)—N($C_1$-$C_4$-alkyl)($C_3$-$C_6$-cycloalkyl);

—$NR^9R^{10}$;

—$OR^{11}$;

—$SR^{12}$, —$S(O)R^{12}$, —$SO_2R^{12}$;

$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-haloalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—

$NH(C_1-C_4\text{-alkyl})$, $-C(O)-N(C_1-C_4\text{-alkyl})_2$, $C_1-C_4\text{-alkyl}$, $C_1-C_4\text{-alkyl-C(O)}-$, $C_1-C_4\text{-halogenoalkyl}$ having 1 to 5 halogen atoms, $C_1-C_4\text{-alkoxy}$, hydroxy-$C_1-C_4\text{-alkyl}$, $C_1-C_4\text{-alkoxy-}C_1-C_4\text{-alkyl-}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-NH(C_3-C_6\text{-cycloalkyl})$, $-N(C_1-C_4\text{-alkyl})(C_3-C_6\text{-cycloalkyl})$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms, $-SO_2-C_1-C_4\text{-halogenoalkyl}$ having 1 to 5 halogen atoms, and 4- to 10-membered heterocycloalkyl, $R^3$ is selected from the group consisting of hydrogen, halogen, $-OH$, cyano, $C_1-C_4\text{-alkyl}$, $C_3-C_6\text{-cycloalkyl}$, $C_1-C_4\text{-halogenoalkyl}$ having 1 to 5 halogen atoms, $C_1-C_4\text{-alkoxy-}C_1-C_4\text{-alkyl}$, $C_1-C_4\text{-alkoxy}$, $C_1-C_4\text{-alkyl-C(O)}-$, $-NH_2$, $-NH(C_1-C_4\text{-alkyl})$, $-N(C_1-C_4\text{-alkyl})_2$, $-NH(C_3-C_6\text{-cycloalkyl})$, $-N(C_1-C_4\text{-alkyl})(C_3-C_6\text{-cycloalkyl})$, $-S-C_1-C_4\text{-alkyl}$, $-S(O)-C_1-C_4\text{-alkyl}$, $-SO_2-C_1-C_4\text{-alkyl}$, $R^4$ is selected from the group consisting of hydrogen, $-OH$, $C_1-C_4\text{-alkyl}$ and $C_1-C_4\text{-alkoxy}$, $R^5$ is selected from the group consisting of hydrogen, $C_1-C_4\text{-alkyl}$ and $C_1-C_4\text{-alkoxy}$, or $R^4$ and $R^5$ form, together with the carbon atom to which they are attached, a 3- to 6-membered ring selected from the group consisting of $C_3-C_6\text{-cycloalkyl}$ and 3- to 6-membered heterocycloalkyl, $R^6$ is selected from the group consisting of hydrogen, $-OH$, fluorine, $C_1-C_4\text{-alkyl}$ and $C_1-C_4\text{-alkoxy}$, $R^7$ is selected from the group consisting of hydrogen, $-OH$, fluorine, $C_1-C_4\text{-alkyl}$ and $C_1-C_4\text{-alkoxy}$, or $R^6$ and $R^7$ form, together with the carbon atom to which they are attached, a 3- to 6-membered ring selected from the group consisting of $C_3-C_6\text{-cycloalkyl}$ and 3- to 6-membered heterocycloalkyl, $R^8$ is selected from the group consisting of hydrogen, $C_1-C_4\text{-alkyl}$, $C_1-C_4\text{-halogenoalkyl}$ having 1 to 5 halogen atoms and $C_1-C_4\text{-alkoxy}$, $R^9$ and $R^{10}$ are independently selected from the group consisting of hydrogen, $-OH$, $-NH_2$, $-NH(C_1-C_4\text{-alkyl})$, $-N(C_1-C_4\text{-alkyl})_2$, $-NH(-C(O)-C_1-C_4\text{-alkyl})$, $-N(C_1-C_4\text{-alkyl})(-C(O)-C_1-C_4\text{-alkyl})$, $C_1-C_4\text{-alkoxy}$, $C_1-C_4\text{-alkoxy-C(O)}-$;

$C_1-C_4\text{-alkyl}$, $C_3-C_6\text{-cycloalkyl}$, phenyl-$C_1-C_4\text{-alkyl}$, each of which is optionally substituted by 1, 2 or 3 substituents independently selected from the group consisting of halogen, $-OH$, cyano, $-COOH$, $C_1-C_4\text{-alkoxy-C(O)}-$, $-C(O)-NH_2$, $-C(O)-NH(C_1-C_4\text{-alkyl})$, $-C(O)-N(C_1-C_4\text{-alkyl})_2$, $-NH-C(O)-C_1-C_4\text{-alkyl}$, $-N(C_1-C_4\text{-alkyl})(-C(O)-C_1-C_4\text{-alkyl})$, $C_1-C_4\text{-alkyl}$, $C_1-C_4\text{-halogenoalkyl}$ having 1 to 5 halogen atoms, $C_1-C_4\text{-alkoxy}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms, $-SO_2-C_1-C_4\text{-halogenoalkyl}$ having 1 to 5 halogen atoms and $(C_1-C_4\text{-alkoxy})_2P(=O)-$;

heterocyclyl-$C_1-C_4\text{-alkyl}$, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, $-OH$, oxo, thiono, $-COOH$, $C_1-C_4\text{-alkoxy-C(O)}-$, $-C(O)-NH_2$, $-C(O)-NH(C_1-C_4\text{-alkyl})$, $-C(O)-N(C_1-C_4\text{-alkyl})_2$, $C_1-C_4\text{-alkyl}$, $C_1-C_4\text{-halogenoalkyl}$ having 1 to 5 halogen atoms, $C_1-C_4\text{-alkoxy}$, hydroxy-$C_1-C_4\text{-alkyl}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms and $-SO_2-C_1-C_4\text{-halogenoalkyl}$ having 1 to 5 halogen atoms;

phenyl, benzo-$C_5-C_6\text{-cycloalkyl}$, each of which is optionally substituted by 1, 2 or 3 substituents independently selected from the group consisting of halogen, cyano, nitro, $-OH$, $C_1-C_4\text{-alkyl}$, $C_1-C_4\text{-halogenoalkyl}$ having 1 to 5 halogen atoms, $C_1-C_4\text{-alkoxy}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms and $-SO_2-C_1-C_4\text{-halogenoalkyl}$ having 1 to 5 halogen atoms;

a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, $-OH$, oxo, thiono, $-COOH$, $C_1-C_4\text{-alkoxy-C(O)}-$, $-C(O)-NH_2$, $-C(O)-NH(C_1-C_4\text{-alkyl})$, $-C(O)-N(C_1-C_4\text{-alkyl})_2$, $C_1-C_4\text{-alkyl}$, $C_1-C_4\text{-halogenoalkyl}$ having 1 to 5 halogen atoms, $C_1-C_4\text{-alkoxy}$, hydroxy-$C_1-C_4\text{-alkyl}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms and $-SO_2-C_1-C_4\text{-halogenoalkyl}$ having 1 to 5 halogen atoms, $R^{11}$ is selected from the group consisting of
$-NH_2$, $-NH(C_1-C_4\text{-alkyl})$, $-N(C_1-C_4\text{-alkyl})_2$;

$C_1-C_4\text{-alkyl}$, $C_3-C_6\text{-cycloalkyl}$, phenyl-$C_1-C_4\text{-alkyl}$, each of which is optionally substituted by 1, 2 or 3 substituents independently selected from the group consisting of halogen, $-OH$, cyano, $-COOH$, $C_1-C_4\text{-alkoxy-C(O)}-$, $-C(O)-NH_2$, $-C(O)-NH(C_1-C_4\text{-alkyl})$, $-C(O)-N(C_1-C_4\text{-alkyl})_2$, $C_1-C_4\text{-alkyl}$, $C_1-C_4\text{-halogenoalkyl}$ having 1 to 5 halogen atoms, $C_1-C_4\text{-alkoxy}$, $C_1-C_4\text{-halogenoalkoxy}$ having 1 to 5 halogen atoms, $C_3-C_6\text{-cycloalkyl}$, $-NH_2$, $-NH(C_1-C_4\text{-alkyl})$, $-N(C_1-C_4\text{-alkyl})_2$, $-S-C_1-C_4\text{-alkyl}$, $-S(O)-C_1-C_4\text{-alkyl}$, $-SO_2-C_1-C_4\text{-alkyl}$, $-S-C_1-C_4\text{-halogenoalkyl}$ having 1 to 5 halogen atoms, $-S(O)-C_1-C_4\text{-halogenoalkyl}$ having 1 to 5 halogen atoms and $-SO_2-C_1-C_4\text{-halogenoalkyl}$ having 1 to 5 halogen atoms;

heterocyclyl-$C_1-C_4\text{-alkyl}$, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{12}$ is selected from the group consisting of
hydrogen;
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —CH$_2$—S—(C$_1$-C$_4$-alkyl), —CH$_2$—S(O)—(C$_1$-C$_4$-alkyl), —CH$_2$—SO$_2$—(C$_1$-C$_4$-alkyl), —S—(C$_1$-C$_4$-alkyl), —S(O)—(C$_1$-C$_4$-alkyl), —SO$_2$—(C$_1$-C$_4$-alkyl), —S—(C$_1$-C$_4$-halogenoalkyl), —S(O)—(C$_1$-C$_4$-halogenoalkyl) having 1 to 5 halogen atoms, —S(O)—(C$_1$-C$_4$-halogenoalkyl) having 1 to 5 halogen atoms, —SO$_2$—(C$_1$-C$_4$-halogenoalkyl) having 1 to 5 halogen atoms, —CONH(C$_1$-C$_4$-alkyl), —CONH(C$_3$-C$_6$-cycloalkyl), —NHCO(C$_1$-C$_4$-alkyl), —NHCO(C$_3$-C$_6$-cycloalkyl), —NHCO(C$_1$-C$_4$-halogenoalkyl) having 1 to 5 halogen atoms, wherein when Y is O, S or N—R$^8$, none of R$^4$, R$^5$, R$^6$ and R$^7$ is —OH, and wherein when X is O, S or N—R$^8$, none of R$^6$ and R$^7$ is —OH, and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. (C$_1$-C$_4$-alkoxy)-(C$_1$-C$_4$-alkyl)-, it is possible for the position of a given part to be at any suitable position of said composite substituent, i.e. the C$_1$-C$_4$-alkoxy part can be attached to any carbon atom of the C$_1$-C$_4$-alkyl part of said (C$_1$-C$_4$-alkoxy)-(C$_1$-C$_4$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

As used herein, the position via which a respective substituent is connected to the rest of the molecule may in a drawn structure be depicted by a hash sign (#) or a dashed line in said substituent.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "C$_1$-C$_6$-alkyl" means a linear or branched, saturated, monovalent hydrocarbon group having 1, 2, 3, 4, 5 or 6 carbon atoms. The term "C$_1$-C$_4$-alkyl" means a linear or branched, saturated, monovalent hydrocarbon group having 1, 2, 3, or 4 carbon atoms, e.g. a methyl, ethyl, n-propyl, isopropyl, n-butyl, sec-butyl, isobutyl or a tert-butyl group, or an isomer thereof. Particularly, said group has 1, 2 or 3 carbon atoms ("C$_1$-C$_3$-alkyl"), e.g. a methyl, ethyl, n-propyl or isopropyl group.

The term "C$_1$-C$_4$-hydroxyalkyl" means a linear or branched, saturated, monovalent hydrocarbon group in which the term "C$_1$-C$_4$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "—NH(C$_1$-C$_4$-alkyl)" or "—N(C$_1$-C$_4$-alkyl)$_2$" means a linear or branched, saturated, monovalent group in which the term "C$_1$-C$_4$-alkyl" is as defined supra, e.g. a methylamino, ethylamino, n-propylamino, isopropylamino, N,N-dimethylamino, N-methyl-N-ethylamino or N,N-diethylamino group.

The term "—S—C$_1$-C$_4$-alkyl", "—S(O)—C$_1$-C$_4$-alkyl" or "—SO$_2$—C$_1$-C$_4$-alkyl" means a linear or branched, saturated group in which the term "C$_1$-C$_4$-alkyl" is as defined supra, e.g. a methylsulfanyl, ethylsulfanyl, n-propylsulfanyl, isopropylsulfanyl, n-butylsulfanyl, sec-butylsulfanyl, isobutylsulfanyl or tert-butylsulfanyl group, a methylsulfinyl, ethylsulfinyl, n-propylsulfinyl, isopropylsulfinyl, n-butylsulfinyl, sec-butylsulfinyl, isobutylsulfinyl or tert-butylsulfinyl group, or a methylsulfonyl, ethylsulfonyl, n-propylsulfonyl, isopropylsulfonyl, n-butylsulfonyl, sec-butylsulfonyl, isobutylsulfonyl or tert-butylsulfonyl group.

The term "C$_1$-C$_4$-halogenoalkyl" means a linear or branched, saturated, monovalent hydrocarbon group in which the term "C$_1$-C$_4$-alkyl" is as defined supra, and in which one or more of the hydrogen atoms are replaced, identically or differently, with a halogen atom. Particularly, said halogen atom is a fluorine atom. More particularly, all said halogen atoms are fluorine atoms ("C$_1$-C$_4$-fluoroalkyl"). Said C$_1$-C$_4$-halogenoalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "C$_1$-C$_4$-alkoxy" means a linear or branched, saturated, monovalent group of formula (C$_1$-C$_4$-alkyl)-O—, in which the term "C$_1$-C$_4$-alkyl" is as defined supra, e.g. a methoxy, ethoxy, n-propoxy, isopropoxy, n-butoxy, sec-butoxy, isobutoxy or tert-butoxy group, or an isomer thereof.

The term "C$_1$-C$_4$-halogenoalkoxy" means a linear or branched, saturated, monovalent C$_1$-C$_4$-alkoxy group, as defined supra, in which one or more of the hydrogen atoms is replaced, identically or differently, with a halogen atom. Particularly, said halogen atom is a fluorine atom. Said C$_1$-C$_4$-halogenoalkoxy group is, for example, fluoromethoxy, difluoromethoxy, trifluoromethoxy, 2,2,2-trifluoroethoxy or pentafluoroethoxy.

The term "$C_2$-$C_4$-alkenyl" means a linear or branched, monovalent hydrocarbon group, which contains one double bond, and which has 2, 3 or 4 carbon atoms. Said $C_2$-$C_4$-alkenyl group is, for example, an ethenyl (or "vinyl"), a prop-2-en-1-yl (or "allyl"), prop-1-en-1-yl, but-3-enyl, but-2-enyl, but-1-enyl, prop-1-en-2-yl (or "isopropenyl"), 2-methylprop-2-enyl, 1-methylprop-2-enyl, 2-methylprop-1-enyl or a 1-methylprop-1-enyl, group. Particularly, said group is allyl.

The term "$C_2$-$C_4$-alkynyl" means a linear monovalent hydrocarbon group which contains one triple bond, and which contains 2, 3 or 4 carbon atoms. Said $C_2$-$C_4$-alkynyl group is, for example, an ethynyl, a prop-1-ynyl, prop-2-ynyl (or "propargyl"), but-1-ynyl, but-2-ynyl, but-3-ynyl or 1-methylprop-2-ynyl, group. Particularly, said alkynyl group is prop-1-ynyl or prop-2-ynyl.

The term "$C_3$-$C_6$-cycloalkyl" means a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_3$-$C_6$-halogenocycloalkyl" means a saturated, monovalent, monocyclic hydrocarbon ring in which the term "$C_3$-$C_6$-cycloalkyl" is as defined supra, and in which one or more of the hydrogen atoms are replaced, identically or differently, with a halogen atom. Particularly, said halogen atom is a fluorine or chlorine atom. Said $C_3$-$C_6$-halogenocycloalkyl group is for example, a monocyclic hydrocarbon ring substituted with one or two fluorine or chlorine atoms, e.g. a 1-fluoro-cyclopropyl, 2-fluorocyclopropyl, 2,2-difluorocyclopropyl, 2,3-difluorocyclopropyl, 1-chlorocyclopropyl, 2-chlorocyclopropyl, 2,2-dichlorocyclopropyl, 2,3-dichlorocyclopropyl, 2-fluoro-2-chlorocyclopropyl and 2-fluoro-3-chlorocyclopropyl group.

The term "—NH($C_3$-$C_6$-cycloalkyl)" or "—N($C_1$-$C_4$-alkyl)($C_3$-$C_6$-cycloalkyl)" means a linear or branched, saturated, monovalent group in which the term "$C_1$-$C_4$-alkyl" and the term "$C_3$-$C_6$-cycloalkyl" each is as defined supra, e.g. a cyclopropylamino, cyclobutylamino, cyclopentylamino, cyclohexylamino, N-methyl-N-cyclopropylamino, N-ethyl-N-cyclopropylamino, N-methyl-N-cyclobutylamino, N-ethyl-N-cyclobutylamino, N-methyl-N-cyclopentylamino, N-ethyl-N-cyclopentylamino, N-methyl-N-cyclohexylamino, or N-ethyl-N-cyclohexylamino group.

The term "benzo-$C_5$-$C_6$-cycloalkyl" means a monovalent, bicyclic hydrocarbon ring wherein a saturated, monovalent, monocyclic hydrocarbon ring which contains 5 or 6 carbon atoms ("$C_5$-$C_6$-cycloalkyl") is annelated to a phenyl ring. Said benzo-$C_5$-$C_6$-cycloalkyl group is for example, a bicyclic hydrocarbon ring, e.g. an indane (i.e. 2,3-dihydro-1H-indene) or tetraline (i.e. 1,2,3,4-tetrahydronaphthalene) group.

The term "spirocycloalkyl" means a saturated, monovalent bicyclic hydrocarbon group in which the two rings share one common ring carbon atom, and wherein said bicyclic hydrocarbon group contains 5, 6, 7, 8, 9, 10 or 11 carbon atoms, it being possible for said spirocycloalkyl group to be attached to the rest of the molecule via any one of the carbon atoms except the spiro carbon atom. Said spirocycloalkyl group is, for example, spiro[2.2]pentyl, spiro[2.3]hexyl, spiro[2.4]heptyl, spiro[2.5]octyl, spiro[2.6]nonyl, spiro[3.3]heptyl, spiro[3.4]octyl, spiro[3.5]nonyl, spiro[3.6]decyl, spiro[4.4]nonyl, spiro[4.5]decyl, spiro[4.6]undecyl or spiro[5.5]undecyl.

The term "heterocycloalkyl" means a monocyclic or bicyclic, saturated or partially saturated heterocycle with 4, 5, 6, 7, 8, 9 or 10 ring atoms in total (a "4- to 10-membered heterocycloalkyl" group), particularly 4, 5 or 6 ring atoms (a "4- to 6-membered heterocycloalkyl" group), which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl, 1,3-thiazolidinyl or 1,2,4-triazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example; or a 7-membered ring, such as azepanyl, 1,4-diazepanyl or 1,4-oxazepanyl, for example; or a bicyclic 7-membered ring, such as 6-oxa-3-azabicyclo[3.1.1]heptan, for example; or a bicyclic 8-membered ring, such as 5,6-dihydro-4H-furo[2,3-c]pyrrole or 8-oxa-3-azabicyclo[3.2.1]octan, for example; or a bicyclic 9-membered ring, such as octahydro-1H-pyrrolo[3,4-b]pyridine, 1,3-dihydro-isoindol, 2,3-dihydro-indol or 3,9-dioxa-7-azabicyclo[3.3.1]nonan, for example; or a bicyclic 10-membered ring, such as decahydroquinoline or 3,4-dihydroisoquinolin, for example.

The term "heterospirocycloalkyl" means a bicyclic, saturated heterocycle with 6, 7, 8, 9, 10 or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spino carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxaaspiro[4.3]octyl, oxaazaspiro[2.5]octyl, azaspiro[4.5]decyl, oxazaspiro[5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "6- or 10-membered aryl" means a monovalent, monocyclic or bicyclic aromatic ring having 6 or 10 carbon ring atoms, e.g. a phenyl or naphthyl group.

The term "heteroaryl" means a monovalent, monocyclic, bicyclic or tricyclic aromatic ring having 5, 6, 9 or 10 ring atoms (a "5- to 10-membered heteroaryl" group), particularly 5 or 6 ring atoms (a "5- to 6-membered heteroaryl" group), which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl.

The term "heterocyclyl" means a heterocycle selected from the group consisting of heterocycloalkyl and heteroaryl. Particularly, the term "4- to 6-membered heterocyclyl" means a heterocycle selected from the group consisting of 4- to 6-membered heterocycloalkyl and 5- to 6-membered heteroaryl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_4$", as used in the present text, e.g. in the context of the definition of "$C_1$-$C_4$-alkyl", "$C_1$-$C_4$-halogenoalkyl", "$C_1$-$C_4$-hydroxyalkyl", "$C_1$-$C_4$-alkoxy" or "$C_1$-$C_4$-halogenoalkoxy" means an alkyl group having a finite number of carbon atoms of 1 to 4, i.e. 1, 2, 3 or 4 carbon atoms.

Further, as used herein, the term "$C_3$-$C_6$", as used in the present text, e.g. in the context of the definition of "$C_3$-$C_6$-cycloalkyl" or $C_3$-$C_6$-halogenocycloalkyl, means a cycloalkyl group having a finite number of carbon atoms of 3 to 6, i.e. 3, 4, 5 or 6 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$, and $C_3$-$C_4$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_4$" encompasses $C_3$, $C_4$, and $C_3$-$C_4$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl) sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

An oxo substituent in the context of the invention means an oxygen atom, which is bound to a carbon atom via a double bond.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains a substitution pattern resulting in α-CH-moiety at the bicyclic pyrazole that has an increased C—H-acidity can exist as a tautomer, or even a mixture in any amount of the two tautomers.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

A is A1 or A2,

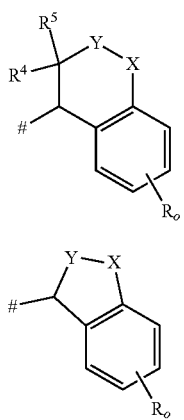

o is 0, 1, 2, 3 or 4,
R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms,
X, Y are independently selected from the group consisting of $CR^6R^7$, O, S, and N—$R^8$, wherein at least one of X and Y is $CR^6R^7$, or
X, Y form together a ring member selected from the group consisting of —C(O)—O—, —C(O)—$NR^8$—, —S(O)—$NR^8$—, —$SO_2$—$NR^8$— and —$SO_2$—O—,
G is S, O, N—$R^8$
$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;
phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms,
$R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —C(O)—NH($C_3$-$C_6$-cycloalkyl), —C(O)—N($C_1$-$C_4$-alkyl)($C_3$-$C_6$-cycloalkyl);
—$NR^9R^{10}$;
—$OR^{11}$;
—$SR^{12}$, —S(O)$R^{12}$, —$SO_2R^{12}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-alkyl-C(O)—, C$_1$-C$_4$-halogenoalkyl having 1 to 5 halogen atoms, C$_1$-C$_4$-alkoxy, hydroxy-C$_1$-C$_4$-alkyl, C$_1$-C$_4$-alkoxy-C$_1$-C$_4$-alkyl-, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and 4- to 10-membered heterocycloalkyl, $R^3$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-alkyl-C(O)—, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), —S—C$_1$-C$_4$-alkyl, —S(O)—C$_1$-C$_4$-alkyl, —SO$_2$—C$_1$-C$_4$-alkyl, $R^4$ is selected from the group consisting of hydrogen, —OH, C$_1$-C$_4$-alkyl and C$_1$-C$_4$-alkoxy, $R^5$ is selected from the group consisting of hydrogen, C$_1$-C$_4$-alkyl and C$_1$-C$_4$-alkoxy, $R^6$ is selected from the group consisting of hydrogen, —OH, fluorine, C$_1$-C$_4$-alkyl and C$_1$-C$_4$-alkoxy, $R^7$ is selected from the group consisting of hydrogen, —OH, fluorine, C$_1$-C$_4$-alkyl and C$_1$-C$_4$-alkoxy, $R^8$ is selected from the group consisting of hydrogen, C$_1$-C$_4$-alkyl, C$_1$-C$_4$-halogenoalkyl having 1 to 5 halogen atoms and C$_1$-C$_4$-alkoxy, $R^9$ and $R^{10}$ are independently selected from the group consisting of
hydrogen, —OH, —NH$_2$, —NH(C$_1$-C$_4$-alkyl), —N(C$_1$-C$_4$-alkyl)$_2$, —NH(—C(O)—C$_1$-C$_4$-alkyl), C$_1$-C$_4$-alkoxy;
C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —NH—C(O)—C$_1$-C$_4$-alkyl, —N(C$_1$-C$_4$-alkyl)-(—C(O)—C$_1$-C$_4$-alkyl), C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms and (C$_1$-C$_4$-alkoxy)$_2$P(=O)—;

heterocyclyl-C$_1$-C$_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms;

phenyl, benzo-C$_5$-C$_6$-cycloalkyl, each of which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms, $R^{11}$ is selected from the group consisting of
—NH$_2$, —NH(C$_1$-C$_4$-alkyl), —N(C$_1$-C$_4$-alkyl)$_2$;
C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—

$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{12}$ is selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is a substituted phenyl ring of the formula (Q1)

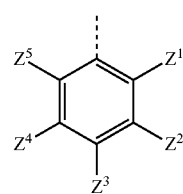

(Q1)

in which:

$Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NHSO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—SO$_2$—($C_1$-$C_4$-alkyl), —N(SO$_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl or cyano, —CH$_2$—O—($C_1$-$C_4$-alkyl), —CH$_2$—NH($C_1$-$C_4$-alkyl), —CH$_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —CH$_2$—S—($C_1$-$C_4$-alkyl), —CH$_2$—S(O)—($C_1$-$C_4$-alkyl), —CH$_2$—SO$_2$—($C_1$-$C_4$-alkyl), —S—($C_1$-$C_4$-alkyl), —S(O)—($C_1$-$C_4$-alkyl), —SO$_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), —NHCO($C_1$-$C_4$-halogenoalkyl) having 1 to 5 halogen atoms, or Q is a pyridine ring of the formula (Q2)

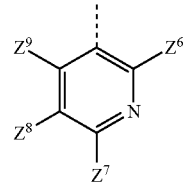

(Q2)

in which:

$Z^6$, $Z^7$, $Z^8$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a pyrimidine ring of the formula (Q3)

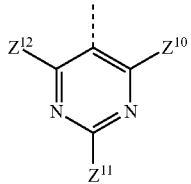
(Q3)

in which:
$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a pyridine ring of the formula (Q4)

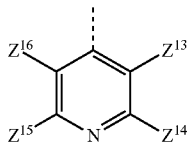
(Q4)

in which:
$Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or Q is a pyridine ring of the formula (Q5)

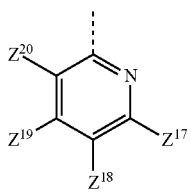
(Q5)

in which:
$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a 5-membered aromatic heterocycle of the formula (Q6)

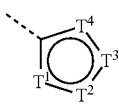
(Q6)

in which:
$T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

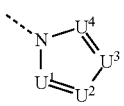
(Q7)

in which:
$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein when Y is O, S or N—$R^8$, none of $R^4$, $R^5$, $R^6$ and $R^7$ is —OH, and wherein when X is O, S or N—$R^8$, none of $R^6$ and $R^7$ is —OH, and stereoisomers, tautomers, N-oxides, hydrates, solvates, and salts thereof, and mixtures of same.

In accordance with a third embodiment of the first aspect, the present invention covers compounds of general formula (I), supra, in which:

A is A1 or A2,

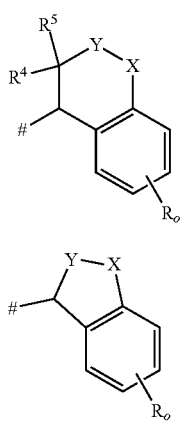

o is 0, 1, 2, 3 or 4,
R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl and —$SO_2$—$C_1$-$C_4$-halogenoalkyl having 1 to 5 halogen atoms,
X, Y are independently selected from the group consisting of $CR^6R^7$, O, S, and N—$R^8$, wherein at least one of X and Y is $CR^6R^7$, or
X, Y form together a ring member selected from the group consisting of —C(O)—O—, —C(O)—$NR^8$—, —S(O)—$NR^8$—, —$SO_2$—$NR^8$— and —$SO_2$—O—,
G is S, O, N—$R^8$
$R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, $NH_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, and —$SO_2$—$C_1$-$C_4$-halogenoalkyl having 1 to 5 halogen atoms;
phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms,
$R^2$ is selected from the group consisting of
hydrogen, halogen, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —C(O)—NH($C_3$-$C_6$-cycloalkyl), —C(O)—N($C_1$-$C_4$-alkyl)($C_3$-$C_6$-cycloalkyl);
—$NR^9R^{10}$;
—$OR^{11}$;
—$SR^{12}$, —S(O)$R^{12}$, —$SO_2R^{12}$;
$C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;
phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and 4- to 10-membered heterocycloalkyl, $R^3$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, $R^4$ is selected from the group consisting of hydrogen, —OH, $C_1$-$C_4$-alkyl and $C_1$-$C_4$-alkoxy, $R^5$ is selected from the group consisting of hydrogen, $C_1$-$C_4$-alkyl and $C_1$-$C_4$-alkoxy, $R^6$ is selected from the group consisting of hydrogen, —OH, fluorine, $C_1$-$C_4$-alkyl and $C_1$-$C_4$-alkoxy, $R^7$ is selected from the group consisting of hydrogen, —OH, fluorine, $C_1$-$C_4$-alkyl and $C_1$-$C_4$-alkoxy, $R^8$ is selected from the group consisting of hydrogen, $C_1$-$C_4$-alkyl, $C_1$-$C_4$-halogenoalkyl having 1 to 5 halogen atoms and $C_1$-$C_4$-alkoxy, $R^9$ and $R^{10}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{11}$ is selected from the group consisting of
—$NH_2$, —NH($C_1$-$C_4$-alkyl), —N($C_1$-$C_4$-alkyl)$_2$;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms; and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, $R^{12}$ is selected from the group consisting of hydrogen;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms and —$SO_2$—$C_1$-$C_4$-halogenoalkyl having 1 to 5 halogen atoms, Q is a substituted phenyl ring of the formula (Q1)

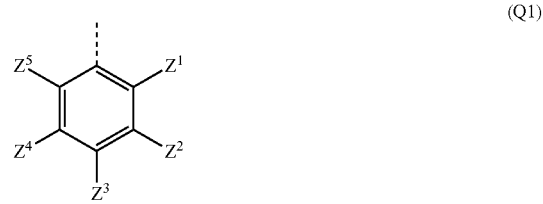

(Q1)

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH ($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —SO$_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or Q is a pyridine ring of the formula (Q2)

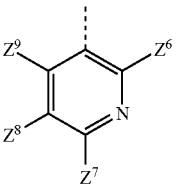

(Q2)

in which:

$Z^6$, $Z^7$, $Z^8$ and $Z^9$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a pyrimidine ring of the formula (Q3)

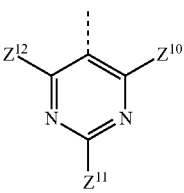

(Q3)

in which:

$Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a pyridine ring of the formula (Q4)

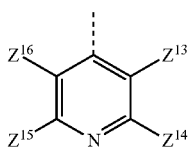

(Q4)

in which:

$Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or Q is a pyridine ring of the formula (Q5)

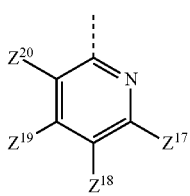

(Q5)

in which:

$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), or Q is a 5-membered aromatic heterocycle of the formula (Q6)

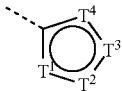
(Q6)

in which:
T$^1$-T$^4$ are independently selected from the group consisting of N, O, S, C—Z$^{21}$ and N—Z$^{22}$, wherein not more than one of T$^1$-T$^4$ is O, not more than one of T$^1$-T$^4$ is S, not more than one of T$^1$-T$^4$ is N—Z$^{22}$, and wherein
each Z$^{21}$ is independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, and
each Z$^{22}$ is independently selected from the group consisting of hydrogen, C$_1$-C$_4$-alkyl, C$_1$-C$_4$-halogenoalkyl having 1 to 5 halogen atoms, C$_1$-C$_4$-alkyl-C$_3$-C$_6$-cycloalkyl, C$_1$-C$_4$-alkoxy-C$_1$-C$_4$-alkyl, or Q is a 5-membered aromatic heterocycle of the formula (Q7)

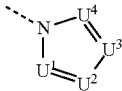
(Q7)

in which:
U$^1$-U$^4$ are independently selected from the group consisting of N and C—Z$^{23}$, wherein not more than three of U$^1$-U$^4$ are N, and wherein
each Z$^{23}$ is independently selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy,
wherein when Y is O, S or N—R$^8$, R$^4$ is not —OH,
and stereoisomers, tautomers, N-oxides, hydrates, solvates, and salts thereof, and mixtures of same.

In accordance with a fourth embodiment of the first aspect, the present invention covers compounds of general formula (I), supra, in which:
A is A1 or A2,

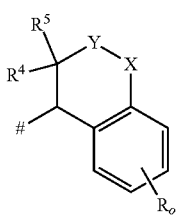
A1

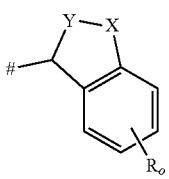
A2 o is 0, 1 or 2,
R is selected from the group consisting of hydrogen, halogen, C$_1$-C$_4$-alkyl and C$_1$-C$_4$-alkoxy, cyano, C$_1$-C$_4$-halogenoalkyl having 1 to 5 halogen atoms,
X, Y are independently selected from the group consisting of CR$^6$R$^7$, O, S, and N—R$^8$, wherein at least one of X and Y is CR$^6$R$^7$,
G is S, O, N—R$^8$
R$^1$ is selected from the group consisting of hydrogen, C$_1$-C$_4$-alkyl, C$_3$-C$_6$-cycloalkyl, C$_3$-C$_4$-alkenyl, C$_3$-C$_4$-alkynyl, C$_1$-C$_4$-alkoxy-C$_1$-C$_4$-alkyl, C$_3$-C$_6$-cycloalkyl-C$_1$-C$_3$-alkyl, cyano-C$_1$-C$_4$-alkyl,
R$^2$ is selected from the group consisting of
hydrogen, halogen, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —C(O)—NH(C$_3$-C$_6$-cycloalkyl), —C(O)—N(C$_1$-C$_4$-alkyl)(C$_3$-C$_6$-cycloalkyl);
—NR$^9$R$^{10}$;
—OR$^{11}$;
—SR$^{12}$, —S(O)R$^{12}$, —SO$_2$R$^{12}$;
C$_1$-C$_4$-alkyl, C$_3$-C$_6$-cycloalkyl, C$_2$-C$_4$-alkenyl, C$_3$-C$_6$-cycloalkenyl, C$_2$-C$_4$-alkynyl or phenyl-C$_1$-C$_4$-alkyl, each of which is optionally substituted by 1, 2, 3, 4 or 5 substituents independently selected from the group consisting of halogen, —OH, cyano, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms and —SO$_2$—C$_1$-C$_4$-halogenoalkyl having 1 to 5 halogen atoms; and
a monocyclic or a bicyclic heterocycle selected from the group consisting of 4- to 10-membered heterocycloalkyl, heterospirocycloalkyl, 5-membered heteroaryl and 6-membered heteroaryl, each of which is optionally substituted by 1, 2, 3 or 4 substituents independently selected from the group consisting of halogen, cyano, —OH, oxo, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-alkyl-C(O)—, C$_1$-C$_4$-halogenoalkyl having 1 to 5 halogen atoms, C$_1$-C$_4$-alkoxy, hydroxy-C$_1$-C$_4$-alkyl, C$_1$-C$_4$-alkoxy-C$_1$-C$_4$-alkyl-, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), and 4- to 10-membered heterocycloalkyl,
R$^3$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-alkyl-C(O)—, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), —S—C$_1$-C$_4$-alkyl, —S(O)—C$_1$-C$_4$-alkyl, —SO$_2$—C$_1$-C$_4$-alkyl,
R$^4$ is selected from the group consisting of hydrogen, —OH, C$_1$-C$_4$-alkyl and C$_1$-C$_4$-alkoxy,
R$^5$ is hydrogen,
R$^6$ is selected from the group consisting of hydrogen and C$_1$-C$_4$-alkyl, $R^7$ is selected from the group consisting of hydrogen and $C_1$-$C_4$-alkyl, $R^8$ is selected from the group consisting of hydrogen and $C_1$-$C_4$-alkyl, $R^9$ and $R^{10}$ are independently selected from the group consisting of
  hydrogen, —NH(—C(O)—$C_1$-$C_4$-alkyl), $C_1$-$C_4$-alkoxy;
  $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)+C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms and ($C_1$-$C_4$-alkoxy)$_2$P(=O)—;
  heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;
  phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and
  a monocyclic or a bicyclic heterocycle selected from the group of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{11}$ is selected from the group consisting of
  $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl; and
  heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

$R^{12}$ is selected from the group consisting of
  hydrogen;
  $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;
  heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms;

Q is a substituted phenyl ring of the formula (Q1)

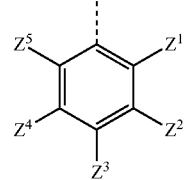

(Q1)

in which:

$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), 4- to 6-membered heterocyclyl, which is optionally substituted with 1 or 2 substituents selected from the group consisting of fluorine, chlorine, bromine, methyl and cyano, —S—($C_1$-$C_4$-alkyl), —S(O)—($C_1$-$C_4$-alkyl), —$SO_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substitutents selected from the group consisting of methyl, fluorine and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, wherein when Y is O, S or N—$R^8$, $R^4$ is not —OH, or a stereoisomer, a tautomer, an N-oxide, a hydrate, a solvate, or a salt thereof, or a mixture of same.

In accordance with a fifth embodiment of the first aspect, the present invention covers compounds of general formula (I), supra, in which:

A is A1 or A2,

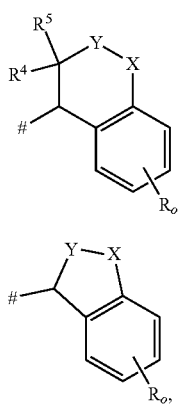

o is 0 or 1,

R is selected from the group consisting of halogen, $C_1$-$C_4$-alkyl and $C_1$-$C_4$-alkoxy, X is selected from the group consisting of $CR^6R^7$, O, S, and N—$R^8$, Y is $CR^6R^7$, G is S, O, N—$R^8$ $R^1$ is hydrogen or $C_1$-$C_4$-alkyl, $R^2$ is selected from the group consisting of
hydrogen, halogen,
—$NR^9R^{10}$;
—$OR^{11}$;
—$SR^{12}$, —S(O)$R^{12}$, —SO$_2R^{12}$;
$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, cyano, $C_1$-$C_4$-alkoxy-C(O)— and —C(O)—NH$_2$; and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—NH$_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —NH$_2$, —N($C_1$-$C_4$-alkyl)$_2$, —NH($C_3$-$C_6$-cycloalkyl), —N($C_1$-$C_4$-alkyl)($C_3$-$C_6$-cycloalkyl), and 4- to 10-membered heterocycloalkyl, $R^3$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl)-S—$C_1$-$C_4$-alkyl, —S(O)—$C_1$-$C_4$-alkyl, —SO$_2$—$C_1$-$C_4$-alkyl, $R^4$ is selected from the group consisting of hydrogen, —OH and $C_1$-$C_4$-alkyl, $R^5$ is hydrogen, $R^6$ is selected from the group consisting of hydrogen and $C_1$-$C_4$-alkyl, $R^7$ is selected from the group consisting of hydrogen and $C_1$-$C_4$-alkyl, $R^8$ is selected from the group consisting of hydrogen and $C_1$-$C_4$-alkyl, $R^9$ and $R^{10}$ are independently selected from the group consisting of
hydrogen, —NH(—C(O)—$C_1$-$C_4$-alkyl), $C_1$-$C_4$-alkoxy;

$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—NH$_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —NH$_2$, —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, and ($C_1$-$C_4$-alkoxy)$_2$P(=O)—;

heterocyclyl-$C_1$-$C_4$-alkyl, wherein the heterocyclyl substituent is selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms and $C_1$-$C_4$-alkoxy;

phenyl and benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms; and a monocyclic or a bicyclic heterocycle selected from the group of 4- to 10-membered heterocycloalkyl, 5-membered heteroaryl and 6-membered heteroaryl each of which is optionally substituted by 1, 2 or 3 substituents independently selected from the group consisting of halogen, —OH, oxo, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^{11}$ is selected from the group consisting of
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, $C_1$-$C_4$-alkyl, $C_1$-$C_4$-alkoxy and $C_3$-$C_6$-cycloalkyl; and 4- to 10-membered heterocycloalkyl, $R^{12}$ is selected from the group consisting of
hydrogen;
$C_1$-$C_4$-alkyl, which is optionally substituted by 1, 2 or 3 substituents independently selected from the group consisting of —OH and —COOH; and
a 6-membered heteroaryl, Q is a substituted phenyl ring of the formula (Q1)

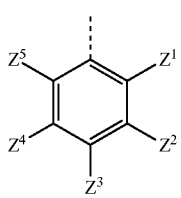

(Q1)

in which:
- $Z^1$ is selected from the group consisting of hydrogen, halogen, $C_1$-$C_4$-alkyl and $C_1$-$C_4$-alkoxy,
- $Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and
- $Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$,
- $Z^4$ is selected from the group consisting of hydrogen, halogen, $C_1$-$C_4$-alkyl, and $C_1$-$C_4$-alkoxy,
- $Z^5$ is selected from the group consisting of hydrogen, halogen, $C_1$-$C_4$-alkyl, and $C_1$-$C_4$-alkoxy, or a stereoisomer, a tautomer, an N-oxide, a hydrate, a solvate, or a salt thereof, or a mixture of same.

A further aspect of the present invention covers compounds of general formula (I), supra, in which G, A, $R^1$, $R^2$, and $R^3$ have the meaning as defined in any of the embodiments supra and Q is a substituted phenyl ring of the formula (Q1)

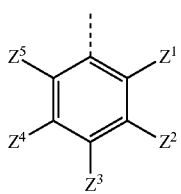

(Q1)

in which:
- $Z^1$ is selected from the group consisting of hydrogen, halogen, $C_1$-$C_4$-alkyl and $C_1$-$C_4$-alkoxy,
- $Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and
- $Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$,
- $Z^4$ is selected from the group consisting of hydrogen, halogen, $C_1$-$C_4$-alkyl, and $C_1$-$C_4$-alkoxy,
- $Z^5$ is selected from the group consisting of hydrogen, halogen, $C_1$-$C_4$-alkyl, and $C_1$-$C_4$-alkoxy, Q is a pyridine ring of the formula (Q4)

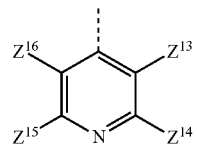

(Q4)

in which:
- $Z^{13}$, $Z^{14}$, $Z^{15}$ and $Z^{16}$ are independently selected from the group consisting of hydrogen, halogen, cyano, $C_1$-$C_4$-alkyl, $C_1$-$C_4$-alkoxy, $C_1$-$C_4$-hydroxyalkyl, NH$_2$, —NH($C_1$-$C_4$-alkyl), —N($C_1$-$C_4$-alkyl)$_2$, —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, —SO$_2$—($C_1$-$C_4$-halogenoalkyl) having 1 to 5 halogen atoms, or Q is a pyridine ring of the formula (Q5)

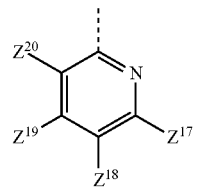

(Q5)

in which:
- $Z^{17}$, $Z^{18}$, and $Z^{19}$ are hydrogen, and
- $Z^{20}$ is halogen, or Q is a 5-membered aromatic heterocycle of the formula (Q6)

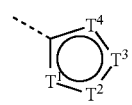

(Q6)

in which:
- $T^1$-$T^4$ are independently selected from the group consisting of N, O, S, C—$Z^{21}$ and N—$Z^{22}$, wherein not more than one of $T^1$-$T^4$ is O, not more than one of $T^1$-$T^4$ is S, not more than one of $T^1$-$T^4$ is N—$Z^{22}$, and wherein
- each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, $C_1$-$C_4$-alkoxy-$C_1$-$C_4$-alkyl, or Q is a 5-membered aromatic heterocycle of the formula (Q7)

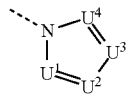

(Q7)

in which:

$U^1$-$U^4$ are independently selected from the group consisting of N and C—$Z^{23}$, wherein not more than three of $U^1$-$U^4$ are N, and wherein each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and stereoisomers, tautomers, N-oxides, hydrates, solvates, and salts thereof, and mixtures of same.

In accordance with a sixth embodiment of the first aspect, the present invention covers compounds of general formula (I), supra, in which:

A is selected from the group consisting of

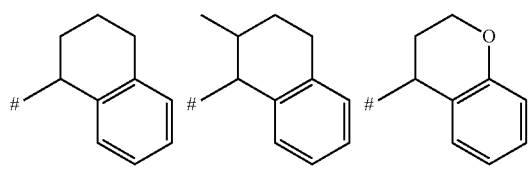

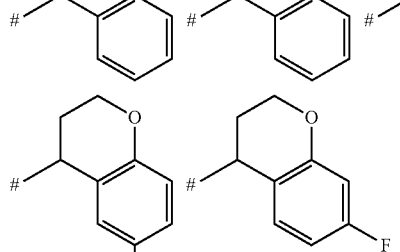

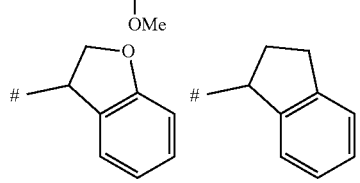

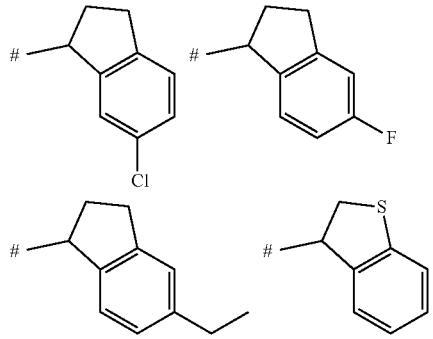

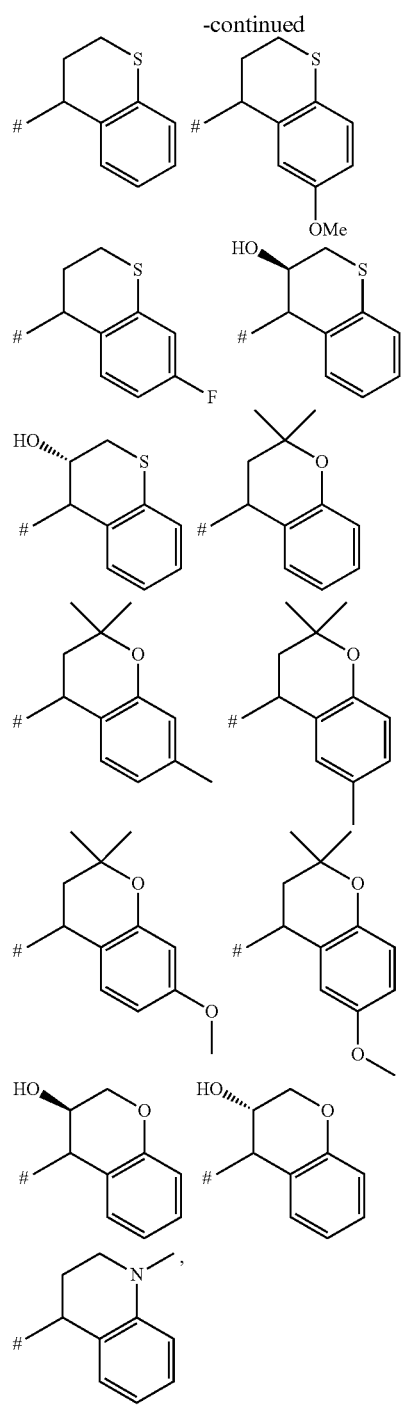

G is S, O, N—$R^8$ $R^1$ is hydrogen or methyl, $R^2$ is selected from the group consisting of
hydrogen, chlorine, fluorine,
—$NR^9R^{10}$;
—$OR^{11}$;
—$SR^{12}$, —$S(O)R^{12}$, —$SO_2R^{12}$;
methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)—, and —C(O)—$NH_2$; and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindoel, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—NH$_2$, methyl, methyl-C(O)—, trifluoromethyl, hydroxymethyl-, methoxymethyl-, —NH$_2$, —NMe$_2$, pyrrolidine, $R^3$ is selected from the group consisting of hydrogen, fluorine, chlorine, cyano, methyl, methoxy and trifluoromethyl, $R^8$ is selected from the group consisting of hydrogen and methyl, $R^9$ and $R^{10}$ are independently selected from the group consisting of hydrogen, —NH(—C(O)-methyl), methoxy;

methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—NH$_2$, —C(O)—NMe$_2$, —NH—C(O)-methyl, methyl, methoxy, cyclopropyl, —NH$_2$, NMe$_2$, S-methyl, S(O)-methyl, SO$_2$-methyl, and (EtO)$_2$P(=O)—;

heterocyclyl-methyl, heterocyclyl-ethyl, wherein the heterocyclyl substituent is selected from the group consisting of pyrrolidine, morpholine, pyrazole, 1, 2, 4-oxadiazole, pyridine, each of which is optionally substituted by 1 substituent independently selected from the group consisting of fluorine, chlorine, —OH, oxo and methyl;

phenyl;

2,3-dihydro-1H-indene, and a monocyclic or a bicyclic heterocycle selected from the group of oxetane, thietane, pyrrolidine, morpholine, tetrahydropyrane, pyridine and pyrazole, each of which is optionally substituted by 1 or 2 substituents independently selected from the group consisting of fluorine, chlorine, —OH, oxo, methyl;

$R^{11}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy and cyclopentyl; and a monocyclic or a bicyclic heterocycle selected from the group consisting of pyrrolidin and tetrahydropyran, $R^{12}$ is selected from the group consisting of methyl and ethyl, each of which is optionally substituted by 1 substituent independently selected from the group consisting of —OH and —COOH; and pyridine, Q is a substituted phenyl ring of the formula (Q1)

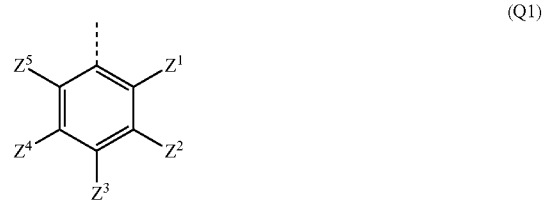

in which:

$Z^1$ is selected from the group consisting of hydrogen, halogen, $C_1$-$C_4$-alkyl and $C_1$-$C_4$-alkoxy, $Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$, $Z^4$ is selected from the group consisting of hydrogen, halogen, $C_1$-$C_4$-alkyl, and $C_1$-$C_4$-alkoxy, $Z^5$ is selected from the group consisting of hydrogen, halogen, $C_1$-$C_4$-alkyl, and $C_1$-$C_4$-alkoxy, and stereoisomers, tautomers, N-oxides, hydrates, solvates, and salts thereof, and mixtures of same.

In accordance with a seventh embodiment of the first aspect, the present invention covers compounds of general formula (I), supra, in which:

G, A, $R^1$, $R^2$, and $R^3$ have the meaning as defined for the sixth embodiment of the first aspect supra, and wherein Q is a pyridine ring of the formula (Q4)

in which:

$Z^{13}$, $Z^{14}$, $Z^{15}$ and $Z^{16}$ are independently selected from the group consisting of hydrogen, fluorine, chlorine, cyano, methyl, methoxy, ethoxy, isopropoxy, hydroxymethyl, NH$_2$, —NHMe-NMe$_2$, —NH—C(O)-Me, morpholinyl, or Q is a pyridine ring of the formula (Q5)

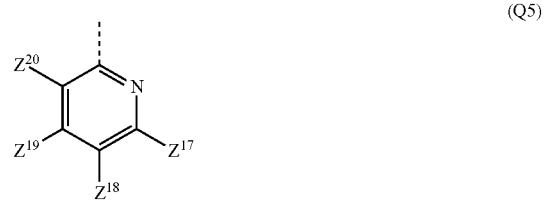

in which:
Z$^{17}$, Z$^{18}$, and Z$^{19}$ are hydrogen, and
Z$^{20}$ is fluorine, chlorine, or
Q is selected from the group consisting of
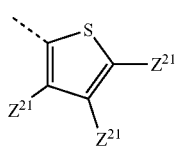 (Q6-1)
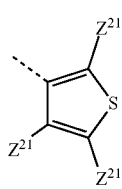 (Q6-2)
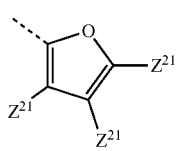 (Q6-3)
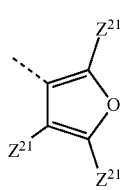 (Q6-4)
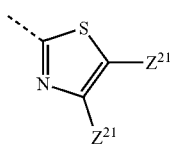 (Q6-5)
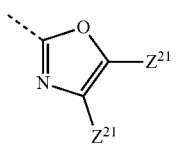 (Q6-6)
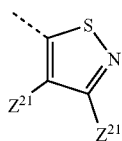 (Q6-7)
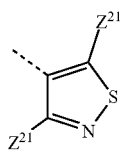 (Q6-8)
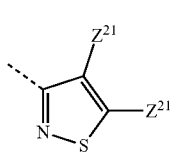 (Q6-9)
-continued
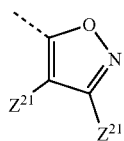 (Q6-10)
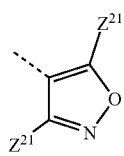 (Q6-11)
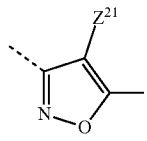 (Q6-12)
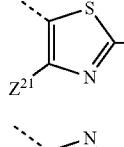 (Q6-13)
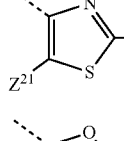 (Q6-14)
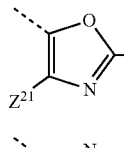 (Q6-15)
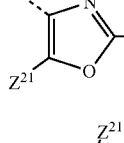 (Q6-16)
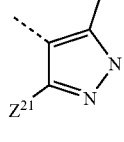 (Q6-17)
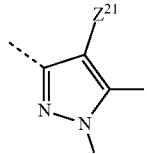 (Q6-18)
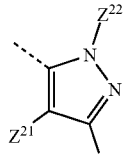 (Q6-19)
(Q6-20)

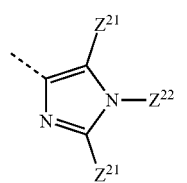 (Q6-21)
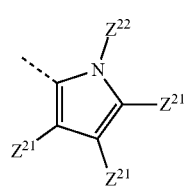 (Q6-22)
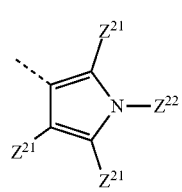 (Q6-23)
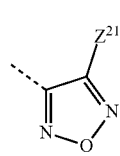 (Q6-24)
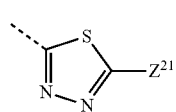 (Q6-25)
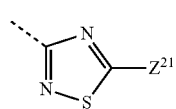 (Q6-26)
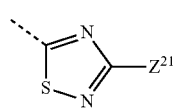 (Q6-27)
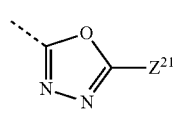 (Q6-28)
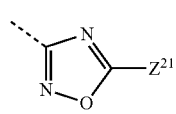 (Q6-29)
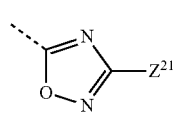 (Q6-30)
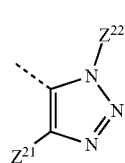 (Q6-31)
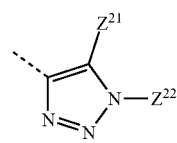 (Q6-32)
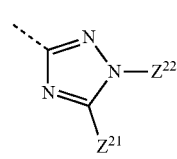 (Q6-33)
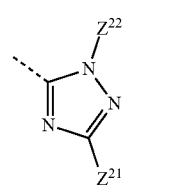 (Q6-34)
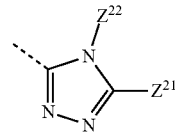 (Q6-35)
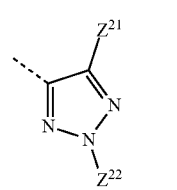 (Q6-36)
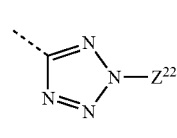 (Q6-37)
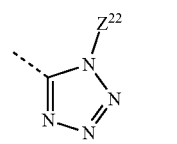 (Q6-38)
in which:
each $Z^{21}$ is independently selected from the group consisting of hydrogen, fluorine, chlorine, cyano, methyl, trifluoromethyl, methoxy and
$Z^{22}$ is hydrogen, methyl, or
Q is selected from the group consisting of
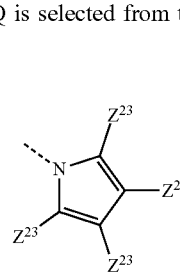 (Q7-1)

-continued (Q7-2) 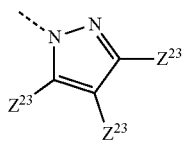

(Q7-3) 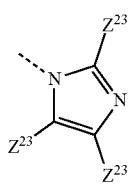

(Q7-4) 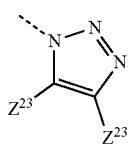

(Q7-5) 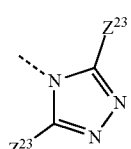

(Q7-6) 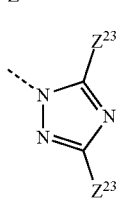

(Q7-7) 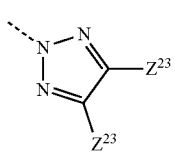

(Q7-8) 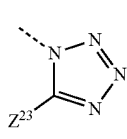

(Q7-9) 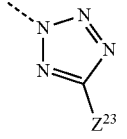

in which:
each $Z^{23}$ is independently selected from the group consisting of hydrogen, fluorine, chlorine, cyano, methyl, trifluoromethyl, methoxy, or Q is selected from the group consisting of

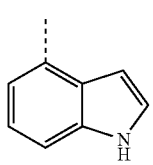 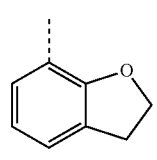 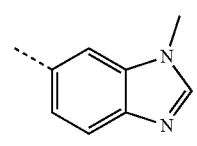

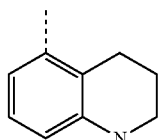 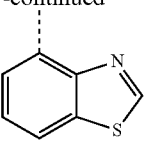 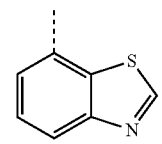

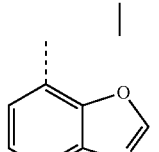 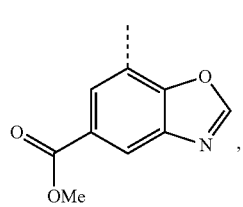

and stereoisomers, tautomers, N-oxides, hydrates, solvates, and salts thereof, and mixtures of same.

In an alternative embodiment of the sixth and seventh embodiment of the first aspect of the present invention supra, A is selected from the group consisting of:

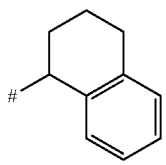 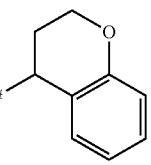 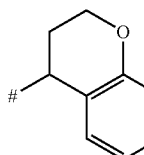

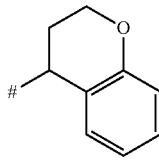 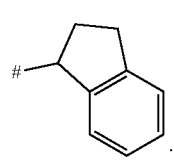

In a further alternative embodiment of the sixth and seventh embodiment of the first aspect of the present invention supra, A is selected from the group consisting of:

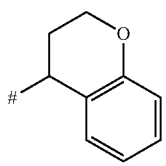 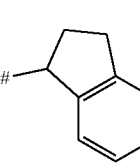

In accordance with an eighth embodiment of the first aspect, the present invention covers compounds of general formula (I), supra, in which:

A is selected from the group consisting of

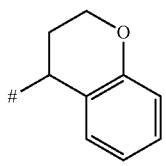 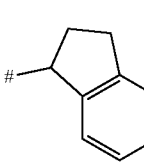

G is S, O, NH, or N—CH$_3$
$R^1$ is hydrogen or methyl,

R² is selected from the group consisting of
  hydrogen, chlorine, fluorine,
  —NH₂, —NH(CH₃), —N(CH₃)₂,
  methoxy, ethoxy,
  methyl, ethyl, propyl, isopropyl, cyclopropyl,
  trifluoromethyl and trifluoromethoxy,
R³ is selected from the group consisting of hydrogen, chlorine, fluorine, methyl, methoxy and trifluoromethyl,
Q is a substituted phenyl ring of the formula (Q1)

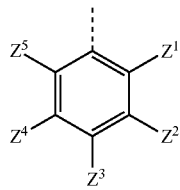

(Q1)

in which:
  Z¹ is selected from the group consisting of hydrogen, fluorine, chlorine, methyl and methoxy,
  Z² is selected from the group consisting of hydrogen, fluorine, chlorine, —OH, methyl, ethyl, methoxy, ethoxy, —NH(CH₃), —N(CH₃)₂, trifluoromethyl, trifluoromethoxy,
  Z³ is selected from the group consisting of hydrogen, fluorine, chlorine, methyl, methoxy, —NH(CH₃) and —N(CH₃)₂,
  Z⁴ is selected from the group consisting of hydrogen, fluorine, chlorine, methyl and methoxy,
  Z⁵ is selected from the group consisting of hydrogen, fluorine, chlorine methyl and methoxy,
and stereoisomers, tautomers, N-oxides, hydrates, solvates, and salts thereof, and mixtures of same.

In accordance with an ninth embodiment of the first aspect, the present invention covers compounds of general formula (I), supra, in which:
G is S, forming compounds of the general formula (II)

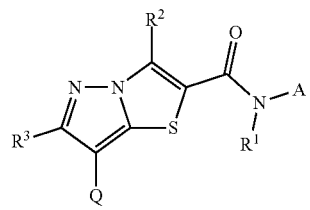

(II)

wherein
A is selected from the group consisting of

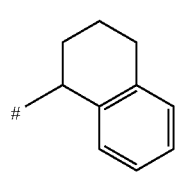 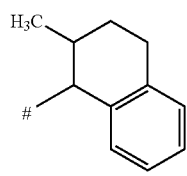

-continued

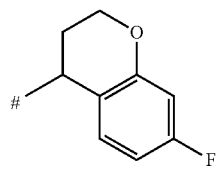 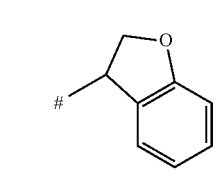

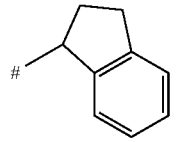 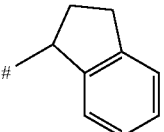

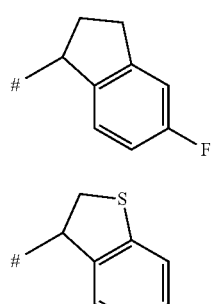 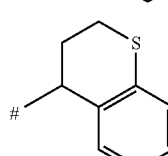

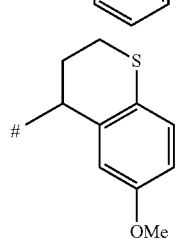 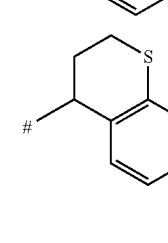

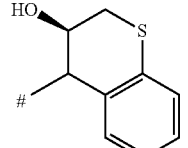 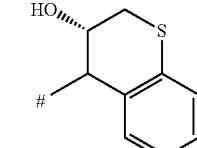

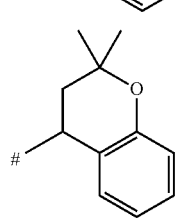 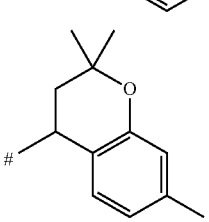

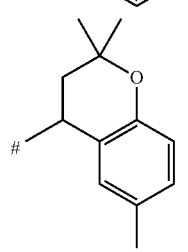 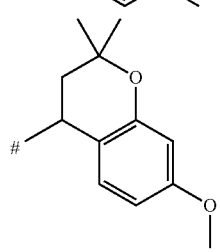

-continued

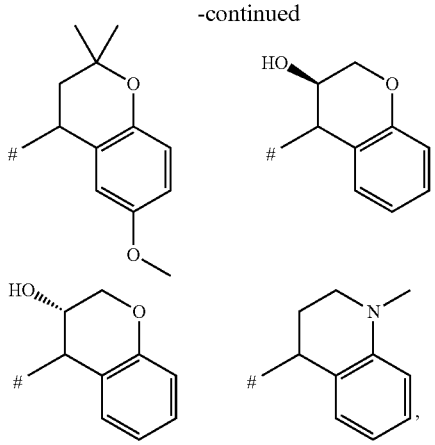

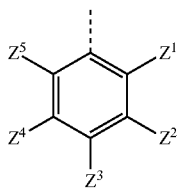

$R^1$ is hydrogen or methyl,
$R^2$ is selected from the group consisting of
  hydrogen, chlorine, fluorine,
  methoxy,
  methyl, ethyl, propyl, isopropyl,
  trifluoromethyl and trifluoromethoxy,
$R^3$ is selected from the group consisting of hydrogen, chlorine, fluorine, methyl, methoxy and trifluoromethyl,
Q is a substituted phenyl ring of the formula (Q1)

(Q1)

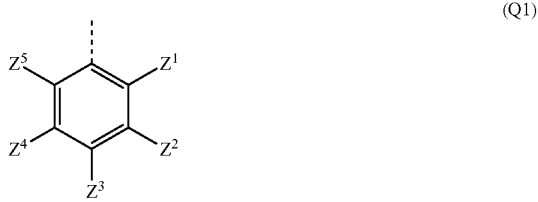

in which:
$Z^1$ is selected from the group consisting of hydrogen, halogen, $C_1$-$C_4$-alkyl and $C_1$-$C_4$-alkoxy,
$Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and
$Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$,
$Z^4$ is selected from the group consisting of hydrogen, halogen, $C_1$-$C_4$-alkyl, and $C_1$-$C_4$-alkoxy,
$Z^5$ is selected from the group consisting of hydrogen, halogen, $C_1$-$C_4$-alkyl, and $C_1$-$C_4$-alkoxy,
and stereoisomers, tautomers, N-oxides, hydrates, solvates, and salts thereof, and mixtures of same.

In accordance with an tenth embodiment of the first aspect, the present invention covers compounds of general formula (II), supra, in which:

A is selected from the group consisting of

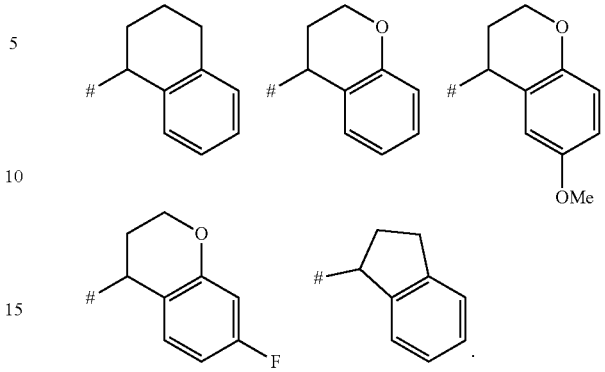

$R^1$ is hydrogen or methyl,
$R^2$ is selected from the group consisting of
  hydrogen, chlorine, fluorine,
  methoxy,
  methyl, ethyl, propyl, isopropyl,
  trifluoromethyl and trifluoromethoxy,
$R^3$ is selected from the group consisting of hydrogen, chlorine, fluorine, methyl, methoxy and trifluoromethyl,
Q is a substituted phenyl ring of the formula (Q1)

(Q1)

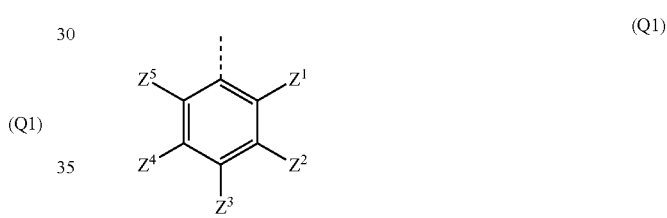

in which:
$Z^1$ is selected from the group consisting of hydrogen and halogen,
$Z^2$ is selected from the group consisting of hydrogen, halogen, —N($C_1$-$C_4$-alkyl)$_2$, —$C_1$-$C_4$-halogenoalkyl having 1 to 5 halogen atoms, and $C_1$-$C_4$-halogenoalkoxy having 1 to 5 halogen atoms,
$Z^3$ is selected from the group consisting of hydrogen and halogen,
$Z^4$ is selected from the group consisting of hydrogen and halogen,
$Z^5$ is selected from the group consisting of hydrogen and halogen,
and stereoisomers, tautomers, N-oxides, hydrates, solvates, and salts thereof, and mixtures of same.

In an alternative embodiment of the ninth and tenth embodiment of the first aspect of the present invention supra,
Q is a substituted phenyl ring of the formula (Q1)

(Q1)

in which:

$Z^1$ is selected from the group consisting of hydrogen, halogen, $C_1$-$C_4$-alkyl and $C_1$-$C_4$-alkoxy, $Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4- to 6-membered heterocycloalkyl, and $Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$, $Z^4$ is selected from the group consisting of hydrogen, halogen, $C_1$-$C_4$-alkyl, and $C_1$-$C_4$-alkoxy, $Z^5$ is selected from the group consisting of hydrogen, halogen, $C_1$-$C_4$-alkyl, and $C_1$-$C_4$-alkoxy.

In accordance with an eleventh embodiment of the first aspect, the present invention covers compounds of general formula (II), supra, in which:

A is selected from the group consisting of

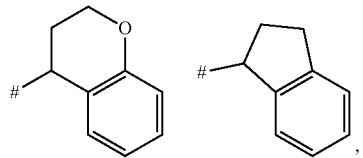

$R^1$ is hydrogen,
$R^2$ is isopropyl,
$R^3$ is methyl,
Q is a substituted phenyl ring of the formula (Q1)

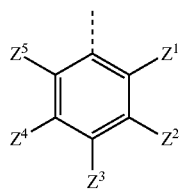

(Q1)

in which:

$Z^1$, $Z^3$, $Z^4$ and $Z^5$ are independently selected from the group consisting of hydrogen, fluorine, and chlorine, and $Z^2$ is selected from the group consisting of hydrogen, fluorine, chlorine, —N(CH$_3$)$_2$, trifluoromethyl, and trifluoromethoxy, and stereoisomers, tautomers, N-oxides, hydrates, solvates, and salts thereof, and mixtures of same.

Further embodiments of the first aspect of the present invention:

In a further embodiment the present invention covers compounds of general formula (I) or (II), supra, in which A is selected from the group consisting of

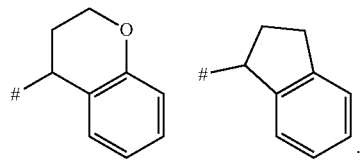

$R^1$ is hydrogen or methyl,
$R^2$ is selected from the group consisting of
hydrogen, chlorine, fluorine,
—NH$_2$, —NH(CH$_3$), —N(CH$_3$)$_2$,
methoxy, ethoxy,
methyl, ethyl, propyl, isopropyl, cyclopropyl,
trifluoromethyl and trifluoromethoxy,
$R^3$ is selected from the group consisting of hydrogen, chlorine, fluorine, methyl, methoxy and trifluoromethyl,
Q is selected from the group consisting of phenyl, 2,3,4-trifluorophenyl, 2,3,4-trichlorophenyl, 2,3,5-trichlorophenyl, 2,3,5-trifluorophenyl, 2,3,6-trifluorophenyl, 2,3,6-trichlorophenyl, 2,3-difluorophenyl, 2,3-dichlorophenyl, 2,4,5-trifluorophenyl, 2,4,5-trichlorophenyl, 2,4,6-trifluorophenyl, 2,4,6-trichlorophenyl, 2,4,6-trifluoro-3-methoxyphenyl, 2,4,6-trichloro-3-methoxyphenyl, 2,4-difluoro-3-hydroxyphenyl, 2,4-dichloro-3-hydroxyphenyl, 2,4-difluoro-3-methoxyphenyl, 2,4-dichloro-3-methoxyphenyl, 2,4-difluoro-3-(dimethylamino)phenyl, 2,4-dichloro-3-(dimethylamino)phenyl, 2,5-difluoro-4-methoxyphenyl, 2,5-dichloro-4-methoxyphenyl, 2,6-difluorophenyl, 2,6-dichlorophenyl, 2-fluoro-3-chlorophenyl, 2-chloro-3-fluorophenyl, 2-fluoro-3-(dimethylamino)phenyl, 2-chloro-3-(dimethylamino)phenyl, 2-chloro-4-fluorophenyl, 2-fluoro-4-chlorophenyl, 2-chloro-5-fluorophenyl, 2-fluoro-4-(dimethylamino)phenyl, 2-chloro-4-(dimethylamino)phenyl, 2-chloro-6-fluorophenyl, 2-fluorophenyl, 2-chlorophenyl, 2-fluoro-3-(trifluoromethoxy)phenyl, 2-chloro-3-(trifluoromethoxy)phenyl, 2-fluoro-3-(trifluoromethyl)phenyl, 2-chloro-3-(trifluoromethyl)phenyl, 3-(dimethylamino)phenyl, 3-(methylamino)phenyl, 3-(trifluoromethoxy)phenyl, 3,4,5-trifluorophenyl, 3,4,5-trichlorophenyl, 3,4-difluoro-5-(dimethylamino)phenyl, 3,4-dichloro-5-(dimethylamino)phenyl, 3,4-difluorophenyl, 3,4-dichlorophenyl, 3,4-difluoro-2-methoxyphenyl, 3,4-dichloro-2-methoxyphenyl, 3,5-difluoro-4-(dimethylamino)phenyl, 3,5-dichloro-4-(dimethylamino)phenyl, 3,5-difluoro-4-chlorophenyl, 3,5-dichloro-4-fluorophenyl, 3,5-difluorophenyl, 3,5-dichlorophenyl, 3,5-dimethylphenyl, 3-fluoro-2-chloro-5-methylphenyl, 3-chloro-2-fluoro-5-methylphenyl, 3-chloro-2-methylphenyl, 3-fluoro-4-(dimethylamino)-5-chlorophenyl, 3-fluoro-4-(dimethylamino)phenyl, 3-chloro-4-(dimethylamino)phenyl, 3-chloro-4-fluorophenyl, 3-fluoro-4-methylphenyl, 3-chloro-4-methylphenyl, 3-fluoro-5-(dimethylamino)phenyl, 3-chloro-5-(dimethylamino)phenyl, 3-fluoro-5-(methylsulfanyl)phenyl, 3-chloro-5-(methylsulfanyl)phenyl, 3-fluoro-5-(morpholin-4-yl)phenyl, 3-chloro-5-(morpholin-4-yl)phenyl, 3-fluoro-5-(trifluoromethyl)phenyl, 3-chloro-5-(trifluoromethyl)phenyl, 3-fluoro-5-ethylphenyl, 3-chloro-5-ethylphenyl, 3-chloro-5-fluorophenyl, 3-fluoro-5-methoxyphenyl, 3-chloro-5-methoxyphenyl, 3-fluoro-5-methylphenyl, 3-fluorophenyl, 3-chlorophenyl, 3-fluoro-4-methoxyphenyl, 3-chloro-4-methoxyphenyl, 3-fluoro-5-methylphenyl, 3-chloro-5-methylphenyl, 4-fluoro-3-(dimethylamino)phenyl, 4-chloro-3-(dimethylamino)phenyl, 4-fluoro-3-methoxyphenyl, 4-chloro-3-methoxyphenyl, 5-chloro-2,4-difluorophenyl, 5-fluoro-2,4-dichlorophenyl, 5-fluoro-2-chloro-3-methylphenyl, 5-chloro-2-fluoro-3-methylphenyl, 5-fluoro-2-chloro-4-methylphenyl, 5-chloro-2-fluoro-4-methylphenyl, 5-chloro-2-fluorophenyl, 5-chloro-2-methoxyphenyl, and 5-fluoro-2-methoxyphenyl, and stereoisomers, tautomers, N-oxides, hydrates, solvates, and salts thereof, and mixtures of same.

In a further embodiment the present invention covers compounds of general formula (I) or (II), supra, in which A is selected from the group consisting of

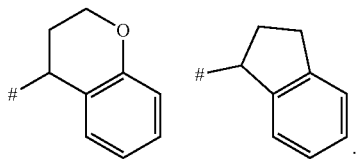

$R^1$ is hydrogen or methyl,
$R^2$ is hydrogen or isopropyl,
$R^3$ is hydrogen or methyl,
Q is selected from the group consisting of phenyl, 2,3,4-trifluorophenyl, 2,3,5-trichlorophenyl, 2,3-dichlorophenyl, 2,4-difluoro-3-(dimethylamino)phenyl, 2,6-dichlorophenyl, 2-fluoro-3-(dimethylamino)phenyl, 2-fluoro-3-(trifluoromethoxy)phenyl, 2-fluoro-3-(trifluoromethyl)phenyl, 2-chloro-3-(trifluoromethyl)phenyl, 3,4-difluorophenyl, 3,4-dichlorophenyl, 3,5-dichloro-4-fluorophenyl, 3,5-dichlorophenyl, and stereoisomers, tautomers, N-oxides, hydrates, solvates, and salts thereof, and mixtures of same.

In a further embodiment the present invention covers compounds of general formula (I), supra, in which G is S, and stereoisomers, tautomers, N-oxides, hydrates, solvates, and salts thereof, and mixtures of same.

In a further embodiment the present invention covers compounds of general formula (I) or (II), supra, in which A is selected from the group consisting of

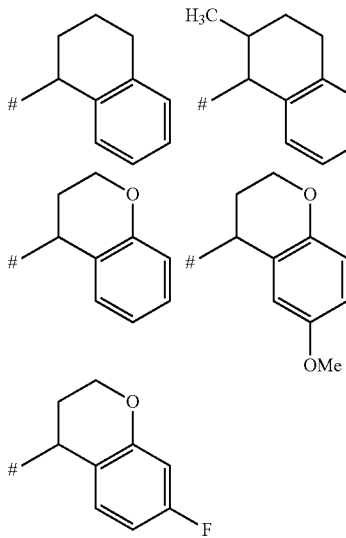

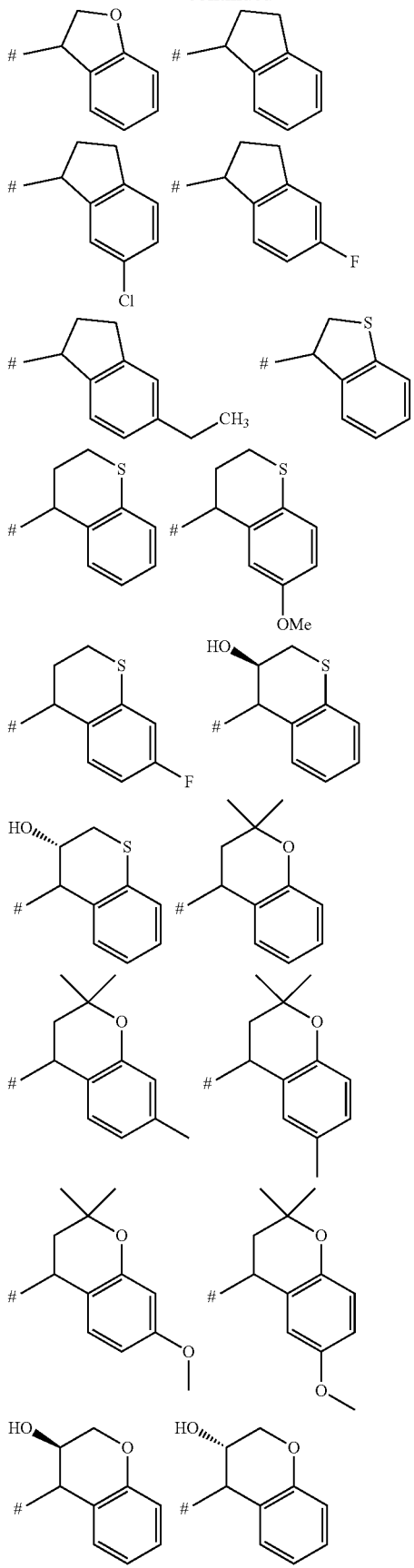

-continued

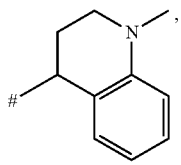

and stereoisomers, tautomers, N-oxides, hydrates, solvates, and salts thereof, and mixtures of same.

In a further embodiment the present invention covers compounds of general formula (I) or (II), supra, in which A is selected from the group consisting of

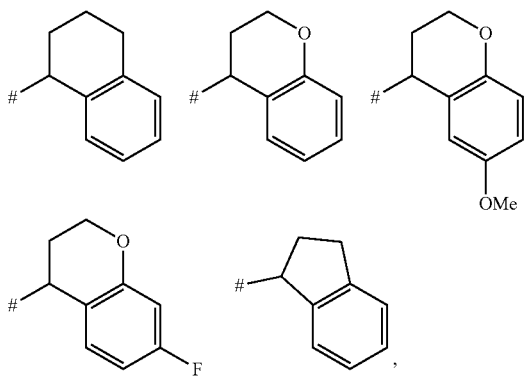

and stereoisomers, tautomers, N-oxides, hydrates, solvates, and salts thereof, and mixtures of same.

In a further embodiment the present invention covers compounds of general formula (I) or (II), supra, in which A is selected from the group consisting of

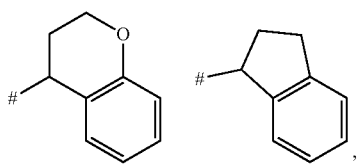

and stereoisomers, tautomers, N-oxides, hydrates, solvates, and salts thereof, and mixtures of same.

In a further embodiment the present invention covers compounds of general formula (I) or (II), supra, in which
$R^1$ is hydrogen or $C_1$-$C_4$-alkyl, such as preferably methyl, and stereoisomers, tautomers, N-oxides, hydrates, solvates, and salts thereof, and mixtures of same.

In a further embodiment the present invention covers compounds of general formula (I) or (II), supra, in which
$R^2$ is selected from the group consisting of
hydrogen, halogen,
—$NR^9R^{10}$;
—$OR^{11}$;
—$SR^{12}$, —$S(O)R^{12}$, —$SO_2R^{12}$;
$C_1$-$C_4$-alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, cyano, $C_1$-$C_4$-alkoxy-C(O)— and —C(O)—$NH_2$; and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—$NH_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —$NH_2$, —$N(C_1$-$C_4$-alkyl$)_2$, —$NH(C_3$-$C_6$-cycloalkyl), —$N(C_1$-$C_4$-alkyl)($C_3$-$C_6$-cycloalkyl), and 4- to 10-membered heterocycloalkyl, and stereoisomers, tautomers, N-oxides, hydrates, solvates, and salts thereof, and mixtures of same.

In a further embodiment the present invention covers compounds of general formula (I) or (II), supra, in which
$R^2$ is selected from the group consisting of
hydrogen, chlorine, fluorine,
—$NR^9R^{10}$;
—$OR^{11}$;
—$SR^{12}$, —$S(O)R^{12}$, —$SO_2R^{12}$;
methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)—, and —C(O)—$NH_2$; and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindoel, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—$NH_2$, methyl, methyl-C(O)—, trifluoromethyl, hydroxymethyl-, methoxymethyl-, —$NH_2$, —$NMe_2$, pyrrolidine, and stereoisomers, tautomers, N-oxides, hydrates, solvates, and salts thereof, and mixtures of same.

In a further embodiment the present invention covers compounds of general formula (I) or (II), supra, in which
$R^2$ is selected from the group consisting of
hydrogen, halogen,
—$NR^9R^{10}$,
$C_1$-$C_4$-alkoxy,
$C_1$-$C_4$-alkyl,
$C_1$-$C_4$-halogenoalkyl having 1 to 5 halogen atoms and
$C_1$-$C_4$-halogenoalkoxy having 1 to 5 halogen atoms,
and stereoisomers, tautomers, N-oxides, hydrates, solvates, and salts thereof, and mixtures of same.

In a further embodiment the present invention covers compounds of general formula (I) or (II), supra, in which
$R^2$ is selected from the group consisting of
hydrogen, chlorine, fluorine,
—$NH_2$, —$NH(CH_3)$, —$N(CH_3)_2$,
methoxy, ethoxy,
methyl, ethyl, propyl, isopropyl, cyclopropyl,
trifluoromethyl and trifluoromethoxy, wherein $R^2$ is preferably selected from the group consisting of hydrogen and isopropyl,
and stereoisomers, tautomers, N-oxides, hydrates, solvates, and salts thereof, and mixtures of same.

In a further embodiment the present invention covers compounds of general formula (I) or (II), supra, in which
$R^3$ is selected from the group consisting of hydrogen, chlorine, fluorine, methyl, methoxy and trifluoromethyl,
wherein $R^3$ is preferably selected from the group consisting of hydrogen and methyl,
and stereoisomers, tautomers, N-oxides, hydrates, solvates, and salts thereof, and mixtures of same.

In a further embodiment the present invention covers compounds of general formula (I) or (II), supra, in which
Q is a substituted phenyl ring of the formula (Q1)

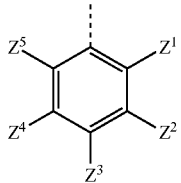

(Q1)

in which:
$Z^1$ is selected from the group consisting of hydrogen, halogen, $C_1$-$C_4$-alkyl and $C_1$-$C_4$-alkoxy,
$Z^2$ is selected from the group consisting of hydrogen, halogen, —OH, $C_1$-$C_4$-alkyl, $C_1$-$C_4$-alkoxy, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), $C_1$-$C_4$-halogenoalkyl having 1 to 5 halogen atoms, $C_1$-$C_4$-halogenoalkoxy having 1 to 5 halogen atoms, —S—($C_1$-$C_4$-alkyl) and a 4-to 6-membered heterocycloalkyl, and
$Z^3$ is selected from the group consisting of hydrogen, halogen, $C_1$-$C_4$-alkyl, $C_1$-$C_4$-alkoxy, —NH($C_1$-$C_4$-alkyl) and —N($C_1$-$C_4$-alkyl)$_2$,
$Z^4$ is selected from the group consisting of hydrogen, halogen, $C_1$-$C_4$-alkyl, and $C_1$-$C_4$-alkoxy,
$Z^5$ is selected from the group consisting of hydrogen, halogen, $C_1$-$C_4$-alkyl, and $C_1$-$C_4$-alkoxy,
and stereoisomers, tautomers, N-oxides, hydrates, solvates, and salts thereof, and mixtures of same.

In a further embodiment the present invention covers compounds of general formula (I) or (II), supra, in which
Q is a substituted phenyl ring of the formula (Q1)

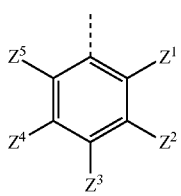

(Q1)

in which:
$Z^1$ is selected from the group consisting of hydrogen, fluorine, chlorine, methyl and methoxy,
$Z^2$ is selected from the group consisting of hydrogen, fluorine, chlorine, —OH, methyl, ethyl, methoxy, ethoxy, —NH(CH$_3$), —N(CH$_3$)$_2$, trifluoromethyl, trifluoromethoxy,
$Z^3$ is selected from the group consisting of hydrogen, fluorine, chlorine, methyl, methoxy, —NH(CH$_3$) and —N(CH$_3$)$_2$,
$Z^4$ is selected from the group consisting of hydrogen, fluorine, chlorine, methyl and methoxy,
$Z^5$ is selected from the group consisting of hydrogen, fluorine, chlorine methyl and methoxy,
and stereoisomers, tautomers, N-oxides, hydrates, solvates, and salts thereof, and mixtures of same.

In a further embodiment the present invention covers compounds of general formula (I) or (II), supra, in which
Q is a substituted phenyl ring of the formula (Q1)

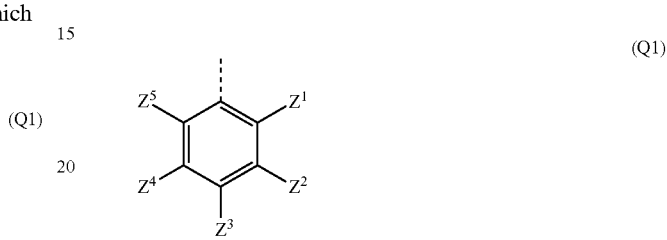

(Q1)

in which:
$Z^1$ is selected from the group consisting of hydrogen, fluorine, and chlorine,
$Z^2$ is selected from the group consisting of hydrogen, fluorine, chlorine, —N(CH$_3$)$_2$, trifluoromethyl, and trifluoromethoxy,
$Z^3$ is selected from the group consisting of hydrogen, fluorine, and chlorine,
$Z^4$ is selected from the group consisting of hydrogen, fluorine, and chlorine,
$Z^5$ is selected from the group consisting of hydrogen, fluorine, and chlorine,
and stereoisomers, tautomers, N-oxides, hydrates, solvates, and salts thereof, and mixtures of same.

In a further embodiment the present invention covers compounds of general formula (I) or (II), supra, in which
Q is a substituted phenyl ring of the formula (Q1)

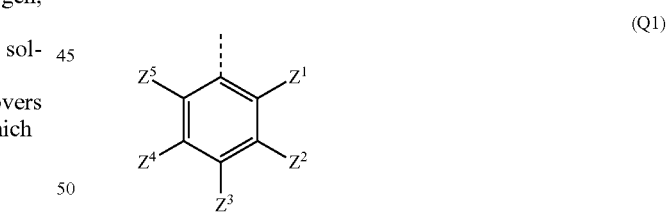

(Q1)

in which:
$Z^1$, $Z^3$, $Z^4$ and $Z^5$ are independently selected from the group consisting of hydrogen, fluorine, and chlorine, and
$Z^2$ is selected from the group consisting of hydrogen, fluorine, chlorine, —N(CH$_3$)$_2$, trifluoromethyl, and trifluoromethoxy,
and stereoisomers, tautomers, N-oxides, hydrates, solvates, and salts thereof, and mixtures of same.

In a further embodiment the present invention covers compounds of general formula (I) or (II), supra, in which
Q is selected from the group consisting of phenyl, 2,3,4-trifluorophenyl, 2,3,4-trichlorophenyl, 2,3,5-trichlorophenyl, 2,3,5-trifluorophenyl, 2,3,6-trifluorophenyl, 2,3,6-trichlorophenyl, 2,3-difluorophenyl, 2,3-dichlorophenyl, 2,4,5-trifluorophenyl, 2,4,5-trichlorophenyl, 2,4,6-trifluorophenyl, 2,4,6-trichlorophenyl, 2,4,6-trifluoro-3-methoxyphenyl, 2,4,6-trichloro-3-methoxyphenyl, 2,4-difluoro-3-hydroxyphenyl, 2,4-dichloro-3-hydroxyphenyl, 2,4-difluoro-3-methoxyphenyl, 2,4-dichloro-3-methoxyphenyl, 2,4-difluoro-3-(dimethylamino)phenyl, 2,4-dichloro-3-(dimethylamino)phenyl, 2,5-difluoro-4-methoxyphenyl, 2,5-dichloro-4-methoxyphenyl, 2,6-difluorophenyl, 2,6-dichlorophenyl, 2-fluoro-3-chlorophenyl, 2-chloro-3-fluorophenyl, 2-fluoro-3-(dimethylamino)phenyl, 2-chloro-3-(dimethylamino)phenyl, 2-chloro-4-fluorophenyl, 2-fluoro-4-chlorophenyl, 2-chloro-5-fluorophenyl, 2-fluoro-4-(dimethylamino)phenyl, 2-chloro-4-(dimethylamino)phenyl, 2-chloro-6-fluorophenyl, 2-fluorophenyl, 2-chlorophenyl, 2-fluoro-3-(trifluoromethoxy)phenyl, 2-chloro-3-(trifluoromethoxy)phenyl, 2-fluoro-3-(trifluoromethyl)phenyl, 2-chloro-3-(trifluoromethyl)phenyl, 3-(dimethylamino)phenyl, 3-(methylamino)phenyl, 3-(trifluoromethoxy)phenyl, 3,4,5-trifluorophenyl, 3,4,5-trichlorophenyl, 3,4-difluoro-5-(dimethylamino)phenyl, 3,4-dichloro-5-(dimethylamino)phenyl, 3,4-difluorophenyl, 3,4-dichlorophenyl, 3,4-difluoro-2-methoxyphenyl, 3,4-dichloro-2-methoxyphenyl, 3,5-difluoro-4-(dimethylamino)phenyl, 3,5-dichloro-4-(dimethylamino)phenyl, 3,5-difluoro-4-chlorophenyl, 3,5-dichloro-4-fluorophenyl, 3,5-difluorophenyl, 3,5-dichlorophenyl, 3,5-dimethylphenyl, 3-fluoro-2-chloro-5-methylphenyl, 3-chloro-2-fluoro-5-methylphenyl, 3-chloro-2-methylphenyl, 3-fluoro-4-(dimethylamino)-5-chlorophenyl, 3-fluoro-4-(dimethylamino)phenyl, 3-chloro-4-(dimethylamino)phenyl, 3-chloro-4-fluorophenyl, 3-fluoro-4-methylphenyl, 3-chloro-4-methylphenyl, 3-fluoro-5-(dimethylamino)phenyl, 3-chloro-5-(dimethylamino)phenyl, 3-fluoro-5-(methylsulfanyl)phenyl, 3-chloro-5-(methylsulfanyl)phenyl, 3-fluoro-5-(morpholin-4-yl)phenyl, 3-chloro-5-(morpholin-4-yl)phenyl, 3-fluoro-5-(trifluoromethyl)phenyl, 3-chloro-5-(trifluoromethyl)phenyl, 3-fluoro-5-ethylphenyl, 3-chloro-5-ethylphenyl, 3-chloro-5-fluorophenyl, 3-fluoro-5-methoxyphenyl, 3-chloro-5-methoxyphenyl, 3-fluoro-5-methylphenyl, 3-fluorophenyl, 3-chlorophenyl, 3-fluoro-4-methoxyphenyl, 3-chloro-4-methoxyphenyl, 3-fluoro-5-methylphenyl, 3-chloro-5-methylphenyl, 4-fluoro-3-(dimethylamino)phenyl, 4-chloro-3-(dimethylamino)phenyl, 4-fluoro-3-methoxyphenyl, 4-chloro-3-methoxyphenyl, 5-chloro-2,4-difluorophenyl, 5-fluoro-2,4-dichlorophenyl, 5-fluoro-2-chloro-3-methylphenyl, 5-chloro-2-fluoro-3-methylphenyl, 5-fluoro-2-chloro-4-methylphenyl, 5-chloro-2-fluoro-4-methylphenyl, 5-chloro-2-fluorophenyl, 5-chloro-2-methoxyphenyl, and 5-fluoro-2-methoxyphenyl, and stereoisomers, tautomers, N-oxides, hydrates, solvates, and salts thereof, and mixtures of same.

In a further embodiment the present invention covers compounds of general formula (I) or (II), supra, in which Q is selected from the group consisting of phenyl, 2,3,4-trifluorophenyl, 2,3,5-trichlorophenyl, 2,3-dichlorophenyl, 2,4-difluoro-3-(dimethylamino)phenyl, 2,6-dichlorophenyl, 2-fluoro-3-(dimethylamino)phenyl, 2-fluoro-3-(trifluoromethoxy)phenyl, 2-fluoro-3-(trifluoromethyl)phenyl, 2-chloro-3-(trifluoromethyl)phenyl, 3,4-difluorophenyl, 3,4-dichlorophenyl, 3,5-dichloro-4-fluorophenyl, 3,5-dichlorophenyl, and stereoisomers, tautomers, N-oxides, hydrates, solvates, and salts thereof, and mixtures of same.

In a further embodiment of the first aspect, the present invention covers compounds of formula (I), supra, in which:
A is A1 or A2,

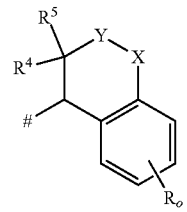

A1

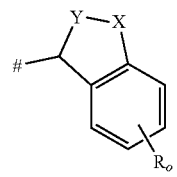

A2 o is 0, 1 or 2,
R is selected from the group consisting of hydrogen halogen, $C_1$-$C_4$-alkyl and $C_1$-$C_4$-alkoxy,
G is S, O, NH, or N—$CH_3$
X, Y are independently selected from the group consisting of $CR^6R^7$ and O, wherein at least one of X and Y is $CR^6R^7$,
$R^4$ is selected from the group consisting of hydrogen, —OH, $C_1$-$C_4$-alkyl and $C_1$-$C_4$-alkoxy, and
$R^5$ is hydrogen,
$R^6$ is selected from the group consisting of hydrogen and $C_1$-$C_4$-alkyl,
$R^7$ is selected from the group consisting of hydrogen and $C_1$-$C_4$-alkyl,
wherein when Y is O, $R^4$ is not —OH, and stereoisomers, tautomers, N-oxides, hydrates, solvates, and salts thereof, and mixtures of same.

In a further embodiment of the first aspect, the present invention covers compounds of formula (I), supra, in which
A is A3 or A4

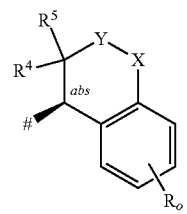

A3

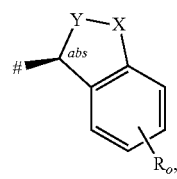

A4 and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I) or (II), supra.

The present invention covers the compounds of general formula (I) and (II) which are disclosed in the Example Section of this text, infra.

The compounds according to the invention of general formula (I) and (II) can be prepared according to the scheme 1 as shown in the Experimental Section to the present invention (General Procedures). The schemes and procedures described illustrate synthetic routes to the compounds of general formula (I) and (II) of the invention and are not intended to be limiting. It is clear to the person skilled in the art that the order of transformations as exemplified in scheme 1 can be modified in various ways. The order of transformations exemplified in these schemes is therefore not intended to be limiting. In addition, interconversion of any of the substituents, Q, A, $R^1$, $R^2$, or $R^3$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

In the following, several routes for the preparation of compounds of general formula (I) are described in scheme 1.

In accordance with a second aspect, the present invention covers methods of preparing compounds of general formula (I) and (II) as defined supra, said methods comprising the step of allowing an intermediate compound of general formula 1N:

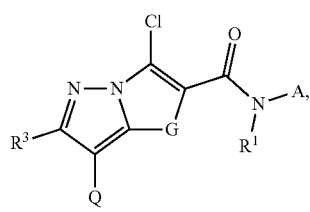

in which G, A, $R^1$, $R^3$, and Q are as defined for the compound of general formula (I) and (II) as defined supra, to react with a compound of general formula 1F:

$R^2H$        1F, in which $R^2$ is selected from the group consisting of —$NR^9R^{10}$, —$OR^{11}$, and —$SR^{12}$, in which $R^9$, $R^{10}$, $R^{11}$ and $R^{12}$ are as defined for the compound of general formula (I) and (II) as defined supra, thereby giving a compound of general formula (I), or if G is S of general formula (II):

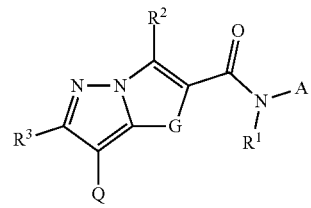

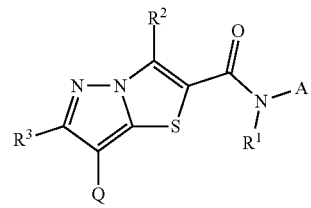

in which G, A, $R^1$, $R^2$, $R^3$, and Q are as defined supra.

In accordance with an alternative embodiment of the second aspect, the present invention covers methods of preparing compounds of general formula (I) and (II) as defined supra, said methods comprising the step of allowing an intermediate compound of general formula 1T:

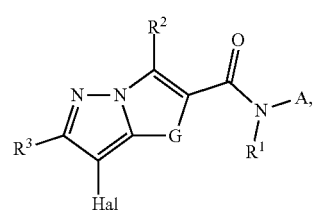

in which G, A, $R^1$, $R^2$, and $R^3$ are as defined for the compound of general formula (I) and (II) as defined supra, and in which Hal is halogen, particularly chlorine, bromine or iodine, to react with a compound of general formula 1H:

Q-B(OR)$_2$        1H, in which Q is as defined for the compound of general formula (I) and (II) as defined supra, and each R may be individually H or Me or both R are pinacolate, thereby giving a compound of general formula (I), or if G is S of general formula (II):

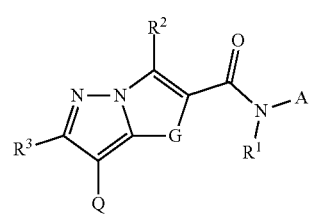

-continued

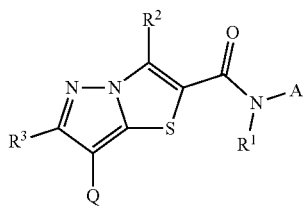
(II)

in which G, A, R$^1$, R$^2$, R$^3$, and Q are as defined supra.

In accordance with an alternative embodiment of the second aspect, the present invention covers methods of preparing compounds of general formula (I) and (II) as defined supra, said methods comprising the step of allowing an intermediate compound of general formula 1W:

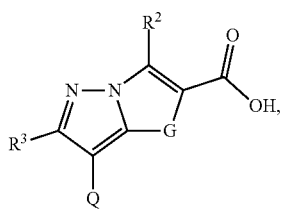
1W in which G, Q, R$^2$, and R$^3$ are as defined for the compound of general formula (I) and (II) as defined supra, to react with a compound of general formula 1M:

1M in which R$^1$ and A are as defined for the compound of general formula (I) and (II) as defined supra, thereby giving a compound of general formula (I), or if G is S of general formula (II):

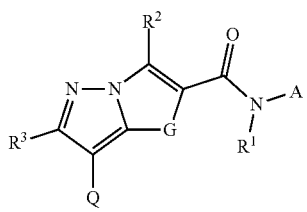
(I)

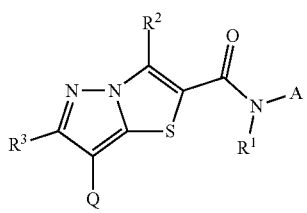
(II)

in which G, A, R$^1$, R$^2$, R$^3$, and Q are as defined supra.

In accordance with an alternative embodiment of the second aspect, the present invention covers methods of preparing compounds of general formula (I) and (II) as defined supra, said methods comprising the step of allowing an intermediate compound of general formula 1X:

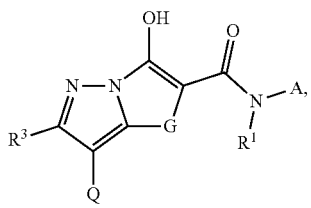
1X in which G, Q, A, R$^1$, and R$^3$ as defined for the compound of general formula (I) and (II) as defined supra, to react with a compound of general formula 1Y:

R$^2$H    1Y, in which R$^2$ is C$^1$-C$^4$-alkoxy which is optionally substituted as defined for the compound of general formula (I) and (II) as defined supra, thereby giving a compound of general formula (I), or if G is S of general formula (II):

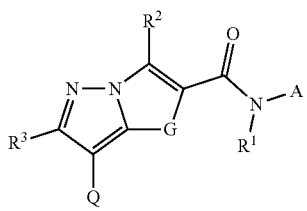
(I)

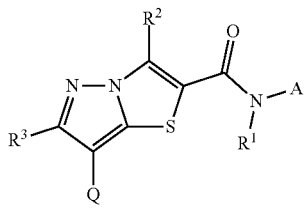
(II)

in which G, A, R$^1$, R$^3$, and Q are as defined supra and R$^2$ is C$^1$-C$^4$-alkoxy which is optionally substituted as defined supra.

In accordance with an alternative embodiment of the second aspect, the present invention covers methods of preparing compounds of general formula (I) and (II) as defined supra, said methods comprising the step of allowing an intermediate compound of general formula 1N:

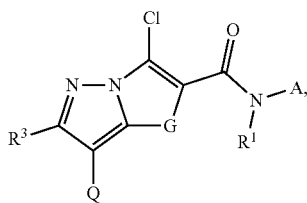
1N in which G, Q, A, R$^1$, and R$^3$ are as defined for the compound of general formula (I) and (II) as defined supra, to react with a compound of general formula 2A:

$$R^2\text{Met-X} \qquad 2A,$$

in which $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of general formula (I) and (II) as defined supra, Met is magnesium or zinc, and X is chlorine, bromine or iodine, thereby giving a compound of general formula (I), or if G is S of general formula (II):

(I)

(II)

in which G, A, $R^1$, $R^3$ and Q are as defined supra and $R^2$ is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra.

In accordance with a third aspect, the present invention covers methods of preparing compounds of general formula (I) and (II) as defined supra, said methods comprising the step of allowing an intermediate compound of general formula 1N:

1N in which G, Q, A, $R^1$, and $R^3$ are as defined for the compound of general formula (I) and (II) as defined supra, to react with a compound of general formula 1F:

$$R^2H \qquad 1F,$$

in which $R^2$ is selected from the group consisting of —$NR^9R^{10}$, —$OR^{11}$, and —$SR^{12}$, in which $R^9$, $R^{10}$, $R^{11}$ and $R^{12}$ are as defined for the compound of general formula (I) and (II) as defined supra, thereby giving a compound of general formula (I), or if G is S of general formula (II):

(I)

(II)

in which G, A, $R^1$, $R^2$, $R^3$, and Q are as defined supra, then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) and (II) as defined supra, said methods comprising the step of allowing an intermediate compound of general formula 1T:

1T in which G, A, $R^1$, $R^2$, and $R^3$ are as defined for the compound of general formula (I) and (II) as defined supra, and in which Hal is halogen, particularly chlorine, bromine or iodine, to react with a compound of general formula 1H:

$$Q\text{-B(OR)}_2 \qquad 1H,$$

in which Q is as defined for the compound of general formula (I) as defined supra, and each R may be individually H or Me or both R are pinacolate, thereby giving a compound of general formula (I), or if G is S of general formula (II):

(I)

-continued

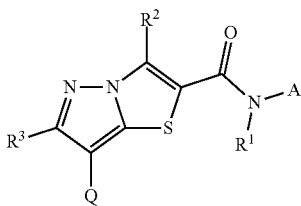
(II)

in which G, A, R¹, R², R³, and Q are as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) and (II) as defined supra, said methods comprising the step of allowing an intermediate compound of general formula 1W:

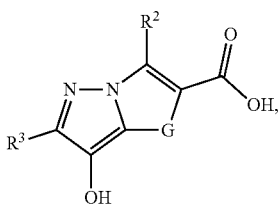
1W in which G, Q, R², and R³ are as defined for the compound of general formula (I) and (II) as defined supra,
to react with a compound of general formula 1M:

1M in which R¹ and A are as defined for the compound of general formula (I) and (II) as defined supra,
thereby giving a compound of general formula (I), or if G is S of general formula (II):

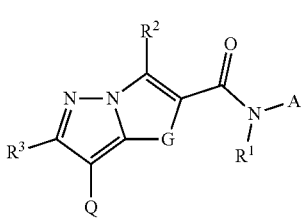
(I)

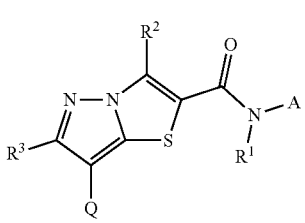
(II)

in which G, A, R¹, R², R³, and Q are as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) and (II) as defined supra, said methods comprising the step of allowing an intermediate compound of general formula 1X:

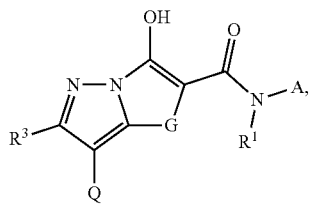
1X in which G, Q, A, R¹, and R³ are as defined for the compound of general formula (I) and (II) as defined supra,
to react with a compound of general formula 1Y:

1Y, in which R² is $C_1$-$C_4$-alkoxy which is optionally substituted as defined for the compound of general formula (I) and (II) as defined supra, thereby giving a compound of general formula (I), or if G is S of general formula (II):

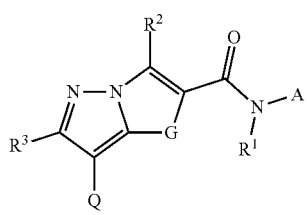
(I)

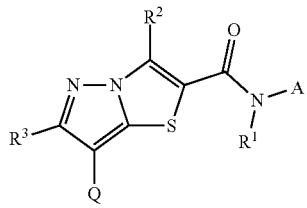
(II)

in which G, A, R¹, R³, and Q are as defined supra and R² is $C_1$-$C_4$-alkoxy which is optionally substituted as defined supra,
then optionally converting said compound into solvates, salts and/or solvates of such salts using the corresponding (i) solvents and/or (ii) bases or acids.

In accordance with an alternative embodiment of the third aspect, the present invention covers methods of preparing compounds of general formula (I) and (II) as defined supra, said methods comprising the step of allowing an intermediate compound of general formula 1N:

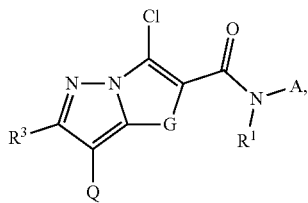

in which G, Q, A, R¹, and R³ are as defined for the compound of general formula (I) and (II) as defined supra, to react with a compound of general formula 2A:

R²Met-X    2A, in which R² is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined for the compound of general formula (I) and (II) as defined supra, Met is magnesium or zinc, and X is chlorine, bromine or iodine, thereby giving a compound of general formula (I), or if G is S of general formula (II):

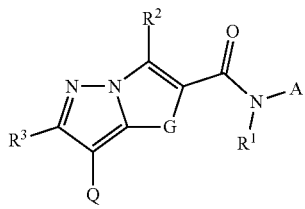

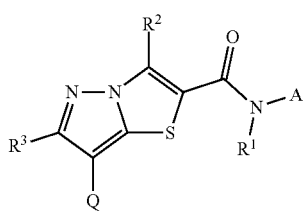

in which G, A, R¹, R³, and Q are as defined supra and R² is $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted as defined supra, then optionally converting said compound into solvates, salts and/or solvates of such salts using the corresponding (i) solvents and/or (ii) bases or acids.

The present invention covers methods of preparing compounds of the present invention of general formula (I) and (II), said methods comprising the steps as described in the Experimental Section herein.

In accordance with a fourth aspect, the present invention covers intermediate compounds which are useful for the preparation of the compounds of general formula (I) and (II), supra.

Particularly, the invention covers the intermediate compounds of general formula (I-INT):

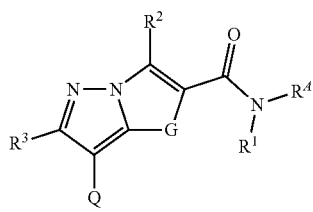

wherein G is as defined for the compound of general formula (I) and (II) supra, or when G=S of the general formula (II-INT):

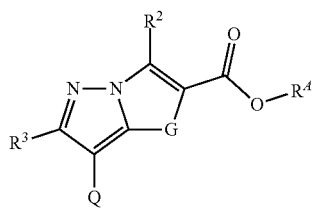

wherein in the formulae (I-INT) and (II-INT) supra

R² is selected from the group consisting of $C_1$-$C_6$-alkyl and $C_3$-$C_6$-cycloalkyl or as defined for the compound of general formula (I) and (II) supra, R³ is selected from the group consisting of hydrogen, halogen, $C_1$-$C_4$-alkyl and $C_3$-$C_6$-cycloalkyl or as defined for the compound of general formula (I) and (II) supra, Q is as defined for the compound of general formula (I) and (II) supra, and $R^A$ is H or $C_1$-$C_4$-alkyl, and stereoisomers, tautomers, N-oxides, hydrates, solvates, and salts thereof, and mixtures of same.

Particularly, the invention covers also the intermediate compounds of general formula (II-INT) supra, in which Q is hydrogen or halogen, and R² is selected from the group consisting of $C_1$-$C_6$-alkyl and $C_3$-$C_6$-cycloalkyl or as defined for the compound of general formula (I) and (II) supra, R³ is selected from the group consisting of hydrogen, halogen, $C_1$-$C_4$-alkyl and $C_3$-$C_6$-cycloalkyl or as defined for the compound of general formula (I) and (II) supra, and $R^A$ is H or $C_1$-$C_4$-alkyl;

and stereoisomers, tautomers, N-oxides, hydrates, solvates, and salts thereof, and mixtures of same.

Particularly, the invention covers also intermediate compounds of general formula (III-INT):

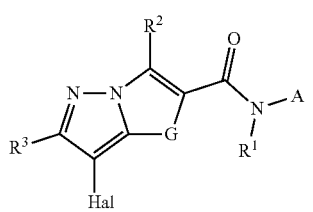

wherein G is as defined for the compound of general formula (I) and (II) supra, or when G=S of the general formula (IV-INT):

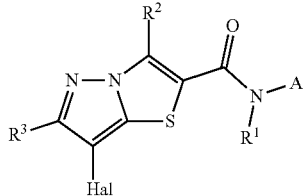

(IV-INT)

in which

Hal is halogen as defined supra, and $R^2$ is selected from the group consisting of $C_1$-$C_6$-alkyl and $C_3$-$C_6$-cycloalkyl or as defined for the compound of general formula (I) and (II) supra, $R^3$ is selected from the group consisting of hydrogen, halogen, $C_1$-$C_4$-alkyl and $C_3$-$C_6$-cycloalkyl or as defined for the compound of general formula (I) and (II) supra, and $R^1$ and A are as defined for the compound of general formula (I) and (II) supra;

and stereoisomers, tautomers, N-oxides, hydrates, solvates, and salts thereof, and mixtures of same.

More particularly, the invention covers also intermediate compounds of general formula (III-INT) or (IV-INT) supra, in which Hal is halogen as defined supra, and $R^2$ is selected from the group consisting of $C_1$-$C_6$-alkyl and $C_3$-$C_6$-cycloalkyl, $R^3$ is selected from the group consisting of hydrogen, halogen, $C_1$-$C_4$-alkyl and $C_3$-$C_6$-cycloalkyl, and $R^1$ and A are as defined for the compound of general formula (I) and (II) supra;

and stereoisomers, tautomers, N-oxides, hydrates, solvates, and salts thereof, and mixtures of same.

Particularly preferred among the intermediates (III-INT) and (IV-INT) supra are those according to formula (IV-INT) supra.

Particularly, the invention covers also the intermediate compounds of general formula (V-INT):

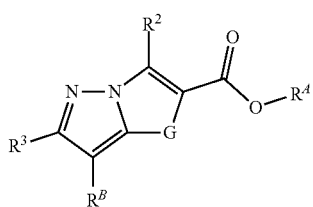

(V-INT)

wherein G is as defined for the compound of general formula (I) and (II) supra, or when G=S of the general formula (VI-INT):

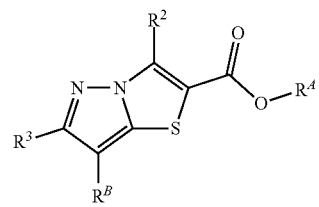

(VI-INT)

wherein in the formulae (V-INT) and (VI-INT) supra $R^2$ is selected from the group consisting of $C_1$-$C_6$-alkyl and $C_3$-$C_6$-cycloalkyl or as defined for the compound of general formula (I) and (II) supra, $R^3$ is selected from the group consisting of hydrogen, halogen, $C_1$-$C_4$-alkyl and $C_3$-$C_6$-cycloalkyl or as defined for the compound of general formula (I) and (II) supra, $R^A$ is H or $C_1$-$C_4$-alkyl, and $R^B$ is H or halogen, and stereoisomers, tautomers, N-oxides, hydrates, solvates, and salts thereof, and mixtures of same.

Particularly, the invention covers also the intermediate compounds of general formula (VI-INT) supra, in which $R^2$ is selected from the group consisting of $C_1$-$C_6$-alkyl and $C_3$-$C_6$-cycloalkyl or as defined for the compound of general formula (I) and (II) supra, $R^3$ is selected from the group consisting of hydrogen, halogen, $C_1$-$C_4$-alkyl and $C_3$-$C_6$-cycloalkyl or as defined for the compound of general formula (I) and (II) supra, $R^A$ is H or $C_1$-$C_4$-alkyl, and $R^B$ is H or halogen, and stereoisomers, tautomers, N-oxides, hydrates, solvates, and salts thereof, and mixtures of same.

Very particularly, the invention covers also the following intermediate compounds and stereoisomers, tautomers, N-oxides, hydrates, solvates, and salts thereof, and mixtures of the same:

Intermediate of formula (VI-INT-1):

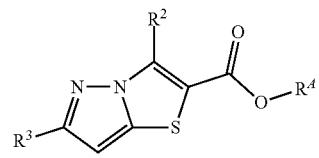

(VI-INT-1)

in which $R^A$ is selected from the group consisting of methyl, ethyl and t-butyl, $R^2$ is selected is selected from the group consisting of $C_1$-$C_6$-alkyl and $C_3$-$C_6$-cycloalkyl, and $R^3$ is selected from the group consisting of hydrogen, halogen, $C_1$-$C_4$-alkyl and $C_3$-$C_6$-cycloalkyl.

Intermediate of formula (VI-INT-2):

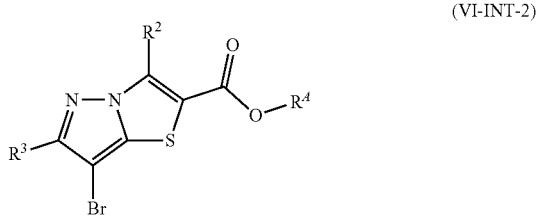

(VI-INT-2)

in which
$R^A$ is selected from the group consisting of methyl, ethyl and t-butyl,
$R^2$ is selected is selected from the group consisting of $C_1$-$C_6$-alkyl and $C_3$-$C_6$-cycloalkyl, and
$R^3$ is selected from the group consisting of hydrogen, halogen, $C_1$-$C_4$-alkyl and $C_3$-$C_6$-cycloalkyl.

Intermediate of formula (VI-INT-3):

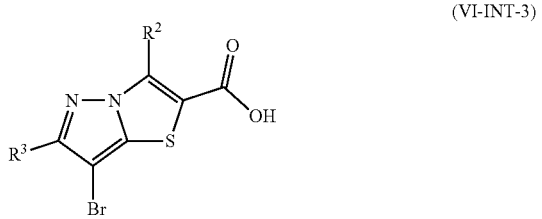

(VI-INT-3)

in which
$R^2$ is selected is selected from the group consisting of $C_1$-$C_6$-alkyl and $C_3$-$C_6$-cycloalkyl, and
$R^3$ is selected from the group consisting of hydrogen, halogen, $C_1$-$C_4$-alkyl and $C_3$-$C_6$-cycloalkyl.

Intermediate of formula (IV-INT-1):

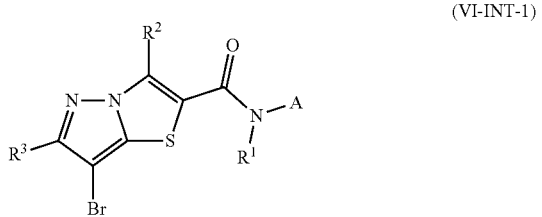

(VI-INT-1)

in which
$R^2$ is selected is selected from the group consisting of $C_1$-$C_6$-alkyl and $C_3$-$C_6$-cycloalkyl,
$R^3$ is selected from the group consisting of hydrogen, halogen, $C_1$-$C_4$-alkyl and $C_3$-$C_6$-cycloalkyl, and
A and $R^1$ are as defined supra.

In accordance with a fifth aspect, the present invention covers the use of said intermediate compounds for the preparation of a compound of general formula (I) and (II) as defined supra.

Particularly, the invention covers the use of intermediate compounds of the general formulae (II-INT), (IV-INT) and (VI-INT) supra, more particularly of the general formulae (VI-INT-1), (VI-INT-2), (VI-INT-3) and (IV-INT-1) supra for the preparation of a compound of general formula (I) and (II) as defined supra.

The present invention covers the intermediate compounds which are disclosed in the Example Section of this text, infra.

The compounds of general formula (I) and (II) of the present invention can be converted to any salt, preferably pharmaceutically acceptable salts, as described herein, by any method which is known to the person skilled in the art. Similarly, any salt of a compound of general formula (I) and (II) of the present invention can be converted into the free compound, by any method which is known to the person skilled in the art.

Compounds of general formula (I) and (II) of the present invention demonstrate a valuable pharmacological spectrum of action, which could not have been predicted. Compounds of the present invention have surprisingly been found to effectively interact with Slo-1 and it is possible therefore that said compounds be used for the treatment or prevention of diseases, preferably helminthic infections, particularly of gastro-intestinal and extra-intestinal helminth infections, more particularly of gastro-intestinal and extra-intestinal infections with nematodes in humans and animals.

Compounds of the present invention can be utilized to control, treat and/or prevent helminth infections, in particular gastro-intestinal and extra-intestinal helminth infections. This method comprises administering to a mammal in need thereof an amount of a compound of this invention, or a pharmaceutically acceptable salt, isomer, polymorph, metabolite, hydrate, solvate or ester thereof; which is effective to treat the disorder.

In an alternative aspect, this method comprises administering to birds, namely cage birds or in particular poultry, in need thereof an amount of a compound of this invention, or a pharmaceutically acceptable salt, isomer, polymorph, metabolite, hydrate, solvate or ester thereof; which is effective to treat the disorder.

Specifically in the field of veterinary medicine, compounds of the present invention are suitable, with favourable toxicity in warm blooded animals, for controlling parasites, in particular helminths, which occur in animal breeding and animal husbandry in livestock, breeding, zoo, laboratory, experimental and domestic animals. They are active against all or specific stages of development of the parasites, in particular of the helminths.

Agricultural livestock include, for example, mammals, such as, sheep, goats, horses, donkeys, camels, buffaloes, rabbits, reindeers, fallow deer, and in particular cattle and pigs; or poultry, such as turkeys, ducks, geese, and in particular chickens; or fish or crustaceans, e.g. in aquaculture or, as the case may be, insects such as bees.

Domestic animals include, for example, mammals, such as hamsters, guinea pigs, rats, mice, chinchillas, ferrets or in particular dogs, cats; cage birds; reptiles; amphibians or aquarium fish.

The present invention also provides methods of treating helminth infections, particularly gastro-intestinal and extra-intestinal helminth infections, more particularly gastro-intestinal and extra-intestinal infections with nematodes.

These disorders have been well characterized in animals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a nematode infection. In particular, and particularly in the animal health or veterinary field, the term "treating" or "treatment" includes prophylactic, metaphylactic or therapeutical treatment Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

The compounds of the present invention can be used in particular in therapy and prevention, i.e. prophylaxis, of helminth infections, particularly gastro-intestinal and extra-intestinal helminth infections, more particularly gastro-intestinal and extra-intestinal infections with nematodes.

By using the compounds of the present invention to control animal parasites, in particular helminths, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the present invention are effective in reducing the incidence of the respective parasite in an animal infected with such parasites to innocuous levels. More specifically, "controlling", as used herein, means that the compounds of the present invention are effective in killing the respective parasite, inhibiting its growth, or inhibiting its proliferation.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prevention of diseases, in particular of helminth infections, particularly of gastro-intestinal and extra-intestinal helminth infections, more particularly of gastro-intestinal and extra-intestinal infections with nematodes.

The pharmaceutical activity of the compounds according to the invention can be explained by their interaction with the Slo-1 ion channel.

In accordance with a further aspect, the present invention covers the use of compounds of general formula (I) and (II), as described supra, or stereoisomers, tautomers, N-oxides, hydrates, solvates, and salts thereof, particularly pharmaceutically acceptable salts thereof, or mixtures of same, for the treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers the use of compounds of general formula (I) and (II), as described supra, or stereoisomers, tautomers, N-oxides, hydrates, solvates, and salts thereof, particularly pharmaceutically acceptable salts thereof, or mixtures of same, in a method of treatment or prevention of diseases, in particular of helminth infections, particularly of gastro-intestinal and extra-intestinal helminth infections, more particularly of gastro-intestinal and extra-intestinal infections with nematodes.

In accordance with a further aspect, the present invention covers use of a compound of general formula (I) and (II), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prevention or treatment of diseases, in particular of helminth infections, particularly of gastro-intestinal and extra-intestinal helminth infections, more particularly of gastro-intestinal and extra-intestinal infections with nematodes.

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using an effective amount of a compound of general formula (I) and (II), as described supra, or stereoisomers, tautomers, N-oxides, hydrates, solvates, and salts thereof, particularly pharmaceutically acceptable salts thereof, or mixtures of same.

In accordance with a further aspect, the present invention covers compounds of general formula (I) and (II), as described supra, or stereoisomers, tautomers, N-oxides, hydrates, solvates, and salts thereof, particularly pharmaceutically acceptable salts thereof, or mixtures of same, for use as an antiendoparasitical agent.

In accordance with a further aspect, the present invention covers compounds of general formula (I) and (II), as described supra, or stereoisomers, tautomers, N-oxides, hydrates, solvates, and salts thereof, particularly pharmaceutically acceptable salts thereof, or mixtures of same, for use as a anthelmintic agent, in particular for use as a nematicidal agent, a platyhelminthicidal agent, an acanthocephalicidal agent, or a pentastomicidal agent.

In accordance with a further aspect, the present invention covers pharmaceutical compositions, in particular a veterinary formulation, comprising a compound of general formula (I) and (II), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

In accordance with a further aspect, the present invention covers a method for preparing a pharmaceutical composition, in particular a veterinary formulation, comprising the step of mixing a compound of general formula (I) and (II), as described supra, or a stereoisomer, a tautomer, an N-oxide, a hydrate, a solvate, a salt thereof, particularly a pharmaceutically acceptable salt, or a mixture of same, with one or more excipients), in particular one or more pharmaceutically acceptable excipient(s).

In accordance with a further aspect, the present invention covers a method of treatment or prevention of diseases, in particular of helminth infections, particularly of gastro-intestinal and extra-intestinal helminth infections, more particularly of gastro-intestinal and extra-intestinal infections with nematodes, using a pharmaceutical composition, in particular a veterinary formulation, comprising an effective amount of a compound of general formula (I) and (II), as described supra, or stereoisomers, tautomers, N-oxides, hydrates, solvates, and salts thereof, particularly pharmaceutically acceptable salts thereof, or mixtures of same.

The present invention furthermore covers pharmaceutical compositions, in particular veterinary formulations, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent. Such administration can be carried out prophylactically, methaphylactically or therapeutically.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, chewables (for example soft chewables), powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, spot-ons, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prevention of an endo- and/or ectoparasiticidal infection.

The term "endoparasite" in the present invention is used as known to persons skilled in the art, and refers in particular to helminths. The term "ectoparasite" in the present invention is used as known to persons skilled in the art, and refers in particular to arthropods, particularly insects or acarids.

Particularly, the present invention covers a pharmaceutical combination, in particular a veterinary combination, which comprises:
one or more first active ingredients, in particular compounds of general formula (I) as defined supra, and
one or more further active ingredients, in particular one or more endo- and/or ectoparasiticides.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known ectoparasiticides and/or endoparasiticides.

The other or further active ingredients specified herein by their common names are known and described, for example, in the Pesticide Manual ("The Pesticide Manual" 16th Ed., British Crop Protection Council 2012) or can be searched in the internet (e.g. http://www.alanwood.net/pesticides). The classification is based on the current IRAC Mode of Action Classification Scheme at the time of filing of this patent application.

Examples of ectoparasiticides and/or endoparasiticides are insecticides, acaricides and nematicides, and include in particular:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(9) Modulators of Chordotonal Organs, such as, for example pymetrozine or flonicamid.

(10) Mite growth inhibitors, such as, for example clofentezine, hexythiazox and diflovidazin or etoxazole.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active ingredients such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoro ethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4- chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6) N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)—N-[3-chloro-1-(3-pyridinyl)-1H-pyrazol-4-yl]-N-ethyl-3-[(3,3,3-trifluoropropyl)sulfinyl]-propanamide and (−)—N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl) sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2 (Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4 aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Active ingredients with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Active ingredients from other classes, e.g. butacarb, dimetilan, cloethocarb, phosphocarb, pirimiphos (-ethyl), parathion (-ethyl), methacrifos, isopropyl o-salicylate, trichlorfon, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos;

organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs);

neonicotinoids, e.g. nithiazine;

dicloromezotiaz, triflumezopyrim;

macrocyclic lactones, e.g. nemadectin, ivermectin, latidectin, moxidectin, selamectin, eprinomectin, doramectin, emamectin benzoate; milbemycin oxime;

triprene, epofenonane, diofenolan;

Biologicals, hormones or pheromones, for example natural products, e.g. thuringiensin, codlemone or neem components;

dinitrophenols, e.g. dinocap, dinobuton, binapacryl;

benzoylureas, e.g. fluazuron, penfluron;

amidine derivatives, e.g. chlormebuform, cymiazole, demiditraz;

Bee hive varroa acaricides, for example organic acids, e.g. formic acid, oxalic acid.

Non-limiting examples of insecticides and acaricides of particular interest for use in animal health are and include in particular [i.e. Mehlhorn et al Encyclpaedic Reference of Parasitology 4$^{th}$ edition (ISBN 978-3-662-43978-4)]:

Effectors at arthropod ligand gated chloride channels: chlordane, heptachlor, endoculfan. Dieldrin, bromocyclen, toxaphene, lindane, fipronil, pyriprole, sisapronil, afoxolaner, fluralaner, sarolaner, lotilaner, fluxametamide, broflanilide, avermectin, doramectin, eprinomectin, ivermectin, milbemycin, moxidectin, selamectin;

Modulators of arthropod octopaminergic receptors: amitraz, BTS27271, cymiazole, demiditraz;

Effectors at arthropod voltage-gated sodium channels: DDT, methoxychlor, metaflumizone, indoxacarb, cinerin I, cinerin II, jasmolin I, jasmolin II, pyrethrin I, pyrethrin II, allethrin, alphacypermethrin, bioallethrin, betacyfluthrin, cyfluthrin, cyhalothrin, cypermethrin, deltamethrin, etofenprox, fenvalerate, flucythrinate, flumethrin, halfenprox, permethrin, phenothrin, resmethrin, tau-fluvalinate, tetramethrin;

Effectors at arthropod nicotinic cholinergic synapses (acetylcholine esterase, acetylcholine receptors): bromoprypylate, bendiocarb, carbaryl, methomyl, promacyl, propoxur, azamethiphos, chlorfenvinphos, chlorpyrifos, coumaphos, cythioate, diazinon, diclorvos, dicrotophos, dimethoate, ethion, famphur, fenitrothion, fenthion, heptenophos, malathion, naled, phosmet, phoxim, phtalofos, propetamphos, temephos, tetrachlorvinphos, trichlorfon, imidacloprid, nitenpyram, dinotefuran, spinosad, spinetoram;

Effectors on arthropod development processes: cyromazine, dicyclanil, diflubenzuron, fluazuron, lufenuron, triflumuron, fenoxycarb, hydroprene, methoprene, pyriproxyfen, fenoxycarb, hydroprene, S-methoprene, pyriproxyfen.

Exemplary active ingredients from the group of endoparasiticides, as a further or other active ingredient in the present invention, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active ingredients in the present invention, including, without limitation, the following active ingredients:

from the class of triazines, for example: diclazuril, ponazuril, letrazuril, toltrazuril;

from the class of polyether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis, Dictyocaulus viviparus.*

All named other or further active ingredients in the present invention can, if their functional groups enable this, optionally form salts with suitable bases or acids.

Based upon standard laboratory techniques known to evaluate compounds useful for the treatment of helminth infections, by standard toxicity tests and by standard pharmacological assays for the determination of treatment of the conditions identified above in animals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the subject treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a subject is not dosed with a drug for a certain period of time, to be beneficial to the overall balance between pharmacological effect and tolerability. Furthermore, it is possible to have long-acting treatments, wherein the subject gets treated once for more than four weeks. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each subject will vary according to the nature and severity of the condition as determined by the attending diagnostician, the activity of the specific compound employed, the age and general condition of the subject, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Experimental Section

Abbreviations:

| aq. | aqueous |
|---|---|
| DMF | dimethylformamide |
| DMSO | dimethylsulfoxide |
| MTBE | methyl-t.-butylether |
| THF | tetrahydrofurane |

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or dichloromethane/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical and Chromatography Methods

Analytical and preparative Liquid Chromatography

Analytical (UP)LC-MS was performed by means of different equipments as described below. The masses (m/z) are reported from the positive mode electrospray ionisation unless the negative mode is indicated (ESI−).

Method L0:

Instrument type: Waters UPLC system; column: Zorbax Eclipse Plus C18, 50 mm×2.1 mm, 1.8 µm; eluent A: acetonitrile+1 ml formic acid/L, eluent B: millipore water+0.9 ml formic acid/L; gradient: 0.0 min 10% A→1.7 min 95% A→2.40 min 95% A→2.41 min 10% A→2.5 min 10% A; oven: 55° C.; flow: 0.85 ml/min; UV-detection: 210 nm. Waters SQD2 MS detector: 100-1000 Amu, ES-ionization, positive.

$^1$H-NMR Data $^1$H-NMR data were determined with a Bruker Avance 400 (equipped with a flow cell (60 µl volume), or with a Bruker AVIII 400 equipped with 1.7 mm cryo CPTCI probe head, or with a Bruker AVIII 400 (400.13 MHz) equipped with a 5 mm probe head, or with a Bruker AVII 600 (600.13 MHz) equipped with a 5 mm cryo TCI probe head, or with a Bruker AVIII 600 (601.6 MHz) equipped with a 5 mm cryo CPMNP probe head, or with a Bruker AVIII 500 (500.13 MHz) equipped with a 5 mm broadband head or a 5 mm Prodigy™ probe head, with tetramethylsilane as reference (0.0) and the solvents CD$_3$CN, CDCl$_3$ or D$_6$-DMSO. Alternative $^1$H- and $^{13}$C-NMR instrument types: Bruker DMX300 ($^1$H NMR: 300 MHz; $^{13}$C NMR: 75 MHz), Bruker Avance III 400 ($^1$H NMR: 400 MHz; $^{13}$C NMR: 100 MHz) or Bruker 400 Ultrashield ($^1$H NMR: 400 MHz; $^{13}$C NMR: 100 MHz).

Chemical shifts (δ) are displayed in parts per million [ppm]; the following abbreviations are used: s=singlet, d=doublet, t=triplet, q=quartet, m=multiplet, br.=broad; coupling constants are displayed in Hertz [Hz].

Experimental Section—General Procedures

The synthesis of the compounds of the formula (I) and (II) can be performed according to or in analogy to the following scheme 1.

Scheme 1

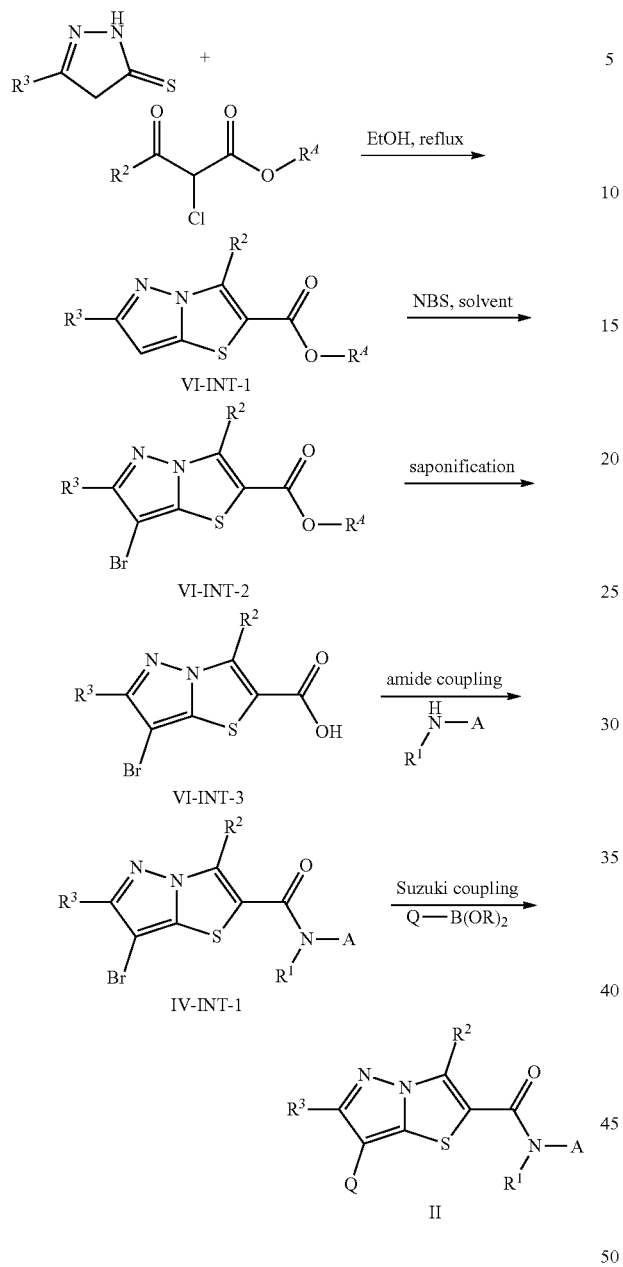

wherein the substituents have the meaning as defined for the intermediate compounds supra, such as in particular for intermediate compound (VI-INT) and (IV-INT) supra, very particularly for intermediate compounds (VI-INT-1), (VI-INT-2), (VI-INT-3), and (IV-INT-1) supra.

Certain substituted pyrazolothiones can be readily converted with 2-chloro ketoesters (wherein $R^4$ is preferably selected from methyl, ethyl or t-butyl), dissolved in alcohols like ethanol, preferably under boiling conditions, into pyrazolo[5,1-b][1,3]thiazole-2-carboxylates VI-INT-1 as described with analogous systems in US 20040132708, followed by bromination with N-bromosuccinimide in inert solvents like dichloromethane or tetrachlorometane, preferably at ambient temperature, to obtain esters VI-INT-2. Such intermediate esters react under hydrolytic conditions to yield pyrazolo[5,1-b][1,3]thiazole-2-carboxylic acids VI-INT-3 as described with similar syntheses in Journal of Organic Chemistry, 2004, 69(21), 7058-7065. Pyrazolo[5,1-b][1,3]thiazole-2-carboxylic acids VI-INT-3 can be converted into the corresponding amides IV-INT-1 by amide coupling conditions, e.g. via carboxylic acid chlorides formed from VI-INT-3, which are combined with amines $R^1$—NH-A under basic conditions, e.g. pyridine, triethylamine or N,N-diisopropyl ethylamine or via amide formation from the carboxylic acids VI-INT-3 which are combined with amines $R^1$—NH-A and dehydration reagents, e.g. N-(3-dimethyl-aminoisopropyl)-N'-ethylcarbodiimide-hydrochloride (EDC). Similar syntheses are described in WO 2001016138 for example.

Pyrazolo[5,1-b][1,3]thiazole-2-carboxylic amides IV-INT-1 can be converted via a Suzuki cross coupling reaction with boronic acids or boronic esters Q-B(OR)$_2$ (R=H; R=methyl or R,R=pinacolate) as described with similar reactions in WO 2015154630, into aryl- or hetaryl-substituted final compounds II.

Experimental Section

EXAMPLES

Example 1

7-(3,5-dichlorophenyl)-N-[(4S)-3,4-dihydro-2H-chromen-4-yl]-3-isopropyl-6-methylpyrazolo[5,1-b][1,3]thiazole-2-carboxamide

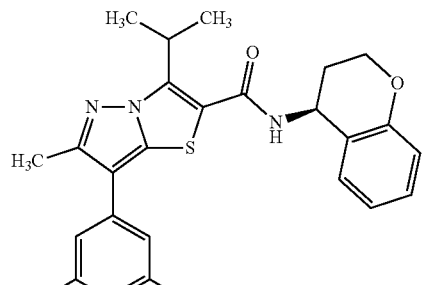

Step 1

5-Methyl-2,4-dihydro-3H-pyrazole-3-thione

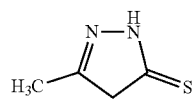

3-Methyl-1H-pyrazol-5-ol (20 g, 200 mmol) was dissolved in toluene (500 mL), then, Lawesson's reagent (42 g, 100 mmol) was added. The resulting mixture was refluxed 9 hours and was left overnight at room temperature. The mixture was concentrated and used without further purification in the next step.

Step 2

Ethyl 3-isopropyl-6-methylpyrazolo[5,1-b][1,3]thiazole-2-carboxylate

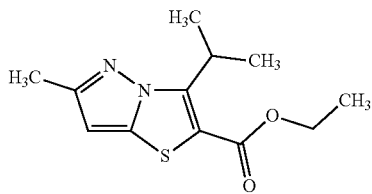 [SMILES: CCOC(=O)c1sc2cc(C)nn2c1C(C)C]

A mixture of ethyl 2-chloro-4-methyl-3-oxopentanoate (120 g, 600 mmol), known from Bioorganic & Medicinal Chemistry Letters, 2012, 22(20), 6338-6342, and 5-methyl-2,4-dihydro-3H-pyrazole-3-thione (23 g, 200 mmol (theoretically expected)) in ethanol (600 mL) was refluxed for 8 h and then concentrated in vacuo. The residue was treated with water, and the resulting mixture was extracted with ethyl acetate. The combined organic solvents were dried over sodium sulfate and concentrated in vacuo. The remaining oil was purified via a silica gel column (95:5 hexane/ethyl acetate) to obtain the title compound as colourless solid.

Yield: 3.7 g (14.7 mmol; 7.33% of th.)

Step 3

Ethyl 7-bromo-3-isopropyl-6-methylpyrazolo[5,1-b][1,3]thiazole-2-carboxylate

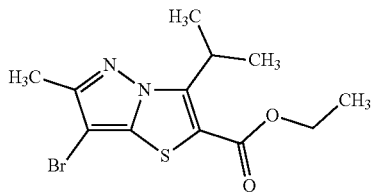 [SMILES: CCOC(=O)c1sc2c(Br)c(C)nn2c1C(C)C]

To a solution of ethyl 3-isopropyl-6-methylpyrazolo[5,1-b][1,3]thiazole-2-carboxylate (3.7 g, 14.7 mmol) in dry carbon tetrachloride (100 mL) was added N-bromosuccinimide (2.9 g, 16 mmol). The resulting mixture was stirred at room temperature for 4 hours. Then, it was diluted with dichloromethane and washed with water, followed by brine. The separated organic layer was dried over sodium sulfate. The product was used in the next step without further purification.

Yield: 4.8 g (14.5 mmol; 98.6% of th.)

Step 4

7-Bromo-3-isopropyl-6-methylpyrazolo[5,1-b][1,3]thiazole-2-carboxylic acid

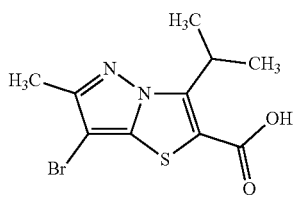 [SMILES: Cc1nn2c(C(C)C)c(C(=O)O)sc2c1Br]

To the solution of ethyl 7-bromo-3-isopropyl-6-methylpyrazolo[5,1-b][1,3]thiazole-2-carboxylate (4.8 g, 14.5 mmol) in EtOH (100 mL), water (100 mL) and THF (50 mL) was added LiOH (1 g, 41.67 mmol). The resulting solution was stirred overnight at room temperature. The mixture was concentrated until the aqueous solution remained, washed three times with dichloromethane and acidified with conc. HCl. The precipitated product was filtered, washed with water and dried.

Yield: 3 g (purity 85%; 8.41 mmol; 58.0% of th.)

LC-MS (Method L0): $R_t$=1.39 min; MS (ESIpos): m/z=302.9; 304.9 [M+H]$^+$.

$^1$H-NMR (399.95) MHz, DMSO-d6) δ[ppm]: 14.00 (bs, 1H, COOH), 4.37 (hept, 1H), 2.33 (s, 1H), 1.44 (d, 6H).

Step 5

7-Bromo-N-[(4S)-3,4-dihydro-2H-chromen-4-yl]-3-isopropyl-6-methylpyrazolo[5,1-b][1,3]thiazole-2-carboxamide

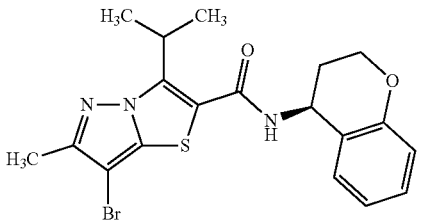 [SMILES: Cc1nn2c(C(C)C)c(C(=O)N[C@H]3CCOc4ccccc43)sc2c1Br]

A flask was charged with 7-bromo-3-isopropyl-6-methylpyrazolo[5,1-b][1,3]thiazole-2-carboxylic acid (3.0 g, 85% purity, 8.41 mmol), (4S)-chroman-4-amine hydrochloride (1.87 g, 10.09 mmol), N,N-diisopropyl ethylamine (2.17 g, 16.82 mmol), 4-(N,N-dimethylamino) pyridine (513.8 mg, 4.21 mmol), 1-hydroxy-1H-benzotriazole (568.3 mg, 4.21 mmol) and 1-ethyl-3-(3-dimethylaminopropyl)carbodiimide hydrochloride (1.61 g, 8.41 mmol) in 125 mL dichloromethane. The reaction mixture was stirred at ambient temperature overnight, then mixed with water, the dichloromethane phase was separated, dried via a sodium sulfate/silica gel cartridge and the solvent was removed under reduced pressure. The residue was purified by silica gel column chromatography (eluent cyclohexane/ethyl acetate gradient) to obtain the title compound.

Yield: 2.0 g (4.6 mmol, 54.7% of th.)

LC-MS (Method L0): $R_t$=1.70 min; MS (ESIpos): m/z=434.0; 435.9 [M+H]$^+$.

$^1$H-NMR (399.95) MHz, DMSO-d6) δ [ppm]: 8.91 (d, 1H, NH), 7.20-7.15 (m, 2H), 6.92-6.89 (dd, 1H), 6.81 (d, 1H), 5.24-5.19 (m, 1H), 4.30-4.20 (m, 2H), 4.09-4.02 (hept, 1H), 2.32 (s, 3H), 2.16-2.05 (m, 2H), 1.47 (d, 6H).

Step 6

7-(3,5-Dichlorophenyl)-N-[(4S)-3,4-dihydro-2H-chromen-4-yl]-3-isopropyl-6-methyl-pyrazolo[5,1-b][1,3]thiazole-2-carboxamide

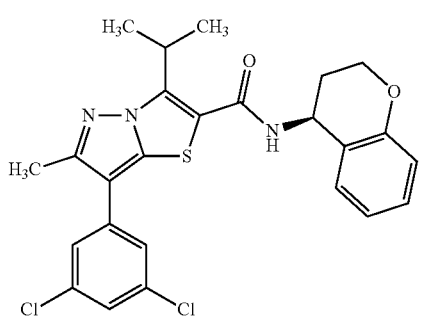 [SMILES: Cc1nn2c(C(C)C)c(C(=O)N[C@H]3CCOc4ccccc43)sc2c1-c1cc(Cl)cc(Cl)c1]

A microwave tube was charged with 3 mL dioxane, 7-bromo-N-[(4S)-3,4-dihydro-2H-chromen-4-yl]-3-isopropyl-6-methylpyrazolo[5,1-b][1,3]thiazole-2-carboxamide (150 mg, 0.34 mmol), 3,5-dichlorophenyl boronic acid (54.9 mg, 0.28 mmol), aqueous 2M sodium carbonate solution (1.44 mL) and (1,1'-bis(diphenylphosphino)-ferrocene-palladium-dichloromethane complex (21 mg, 0.02 mmol). The reaction mixture was degassed with argon for 5 min and was treated in a microwave device (Biotage) for 40 min at 100° C. The crude mixture was filtered and washed through a silica gel/sodium sulfate cartridge. The solvents of the filtrate were evaporated under reduced pressure; the remaining raw material was purified by flash column chromatography using a cyclohexane/ethyl acetate gradient to obtain the title compound as an off-white solid.

Yield: 92.6 mg (0.185 mmol, 66.1% of th. regarding the boronic acid)

LC-MS (Method L0): $R_t$=1.93 min; MS (ESIpos): m/z=500.0; 501.9 [M+H]$^+$.

$^1$H-NMR (399.95) MHz, DMSO-d6) δ [ppm]: 8.92 (d, 1H, NH), 7.53 (s, 1H), 7.46 (s, 2H), 7.21-7.15 (m, 2H), 6.91 (t, 1H), 6.81 (d, 1H), 5.26-5.21 (q, 1H), 4.32-4.19 (m, 3H), 2.56 (s, 3H), 2.12-2.06 (m, 2H), 1.51 (d, 6H).

The following examples 2-15 were prepared analogously:

Example 2

7-(2,3-dichlorophenyl)-N-[(4S)-3,4-dihydro-2H-chromen-4-yl]-6-methyl-3-(propan-2-yl)pyrazolo[5,1-b][1,3]thiazole-2-carboxamide

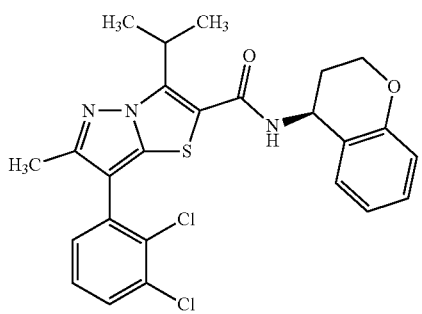 [SMILES: Cc1nn2c(C(C)C)c(C(=O)N[C@H]3CCOc4ccccc43)sc2c1-c1cccc(Cl)c1Cl]

LC-MS (Method L0): $R_t$=1.77 min; MS (ESIpos): m/z=500.0; 502.0 [M+H]$^+$.

$^1$H-NMR see NMR peak list table 1.

Example 3

7-[2-fluoro-3-(trifluoromethyl)phenyl]-N-[(4S)-3,4-dihydro-2H-chromen-4-yl]-6-methyl-3-(propan-2-yl)pyrazolo[5,1-b][1,3]thiazole-2-carboxamide

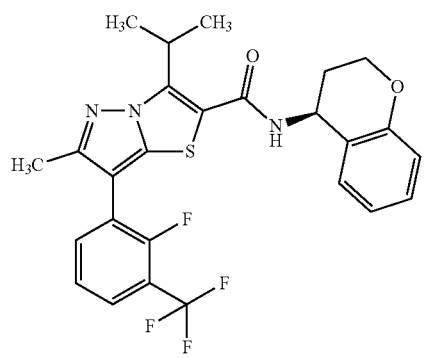

LC-MS (Method L0): $R_t$=1.82 min; MS (ESIpos): m/z=518.1 [M+H]$^+$.

$^1$H-NMR see NMR peak list table 1.

Example 4

N-[(4S)-3,4-dihydro-2H-chromen-4-yl]-7-[2-fluoro-3-(trifluoromethoxy)phenyl]-3-isopropyl-6-methylpyrazolo[5,1-b][1,3]thiazole-2-carboxamide

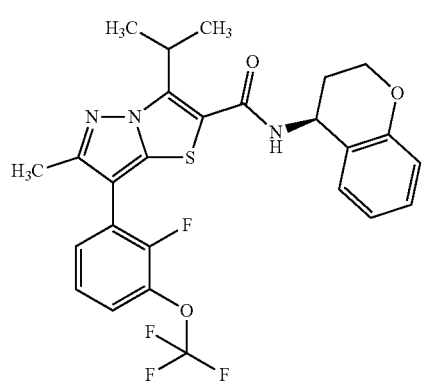 [SMILES: Cc1nn2c(C(C)C)c(C(=O)N[C@H]3CCOc4ccccc43)sc2c1-c1cccc(OC(F)(F)F)c1F]

LC-MS (Method L0): $R_t$=1.79 min; MS (ESIpos): m/z=534.0 [M+H]$^+$.

$^1$H-NMR see NMR peak list table 1.

Example 5

7-(3,5-dichloro-4-fluorophenyl)-N-[(4S)-3,4-dihydro-2H-chromen-4-yl]-3-isopropyl-6-methylpyrazolo[5,1-b][1,3]thiazole-2-carboxamide

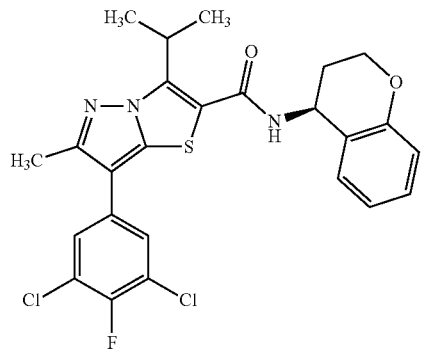 [SMILES: Cc1nn2c(C(C)C)c(C(=O)N[C@H]3CCOc4ccccc43)sc2c1-c1cc(Cl)c(F)c(Cl)c1]

LC-MS (Method L0): $R_t$=1.80 min; MS (ESIpos): m/z=518.2 [M+H]$^+$.

$^1$H-NMR see NMR peak list table 1.

Example 6

N-[(4S)-3,4-dihydro-2H-chromen-4-yl]-7-[3-(dimethylamino)-2,4-difluorophenyl]-6-methyl-3-(propan-2-yl)pyrazolo[5,1-b][1,3]thiazole-2-carboxamide

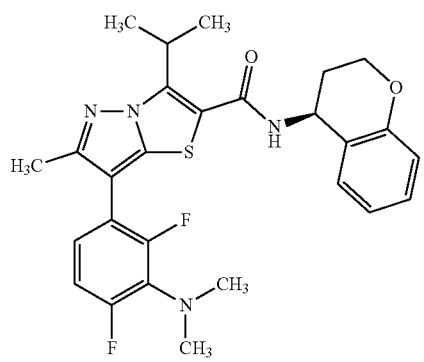

LC-MS (Method L0): $R_t$=1.83 min; MS (ESIpos): m/z=511.2 [M+H]$^+$.

$^1$H-NMR see NMR peak list table 1.

Example 7

7-(3,4-dichlorophenyl)-N-[(4S)-3,4-dihydro-2H-chromen-4-yl]-6-methyl-3-(propan-2-yl)pyrazolo[5,1-b][1,3]thiazole-2-carboxamide

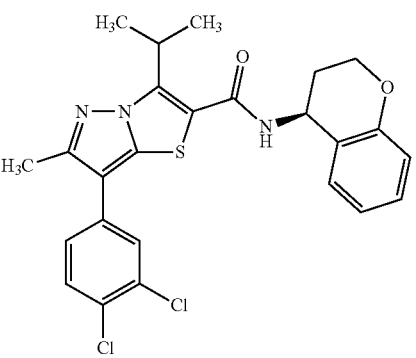

LC-MS (Method L0): $R_t$=1.89 min; MS (ESIpos): m/z=500.0; 501.9 [M+H]$^+$.

$^1$H-NMR see NMR peak list table 1.

Example 8

7-(3,4-difluorophenyl)-N-[(4S)-3,4-dihydro-2H-chromen-4-yl]-6-methyl-3-(propan-2-yl)pyrazolo[5,1-b][1,3]thiazole-2-carboxamide

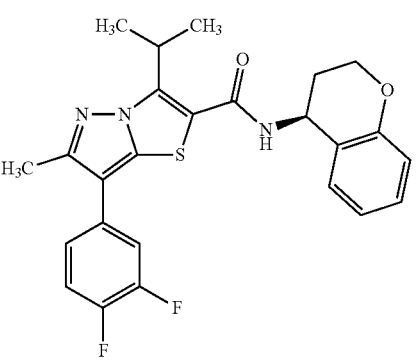 [SMILES: Cc1nn2c(C(C)C)c(C(=O)N[C@H]3CCOc4ccccc43)sc2c1-c1ccc(Cl)c(Cl)c1]

LC-MS (Method L0): $R_t$=1.63 min; MS (ESIpos): m/z=468.3 [M+H]$^+$.

$^1$H-NMR see NMR peak list table 1.

Example 9

N-[(4S)-3,4-dihydro-2H-chromen-4-yl]-6-methyl-3-(propan-2-yl)-7-(2,3,4-trifluorophenyl)pyrazolo[5,1-b][1,3]thiazole-2-carboxamide

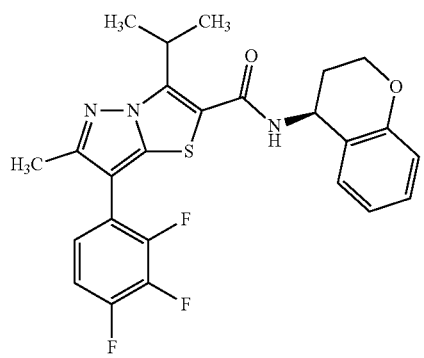 [SMILES: Cc1nn2c(C(C)C)c(C(=O)N[C@H]3CCOc4ccccc43)sc2c1-c1ccc(F)c(F)c1F]

LC-MS (Method L0): $R_t$=1.63 min; MS (ESIpos): m/z=486.3 [M+H]$^+$.

$^1$H-NMR see NMR peak list table 1.

Example 10

7-(2,6-dichlorophenyl)-N-[(4S)-3,4-dihydro-2H-chromen-4-yl]-6-methyl-3-(propan-2-yl)pyrazolo[5,1-b][1,3]thiazole-2-carboxamide

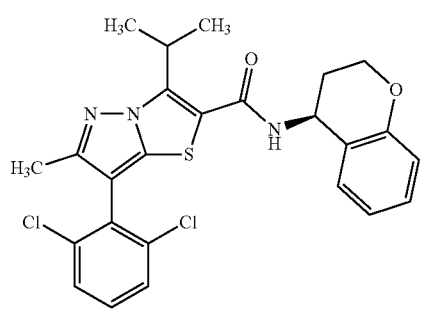 [SMILES: Cc1nn2c(C(C)C)c(C(=O)N[C@H]3CCOc4ccccc43)sc2c1-c1c(Cl)cccc1Cl]

LC-MS (Method L0): $R_t$=1.71 min; MS (ESIpos): m/z=500.0; 501.9 [M+H]$^+$.

$^1$H-NMR see NMR peak list table 1.

Example 11

7-[2-chloro-3-(trifluoromethyl)phenyl]-N-[(4S)-3,4-dihydro-2H-chromen-4-yl]-6-methyl-3-(propan-2-yl)pyrazolo[5,1-b][1,3]thiazole-2-carboxamide

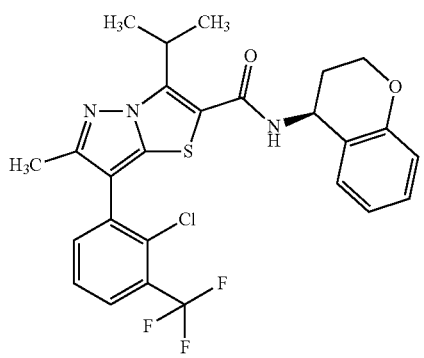 [SMILES: Cc1nn2c(C(C)C)c(C(=O)N[C@H]3CCOc4ccccc43)sc2c1-c1cccc(C(F)(F)F)c1Cl]

LC-MS (Method L0): $R_t$=1.67 min; MS (ESIpos): m/z=534.3 [M+H]$^+$.

$^1$H-NMR see NMR peak list table 1.

Example 12

N-[(4S)-3,4-dihydro-2H-chromen-4-yl]-6-methyl-3-(propan-2-yl)-7-(2,3,5-trichlorophenyl)pyrazolo[5,1-b][1,3]thiazole-2-carboxamide

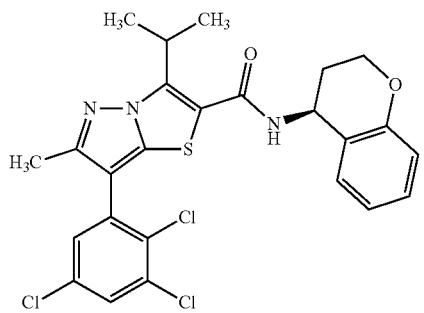 [SMILES: Cc1nn2c(C(C)C)c(C(=O)N[C@H]3CCOc4ccccc43)sc2c1-c1cc(Cl)cc(Cl)c1Cl]

LC-MS (Method L0): $R_t$=1.79 min; MS (ESIpos): m/z=536.2 [M+H]$^+$.

$^1$H-NMR see NMR peak list table 1.

Example 13

N-[(4S)-3,4-dihydro-2H-chromen-4-yl]-7-[3-(dimethylamino)-2-fluorophenyl]-6-methyl-3-(propan-2-yl)pyrazolo[5,1-b][1,3]thiazole-2-carboxamide

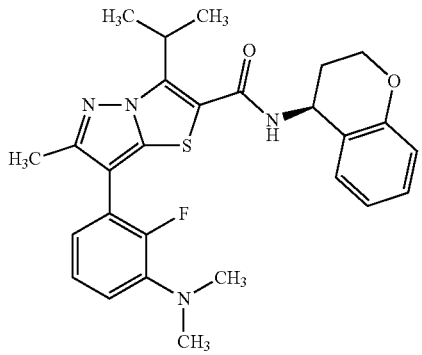 [SMILES: Cc1nn2c(C(C)C)c(C(=O)N[C@H]3CCOc4ccccc43)sc2c1-c1cccc(N(C)C)c1F]

LC-MS (Method L0): $R_t$=1.62 min; MS (ESIpos): m/z=493.3 [M+H]$^+$.
$^1$H-NMR see NMR peak list table 1.

Example 14

7-(3,5-dichloro-4-fluorophenyl)-N-[(1S)-2,3-dihydro-1H-inden-1-yl]-6-methyl-3-(propan-2-yl)pyrazolo[5,1-b][1,3]thiazole-2-carboxamide

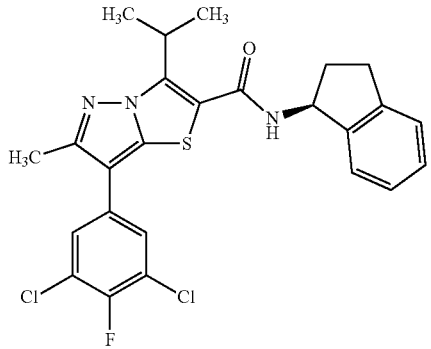 [SMILES: Cc1nn2c(C(C)C)c(C(=O)N[C@H]3CCc4ccccc43)sc2c1-c1cc(Cl)c(F)c(Cl)c1]

LC-MS (Method L0): $R_t$=1.96 min; MS (ESIpos): m/z=502.1; 504.1 [M+H]$^+$.
$^1$H-NMR see NMR peak list table 1.

Example 15

7-(2,3-dichlorophenyl)-N-[(1S)-2,3-dihydro-1H-inden-1-yl]-6-methyl-3-(propan-2-yl)pyrazolo[5,1-b][1,3]thiazole-2-carboxamide

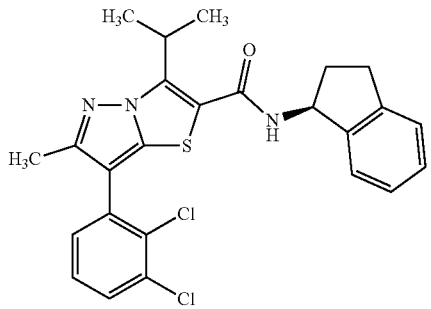 [SMILES: Cc1nn2c(C(C)C)c(C(=O)N[C@H]3CCc4ccccc43)sc2c1-c1cccc(Cl)c1Cl]

LC-MS (Method L0): $R_t$=1.89 min; MS (ESIpos): m/z=484.1; 486.1 [M+H]$^+$.
$^1$H-NMR see NMR peak list table 1.

NMR Peak Lists $^1$H-NMR data of selected examples are written in form of $^1$H-NMR-peak lists. To each signal peak are listed the δ-value in ppm and the signal intensity in round brackets. Between the δ-value—signal intensity pairs are semicolons as delimiters.

The peak list of an example has therefore the form:

$δ_1$ (intensity$_1$); $δ_2$ (intensity$_2$); ... ; $δ_i$ (intensity$_i$); ... ; $δ_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

TABLE 1

NMR Peaklist

Example 1: ¹H-NMR(400.0 MHz, d₆-DMSO):
δ = 8.924(2.5); 8.904(2.5); 8.312(0.7); 7.529(2.6); 7.525(5.2); 7.520(3.5); 7.460(10.6); 7.456(10.1); 7.210(2.3); 7.191(3.8); 7.171(2.3); 7.153(1.4); 6.926(1.7); 6.907(2.8); 6.888(1.3); 6.810(3.1); 6.791(2.8); 5.258(0.6); 5.242(1.5); 5.223(1.5); 5.207(0.6); 4.316(0.4); 4.308(0.6); 4.299(0.5); 4.289(1.4); 4.280(1.2); 4.272(1.3); 4.261(1.2); 4.252(1.3); 4.240(2.1); 4.223(2.8); 4.205(1.8); 4.187(0.5); 3.320(470.7); 2.670(1.6); 2.555(19.6); 2.505(204.0); 2.501(276.3); 2.498(221.3); 2.328(1.6); 2.115(1.5); 2.107(1.4); 2.097(1.6); 2.088(1.3); 2.070(0.8); 2.053(0.4); 1.506(16.0); 1.489(16.0); 0.000(13.9)

Example 2: ¹H-NMR(400.0 MHz, d₆-DMSO):
δ = 8.864(2.0); 8.843(2.1); 8.313(0.4); 8.141(0.5); 7.689(2.2); 7.669(2.5); 7.535(1.8); 7.516(3.0); 7.463(2.2); 7.443(3.0); 7.423(1.2); 7.195(2.2); 7.176(3.2); 7.161(2.2); 7.141(1.3); 6.912(1.5); 6.894(2.5); 6.875(1.2); 6.799(2.8); 6.779(2.5); 5.240(0.6); 5.223(1.4); 5.206(1.3); 5.190(0.6); 4.292(0.5); 4.273(1.3); 4.263(1.2); 4.255(1.3); 4.246(1.6); 4.237(1.3); 4.226(1.2); 4.216(1.3); 4.198(0.5); 4.174(0.4); 4.156(1.1); 4.138(1.4); 4.121(1.1); 4.102(0.4); 3.318(160.2); 2.670(1.4); 2.540(1.4); 2.501(227.1); 2.337(16.0); 2.115(1.1); 2.110(1.0); 2.092(1.0); 2.073(3.7); 2.048(0.7); 1.520(10.6); 1.505(10.6); 1.502(10.4); 0.000(1.4)

Example 3: ¹H-NMR(400.0 MHz, d₆-DMSO):
δ = 8.916(2.0); 8.896(2.0); 7.958(1.0); 7.940(1.9); 7.922(1.0); 7.779(0.9); 7.760(1.9); 7.743(1.1); 7.538(1.4); 7.519(2.4); 7.499(1.1); 7.201(2.0); 7.182(3.2); 7.166(2.1); 7.147(1.3); 6.919(1.5); 6.900(2.5); 6.882(1.2); 6.805(2.7); 6.785(2.5); 5.754(4.1); 5.248(0.6); 5.231(1.3); 5.214(1.3); 5.197(0.6); 4.309(0.4); 4.300(0.6); 4.281(1.3); 4.272(1.0); 4.264(1.2); 4.254(1.0); 4.246(1.0); 4.237(1.2); 4.228(1.4); 4.219(1.5); 4.210(1.5); 4.192(1.9); 4.174(1.1); 4.157(0.4); 3.319(51.9); 2.892(0.8); 2.733(0.7); 2.672(0.4); 2.507(44.2); 2.503(57.1); 2.499(44.2); 2.460(16.0); 2.329(0.4); 2.145(0.4); 2.133(0.7); 2.116(1.1); 2.108(1.4); 2.091(1.3); 2.080(1.1); 2.074(0.8); 2.063(0.7); 2.055(0.5); 1.517(11.4); 1.502(11.1); 1.500(11.1); 0.007(2.8); 0.000(42.3); −0.001(41.9)

Example 4: ¹H-NMR(400.0 MHz, d₆-DMSO):
δ = 8.904(2.1); 8.883(2.1); 7.663(0.9); 7.659(1.1); 7.643(2.0); 7.627(1.2); 7.623(1.2); 7.565(0.8); 7.545(1.6); 7.526(1.0); 7.438(1.5); 7.435(1.6); 7.415(2.4); 7.398(1.0); 7.395(1.0); 7.202(2.0); 7.183(3.1); 7.167(2.0); 7.148(1.3); 7.144(1.1); 6.922(1.4); 6.919(1.6); 6.903(2.4); 6.900(2.6); 6.884(1.1); 6.882(1.2); 6.806(2.7); 6.804(2.7); 6.786(2.5); 6.784(2.4); 5.248(0.5); 5.231(1.2); 5.214(1.2); 5.197(0.5); 4.307(0.4); 4.299(0.6); 4.290(0.4); 4.280(1.3); 4.270(1.1); 4.262(1.2); 4.253(1.1); 4.248(1.1); 4.239(1.1); 4.230(1.0); 4.220(1.4); 4.212(0.5); 4.201(0.9); 4.193(0.5); 4.184(1.2); 4.166(1.6); 4.149(1.2); 4.131(0.4); 3.317(36.2); 2.671(0.4); 2.524(1.1); 2.511(23.9); 2.507(49.5); 2.502(66.4); 2.498(48.9); 2.493(24.2); 2.452(16.0); 2.329(0.4); 2.146(0.4); 2.135(0.7); 2.126(0.8); 2.118(1.0); 2.104(1.1); 2.095(1.1); 2.086(1.0); 2.074(3.5); 2.060(0.7); 2.052(0.5); 2.043(0.3); 1.518(10.6); 1.514(11.0); 1.500(10.7); 1.496(10.7); 0.008(2.0); 0.000(59.3); −0.008(2.4)

Example 5: ¹H-NMR(400.0 MHz, d₆-DMSO):
δ = 8.910(2.0); 8.890(2.0); 8.311(0.4); 7.612(7.2); 7.596(7.1); 7.204(2.3); 7.186(3.2); 7.171(2.3); 7.152(1.4); 6.923(1.6); 6.906(2.7); 6.888(1.2); 6.810(3.0); 6.790(2.7); 5.256(0.6); 5.239(1.4); 5.222(1.4); 5.206(0.6); 4.316(0.4); 4.307(0.6); 4.299(0.5); 4.288(1.4); 4.279(1.2); 4.271(1.2); 4.261(1.1); 4.250(1.3); 4.242(1.4); 4.231(2.1); 4.224(1.8); 4.213(2.0); 4.205(1.0); 4.195(1.5); 4.177(0.5); 3.334(255.5); 3.326(148.8); 2.676(0.7); 2.672(0.9); 2.667(0.7); 2.542(67.6); 2.530(2.4); 2.507(114.1); 2.502(149.8); 2.498(110.9); 2.368(0.4); 2.329(0.9); 2.325(0.7); 2.148(0.4); 2.137(0.8); 2.120(1.2); 2.112(1.5); 2.104(1.3); 2.095(1.5); 2.086(1.2); 2.078(0.8); 2.068(0.7); 2.060(0.5); 2.051(0.3); 1.504(16.0); 1.487(15.9); 0.008(0.5); 0.000(15.2); −0.008(0.6)

Example 6: ¹H-NMR(400.0 MHz, d₆-DMSO):
δ = 8.858(0.4); 8.837(0.4); 7.196(0.5); 7.179(0.6); 7.164(0.4); 6.900(0.4); 6.803(0.5); 6.783(0.5); 3.320(18.1); 2.845(3.9); 2.511(5.2); 2.506(10.7); 2.502(14.8); 2.498(10.9); 2.493(5.2); 2.395(2.7); 1.511(1.7); 1.507(1.7); 1.494(1.8); 1.490(1.7); 1.398(16.0); 1.168(0.7); 0.008(0.4); 0.000(11.1); −0.008(0.4)

Example 7: ¹H-NMR(400.0 MHz, d₆-DMSO):
δ = 8.919(2.8); 8.899(2.8); 7.741(5.9); 7.720(7.0); 7.658(6.3); 7.652(6.7); 7.484(3.7); 7.479(3.5); 7.463(3.2); 7.458(3.2); 7.210(2.6); 7.191(4.2); 7.172(2.6); 7.153(1.7); 7.150(1.5); 6.927(1.9); 6.925(2.1); 6.908(3.2); 6.906(3.4); 6.890(1.5); 6.887(1.6); 6.811(3.5); 6.809(3.5); 6.791(3.3); 6.789(3.2); 5.256(0.7); 5.239(1.6); 5.221(1.6); 5.205(0.7); 4.316(0.5); 4.308(0.7); 4.298(0.5); 4.289(1.7); 4.279(1.3); 4.272(1.5); 4.262(1.2); 4.254(1.2); 4.245(1.4); 4.236(1.3); 4.226(1.8); 4.219(1.1); 4.207(1.0); 4.201(1.9); 4.184(2.1); 4.166(1.6); 4.148(0.6); 3.318(69.9); 2.676(0.4); 2.671(0.5); 2.666(0.4); 2.548(27.2); 2.524(1.4); 2.519(2.0); 2.511(30.0); 2.506(63.1); 2.502(84.9); 2.497(62.7); 2.493(31.2); 2.333(0.4); 2.329(0.5); 2.324(0.6); 2.167(0.4); 2.161(0.9); 2.153(0.5); 2.141(0.9); 2.134(0.9); 2.125(1.3); 2.114(1.5); 2.103(1.3); 2.096(1.3); 2.086(1.4); 2.074(1.4); 2.069(0.9); 2.061(0.6); 2.052(0.4); 2.043(0.3); 1.508(15.6); 1.506(16.0); 1.491(15.6); 1.489(15.8); 0.146(0.4); 0.008(2.9); 0.000(85.5); −0.008(3.6); −0.150(0.4)

Example 8: ¹H-NMR(400.0 MHz, d₆-DMSO):
δ = 8.880(0.8); 8.861(1.6); 8.844(1.0); 8.289(0.7); 8.284(0.9); 7.553(0.7); 7.548(0.7); 7.526(1.3); 7.504(1.4); 7.500(1.3); 7.491(1.2); 7.485(1.1); 7.477(1.0); 7.472(1.0); 7.467(1.0); 7.442(0.4); 7.296(1.4); 7.208(2.6); 7.189(3.5); 7.164(2.0); 7.145(1.2); 6.916(1.2); 6.899(2.1); 6.881(1.0); 6.879(0.9); 6.804(2.6); 6.784(2.3); 5.256(0.7); 5.239(1.6); 5.221(1.6); 5.204(0.7); 4.319(0.5); 4.310(0.7); 4.302(0.6); 4.291(1.6); 4.283(1.4); 4.274(1.4); 4.265(1.2); 4.252(1.1); 4.244(1.3); 4.233(1.3); 4.225(1.7); 4.206(1.1); 4.198(0.8); 4.188(1.1); 4.171(1.5); 4.153(1.1); 4.135(0.5); 3.324(90.8); 3.320(70.2); 3.314(88.7); 2.714(0.4); 2.678(0.5); 2.674(0.8); 2.669(0.6); 2.544(108.6); 2.530(27.4); 2.523(5.1); 2.514(46.4); 2.509(96.0); 2.505(128.3); 2.500(94.2); 2.496(46.8); 2.370(0.5); 2.336(0.6); 2.332(0.8); 2.327(0.6); 2.168(0.4); 2.161(0.4); 2.154(0.5); 2.142(0.9); 2.133(1.0); 2.126(1.4); 2.117(1.6); 2.112(1.5); 2.099(1.4); 2.089(1.3); 2.082(1.0); 2.072(0.8); 1.510(16.0); 1.494(15.4); 1.492(15.8); 0.000(21.4)

Example 9: ¹H-NMR(400.0 MHz, d₆-DMSO):
δ = 8.899(1.9); 8.879(1.9); 8.311(2.2); 7.444(1.9); 7.423(3.0); 7.410(2.7); 7.389(0.4); 7.200(2.0); 7.182(3.0); 7.167(2.1); 7.147(1.3); 7.144(1.1); 6.917(1.5); 6.901(2.4); 6.880(1.1); 6.805(2.7); 6.784(2.4); 5.241(0.6); 5.222(1.2); 5.206(1.2); 5.189(0.6); 4.295(0.6); 4.286(0.5); 4.278(1.3); 4.268(1.2); 4.260(1.2); 4.250(1.3); 4.238(1.2); 4.228(1.1); 4.219(1.3); 4.200(0.6); 4.192(0.4); 4.166(0.4); 4.149(1.0); 4.131(1.5); 4.114(1.1); 4.096(0.5); 3.413(0.7); 3.330(1612.8); 3.324(894.4); 3.226(0.6); 3.194(0.4); 2.711(1.0); 2.675(3.6); 2.671(5.0); 2.666(3.7); 2.662(1.8); 2.541(291.1); 2.524(13.9); 2.511(314.6); 2.506(649.9); 2.502(863.2); 2.497(628.5); 2.493(308.6); 2.416(16.0); 2.367(1.4); 2.337(2.0); 2.333(4.0); 2.328(5.4); 2.324(4.6); 2.292(0.5); 2.266(0.4); 2.254(0.3); 2.153(0.6); 2.148(0.6); 2.126(1.0); 2.118(1.1); 2.113(1.0); 2.098(1.0); 2.091(0.9); 2.080(1.1); 2.072(1.2); 2.054(0.8); 2.045(0.6); 2.037(0.5); 2.027(0.4); 1.512(10.3); 1.507(10.8); 1.494(10.6); 1.489(10.4); 1.466(0.6); 1.447(0.5); 1.442(0.5); 1.297(0.5); 1.259(0.8); 1.235(1.1); 0.146(0.4); 0.008(3.4); 0.000(104.8); −0.008(4.2); −0.150(0.5)

Example 10: ¹H-NMR(400.0 MHz, d₆-DMSO):
δ = 8.876(1.9); 8.855(1.9); 7.953(1.6); 7.634(4.8); 7.614(6.3); 7.499(2.3); 7.479(2.9); 7.459(1.4); 7.194(1.9); 7.174(3.0); 7.154(2.0); 7.135(1.2); 6.903(1.4); 6.885(2.4); 6.866(1.1); 6.792(2.6); 6.771(2.4); 5.754(7.6); 5.229(0.5); 5.212(1.2); 5.194(1.2); 5.177(0.5); 4.282(0.4); 4.262(1.2); 4.253(1.1); 4.244(1.4); 4.238(1.6); 4.221(1.1); 4.212(1.2); 4.192(0.4); 4.127(0.4); 4.109(1.0); 4.091(1.4); 4.074(1.1); 4.056(0.5); 3.321(70.2); 2.891(8.6); 2.732(8.1); 2.671(0.4); 2.541(1.4); 2.502(63.8); 2.376(0.4); 2.329(0.4); 2.205(16.0); 2.154(0.3); 2.141(0.4); 2.129(0.6); 2.113(0.8); 2.106(0.8); 2.089(0.4); 2.080(0.5); 2.070(0.6); 2.062(0.9); 2.053(0.9); 2.045(0.8); 2.035(0.6); 2.027(0.5); 2.018(0.4); 1.989(0.5); 1.530(8.2); 1.522(8.9); 1.512(8.6); 1.505(8.4); 1.252(0.3); 1.234(0.7); 1.175(0.4); 0.000(61.9)

Example 11: ¹H-NMR(400.0 MHz, d₆-DMSO):
δ = 20.012(0.4); 8.871(1.4); 8.850(1.7); 7.907(1.5); 7.887(1.9); 7.862(1.8); 7.658(1.1); 7.638(2.0); 7.618(1.0); 7.282(0.6); 7.258(0.6); 7.189(1.6); 7.170(1.7); 7.159(1.7); 7.140(1.1); 6.907(1.2); 6.888(1.9); 6.869(1.0); 6.796(2.0); 6.778(1.9); 5.223(1.0); 5.206(0.9); 4.269(1.1); 4.260(0.9); 4.252(0.9); 4.242(1.0); 4.232(0.9); 4.221(0.9); 4.212(1.3); 4.194(1.1); 4.177(1.1); 4.159(0.8); 3.344(1031.4); 3.339(645.0); 3.329(682.0); 3.327(664.2); 2.711(1.6); 2.676(2.9); 2.671(3.9); 2.667(2.9); 2.542(392.0); 2.525(10.6); 2.520(15.5); 2.511(217.9); 2.507(456.1); 2.502(611.0); 2.498(444.7); 2.493(218.2); 2.368(1.4); 2.345(16.0); 2.334(3.0); 2.329(3.8); 2.324(2.9); 2.185(0.4); 2.086(0.8); 2.072(0.9); 2.063(0.8); 1.653(0.7); 1.528(7.9); 1.524(8.3); 1.510(8.1); 1.506(8.2); 1.298(0.4); 1.259(0.6); 1.236(0.9); 1.046(0.4); 1.030(0.4); 0.008(0.9);

TABLE 1-continued

NMR Peaklist 0.000(25.0); −0.008(0.9)
Example 12: ¹H-NMR(400.0 MHz, d₆-DMSO):
δ = 20.012(0.4); 8.889(1.4); 8.869(1.5); 8.310(1.1); 7.887(3.4); 7.881(3.8); 7.664(3.9); 7.657(3.9); 7.193(1.6); 7.174(1.9); 7.163(1.7); 7.144(1.1); 6.912(1.2); 6.893(2.0); 6.874(1.0); 6.802(2.1); 6.781(1.9); 5.221(1.0); 5.204(0.9); 4.273(1.0); 4.264(0.9); 4.255(0.9); 4.244(1.1); 4.235(0.9); 4.225(0.8); 4.216(1.0); 4.196(0.4); 4.153(0.8); 4.136(1.0); 4.118(0.8); 3.348(1346.3); 3.341(476.6); 3.337(406.5); 3.329(362.4); 2.712(1.2); 2.676(2.3); 2.672(3.2); 2.667(2.4); 2.542(309.5); 2.525(8.6); 2.520(12.8); 2.512(173.5); 2.507(364.2); 2.503(487.0); 2.498(353.7); 2.494(171.5); 2.368(1.1); 2.348(16.0); 2.334(2.3); 2.329(3.0); 2.325(2.2); 2.116(0.7); 2.092(0.7); 2.073(0.7); 2.064(0.8); 1.517(7.7); 1.512(8.0); 1.499(7.8); 1.494(7.6); 1.298(0.3); 1.259(0.4); 1.235(0.6); 0.000(21.4)
Example 13: ¹H-NMR(400.0 MHz, d₆-DMSO):
δ = 8.852(0.9); 8.831(0.9); 7.199(0.9); 7.179(1.4); 7.164(1.1); 7.147(1.5); 7.128(0.9); 7.045(0.5); 7.042(0.6); 7.026(0.9); 7.010(0.4); 7.006(0.4); 6.983(0.5); 6.979(0.5); 6.962(0.8); 6.941(0.4); 6.938(0.4); 6.920(0.6); 6.918(0.7); 6.902(1.1); 6.899(1.1); 6.883(0.5); 6.880(0.5); 6.802(1.2); 6.800(1.2); 6.782(1.1); 6.779(1.1); 5.228(0.5); 5.211(0.5); 4.281(0.6); 4.272(0.4); 4.264(0.5); 4.255(0.4); 4.245(0.4); 4.236(0.5); 4.226(0.4); 4.218(0.6); 4.165(0.5); 4.148(0.7); 4.130(0.5); 3.341(99.0); 3.333(113.1); 2.797(16.0); 2.712(0.4); 2.672(0.4); 2.542(100.3); 2.525(1.3); 2.520(1.8); 2.512(24.4); 2.507(50.7); 2.503(67.6); 2.498(49.4); 2.494(24.4); 2.411(6.9); 2.368(0.4); 2.329(0.4); 2.117(0.4); 2.106(0.5); 2.096(0.4); 2.088(0.5); 2.078(0.5); 1.516(4.7); 1.511(4.8); 1.498(4.8); 1.494(4.7); 0.000(3.6)
Example 14: ¹H-NMR(400.0 MHz, d₆-DMSO):
δ = 8.813(2.1); 8.793(2.1); 7.952(0.4); 7.616(7.8); 7.601(7.8); 7.282(1.3); 7.267(3.2); 7.252(2.9); 7.246(3.2); 7.239(3.7); 7.232(3.4); 7.225(3.7); 7.216(1.6); 6.927(0.6); 5.753(5.3); 5.532(0.6); 5.511(1.6); 5.490(1.6); 5.470(0.6); 4.248(0.4); 4.231(1.0); 4.213(1.4); 4.196(1.0); 4.178(0.4); 3.318(204.7); 3.028(0.5); 3.021(0.5); 3.007(0.6); 2.998(0.6); 2.989(0.7); 2.982(0.9); 2.967(0.9); 2.960(0.8); 2.891(2.9); 2.866(1.4); 2.847(1.0); 2.826(0.8); 2.806(0.4); 2.732(2.3); 2.670(1.2); 2.540(4.0); 2.530(18.7); 2.505(152.0); 2.501(202.6); 2.497(158.7); 2.472(1.4); 2.463(1.2); 2.452(1.0); 2.441(1.0); 2.432(0.8); 2.420(0.4); 2.412(0.4); 2.328(1.2); 2.324(1.0); 2.049(0.4); 2.027(1.1); 2.017(0.5); 2.006(1.1); 1.996(1.0); 1.988(0.5); 1.975(1.0); 1.954(0.4); 1.508(16.0); 1.490(15.9); 1.252(1.2); 1.235(1.5); 1.169(0.9); 1.152(0.8); 0.900(0.7); 0.883(0.7); 0.146(0.9); 0.000(182.8); −0.150(1.0)
Example 15: ¹H-NMR(400.0 MHz, d₆-DMSO):
δ = 8.766(1.2); 8.746(1.3); 8.313(0.6); 7.691(1.5); 7.687(1.7); 7.671(1.8); 7.667(1.9); 7.538(1.2); 7.534(1.4); 7.519(2.2); 7.515(1.9); 7.465(2.1); 7.445(2.8); 7.426(1.2); 7.273(0.7); 7.257(1.6); 7.243(1.1); 7.239(1.1); 7.231(3.5); 7.222(2.0); 7.216(2.4); 7.208(0.7); 7.201(0.5); 5.510(0.3); 5.491(1.0); 5.470(1.0); 5.450(0.3); 4.160(0.6); 4.142(0.9); 4.124(0.7); 3.317(71.4); 3.004(0.3); 2.990(0.4); 2.982(0.4); 2.972(0.5); 2.965(0.6); 2.950(0.6); 2.942(0.5); 2.880(0.4); 2.858(0.8); 2.838(0.6); 2.818(0.5); 2.675(0.5); 2.670(0.6); 2.666(0.5); 2.524(1.8); 2.510(35.6); 2.506(74.4); 2.501(103.8); 2.497(79.5); 2.492(39.8); 2.469(0.7); 2.461(0.6); 2.449(0.6); 2.438(0.6); 2.430(0.5); 2.337(13.1); 1.996(0.7); 1.975(0.7); 1.965(0.7); 1.944(0.6); 1.525(9.8); 1.508(9.8); 1.398(16.0); 0.000(9.0); −0.008(0.3)

TABLE 2

Examples

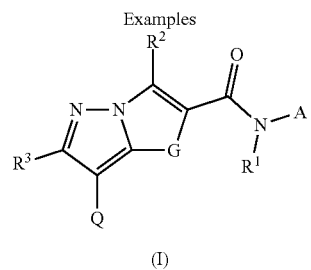

(I)

| No. | G | R1 | R2 | R3 | Q | A |
|---|---|---|---|---|---|---|
| 1 | S | H | isopropyl | methyl | 3,5-Dichlorophenyl | (4S)-3,4-Dihydro-2H-chromen-4-yl |
| 2 | S | H | isopropyl | methyl | 2,3-Dichlorophenyl | (4S)-3,4-Dihydro-2H-chromen-4-yl |
| 3 | S | H | isopropyl | methyl | 2-Fluoro-3-(trifluoromethyl)phenyl | (4S)-3,4-Dihydro-2H-chromen-4-yl |
| 4 | S | H | isopropyl | methyl | 2-Fluoro-3-(trifluoromethoxy)phenyl | (4S)-3,4-Dihydro-2H-chromen-4-yl |
| 5 | S | H | isopropyl | methyl | 3,5-Dichloro-4-fluorophenyl | (4S)-3,4-Dihydro-2H-chromen-4-yl |
| 6 | S | H | isopropyl | methyl | 2,4-Difluoro-3-(dimethylamino)-phenyl | (4S)-3,4-Dihydro-2H-chromen-4-yl |
| 7 | S | H | isopropyl | methyl | 3,4-Dichlorophenyl | (4S)-3,4-Dihydro-2H-chromen-4-yl |
| 8 | S | H | isopropyl | methyl | 3,4-Difluorophenyl | (4S)-3,4-Dihydro-2H-chromen-4-yl |
| 9 | S | H | isopropyl | methyl | 2,3,4-Trifluorophenyl | (4S)-3,4-Dihydro-2H-chromen-4-yl |
| 10 | S | H | isopropyl | methyl | 2,6-Dichlorophenyl | (4S)-3,4-Dihydro-2H-chromen-4-yl |
| 11 | S | H | isopropyl | methyl | 2-Chloro-3-(trifluoromethyl)phenyl | (4S)-3,4-Dihydro-2H-chromen-4-yl |
| 12 | S | H | isopropyl | methyl | 2,3,5-Trichlorophenyl | (4S)-3,4-Dihydro-2H-chromen-4-yl |
| 13 | S | H | isopropyl | methyl | 2-Fluoro-3-(dimethylamino)-phenyl | (4S)-3,4-Dihydro-2H-chromen-4-yl |
| 14 | S | H | isopropyl | methyl | 3,5-Dichloro-4-fluorophenyl | (1S)-2,3-Dihydro-1H-inden-1-yl |
| 15 | 5 | H | isopropyl | methyl | 2,3-Dichlorophenyl | (1S)-2,3-Dihydro-1H-inden-1-yl |

Experimental Section—Biological Assays

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: *C. elegans* Slo-1a—Action at a Recombinant *C. elegans* Cell Line Generation of a Stable *C. elegans* CHO Cell Line A CHO cell line was obtained from ATCC, code ATCC CRL-9096. For transfection with plasmid DNA to express *C. elegans* Slo-1a (accession number AAL28102) CHO cells were passaged to 40% confluence before adding the transfection solution to the cell culture. The transfection solution included 300 µL OptiMEM (Life Technologies, Nr.: 31985), 2 µL (=6 µg) of plasmid DNA containing the *C. elegans* Slo 1a gene and 9 µL FugeneHD (Promega, Nr.: E2311), and was added to the cells prior to incubation for 48 hours at 37° C., 5% $CO_2$. The transfection medium was exchanged for the selection medium which contains additional G418 (2 mg/ml, Invitrogen, Nr.: 10131) and the cells were seeded into 384 well plates (300 cells/well). After a few weeks, the remaining surviving cells were tested with a voltage sensitive dye (Membrane Potential Assay Kit, Molecular Devices Nr.: R8034) for K+ channel expression. Positive cell clones were purified by the limited dilution technique. For this the clone with the highest and most robust signal in the voltage sensitive dye assay was further subcloned (incubated) in 384 well plates (0.7 cells/well) in order to obtain clonal purity. This generated a final stable CHO cell line expressing the *C. elegans* Slo-1a.

Cell Culture Conditions

Cells were cultured at 37° C. and 5% $CO_2$ in MEMalpha with Gutamax I (Invitrogen, Nr.: 32571), supplemented with 10% (v/v) heat inactivated fetal bovine serum (Invitrogen, Nr.: 10500), G418 (1 mg/ml, Invitrogen, Nr.: 10131). Cells were detached using Accutase (Sigma, Nr.: A6964).

Membrane Potential Measurements

Laboratory compound testing was performed on 384-well microtiter plates (MTPs, Greiner, Nr.: 781092). 8000 cells/well were plated onto 384-well MTPs and cultured for 20 to 24 hours at 37° C. and 5% $CO_2$. After removal of the cell culture medium, the cells were washed once with tyrode (150 mM NaCl, 0.3 mM KCl, 2 mM $CaCl_2$, 1 mM $MgCl_2$, 0.8 mM $NaH_2PO_4$, 5 mM Glucose, 28 mM Hepes, pH 7.4) and then loaded with the voltage sensitive dye of the Membrane Potential Assay Kit diluted in tyrode for 1 h at room temperature.

After starting the measurement of fluorescence using a FLIPR Tetra (Molecular Devices, Exc. 510-545 nm, Emm. 565-625 nm), test compounds were added followed by the addition of KCl tyrode (final assay concentration: 70 mM KCl, 2 mM $CaCl_2$, 1 mM $MgCl_2$, 0.8 mM $NaH_2PO_4$, 5 mM Glucose, 28 mM Hepes, pH 7.4, including the voltage sensitive dye). The measurement was completed after 7 minutes.

Statistics

The data were evaluated by using the ActivityBase XLfit software (IDBS) for curve fitting and calculation of the half-maximal effective concentration ($EC_{50}$) and are reported as negative decadic logarithm ($pE_{50}$).

For the following examples, $pE_{50}$>7.5-8.5 has been found for: 1, 7, 8, 9, 14.

For the following examples, $pE_{50}$>8.5 has been found for: 2, 3, 4, 5, 6, 10, 11, 12, 13, 15.

In Vitro Assay 2: *Nippostrongylus brasiliensis* (NIPOBR)

Adult *Nippostrongylus brasiliensis* were washed with saline buffer containing 100 U/ml penicillin, 0.1 mg/ml streptomycin and 2.5 µg/ml amphotericin B. Test compounds were dissolved in DMSO and worms were incubated in medium in a final concentration of 10 µg/ml (10 ppm) respectively 1 µg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was higher than 80% at 10 µg/ml: 1, 2, 3, 4, 5, 6, 7, 14.

For the following examples, activity (reduction of AChE compared to negative control) was higher than 80% at 1 µg/ml: 1, 5, 6, 13, 14.

In Vitro Assay 3: *Dirofilaria immitis* Microfilariae (DIROIM L1)

≥250 *Dirofilaria immitis* microfilariae, which were freshly purified from blood, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: 1, 2, 3, 4, 5, 6, 7, 8, 9, 10, 11, 12, 13, 14, 15.

In vitro assay 4: *Dirofilaria immitis* (DIROIM L4)

10 *Dirofilaria immitis* third-stage larvae, which were freshly isolated from their vector (intermediate host), were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Within these 72 h of incubation the majority of larvae in negative control moult to fourth-stage larvae. Efficacy was determined as the reduction of motility in comparison to the negative control. Based on the evaluation of a wide concentration range, concentration-response curves as well as $EC_{50}$-values were calculated.

For the following examples, the $EC5_0$ was <0.1 ppm: 2, 3, 5, 6, 8, 14, 15.

In Vitro Assay 5: *Litomosoides sigmodontis* (LTMOSI L3)

10 *Litomosoides sigmodontis* third-stage larvae, which were freshly isolated from the pleural cavity of an infected rodent, were added to wells of a microtitre plate containing a nutrient medium and the test compound in DMSO. Compounds were tested in concentration-response assay in duplicate. Larvae exposed to DMSO and no test compounds were used as negative controls. Larvae were evaluated after 72 h of incubation with the compound. Efficacy was determined as the reduction of motility in comparison to the negative control. Based on the evaluation of a wide concentration range, concentration-response curves as well as $EC_{50}$-values were calculated.

For the following examples, the $EC_{50}$ was <0.1 ppm: 2, 3, 6, 15.

In Vitro Assay 6: *Cooperia curticei* (COOPCU L3)

Solvent: dimethyl sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 100% at an application rate of 20 ppm: 11, 12.

In this test for example, the following compounds from the preparation examples showed good activity of 90% at an application rate of 20 ppm: 2, 3, 5, 6, 9, 13.

In this test for example, the following compounds from the preparation examples showed good activity of 80% at an application rate of 20 ppm: 4.

In Vitro Assay 7: *Haemonchus Contortus* (HAEMCO L3)
Solvent: dimethyl sulfoxide To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days the percentage of larval mortality is recorded. 100% efficacy means all larvae are killed, 0% efficacy means no larvae are killed.

In this test for example, the following compounds from the preparation examples showed good activity of 90% at an application rate of 20 ppm: 1, 3, 11.

In this test for example, the following compounds from the preparation examples showed good activity of 80% at an application rate of 20 ppm: 4, 12.

Formulation Example

Exemplary formulations consisted of the active substance in 10% Transcutol, 10% Cremophor EL and 80% isotonic saline solution. First the active substance was dissolved in Transcutol. After solution in Transcutol, Cremophor and isotonic saline solution were added. These formulations were used as service formulations in the following in vivo assay.

An example for a formulation according to the present invention is the following formulation Example F1. Therein, the active substance was dissolved in Transcutol to form a stock solution A. Then 0.100 mL of this stock solution A were taken and 0.100 mL Cremophor EL and 0.800 mL isotonic saline solution were added. The resulting liquid formulation (formulation example F1) had a volume of 1 mL.

Stock solution A:
4.0 mg Example compound of the present invention
0.100 mL Transcutol Formulation Example F1

0.100 mL stock solution A,
0.100 mL Cremophor EL, and
0.800 mL isotonic saline solution.

In Vivo Assay

*Haemonchus contortus/Trichostrongylus colubriformis/* Gerbil

Gerbils, experimentally infected with *Haemonchus* and/or *Trichostrongylus*, were treated once during late prepatency. Test compounds were formulated as solutions or suspensions and applied orally or intraperitoneally. For both applications the same service formulation was used. The volume of the application amounted to normally 20 ml/kg at a maximum. By way of example, a gerbil with 40 g body weight was treated with 0.200 mL of the formulation of formulation example F1. This corresponded to a treatment with 20 mg/kg body weight.

Efficacy was determined per group as reduction of worm count in stomach and small intestine, respectively, after necropsy compared to worm count in an infected and placebo-treated control group.

The following examples were tested and had an activity of ≥70% or higher at the given treatment:

| Treatment | *Haemonchus contortus* |
|---|---|
| ≤10 mg/kg intraperitoneally | Expl No 1; 4 |

The invention claimed is:
1. A compound of formula (I):

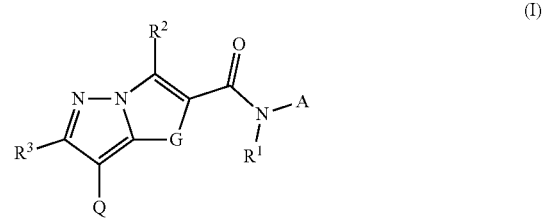

wherein
A is A1 or A2,

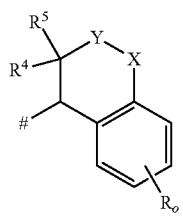

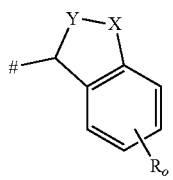

o is 0, 1, 2, 3 or 4,
R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl, and —$SO_2$—$C_1$-$C_4$-halogenoalkyl having 1 to 5 halogen atoms,
X and Y are independently selected from the group consisting of $CR^6R^7$, O, S, and N—$R^8$, wherein at least one of X and Y is $CR^6R^7$, or X and Y form together a group selected from —C(O)—O—, —C(O)—NR$^8$—, —S(O)—NR$^8$—, —SO$_2$—NR$^8$—, and —SO$_2$—O—, G is S, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —N($C_1$-$C_4$-alkyl)$_2$, NH$_2$—$C_1$-$C_4$-alkyl-, $C_1$-$C_4$-alkyl-NH—$C_1$-$C_4$-alkyl-, ($C_1$-$C_4$-alkyl)$_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —SO$_2$—$C_1$-$C_4$-alkyl, —SO$_2$—$C_1$-$C_4$-halogenoalkyl having 1 to 5 halogen atoms, phenyl-$C_1$-$C_4$-alkyl, optionally substituted by 1, 2, 3, 4 or 5 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, and heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, $R^2$ is selected from the group consisting of hydrogen, halogen, cyano, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, —C(O)—NH($C_3$-$C_6$-cycloalkyl), —C(O)—N($C_1$-$C_4$-alkyl)($C_3$-$C_6$-cycloalkyl), —NR$^9$R$^{10}$, —OR$^{11}$, —SR$^{12}$, —S(O)R$^{12}$, —SO$_2$R$^{12}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, —NO$_2$, cyano, $C_1$-$C_4$-alkyl-C(O)—, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, —OH, —NO$_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —SO$_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—NH$_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —SO$_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO$_2$—$C_1$-$C_4$-halogenoalkyl having 1 to 5 halogen atoms, and 4- to 10-membered heterocycloalkyl, $R^3$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, and —SO$_2$—$C_1$-$C_4$-alkyl, $R^4$ is selected from the group consisting of hydrogen, —OH, $C_1$-$C_4$-alkyl, and $C_1$-$C_4$-alkoxy, $R^5$ is selected from the group consisting of hydrogen, $C_1$-$C_4$-alkyl, and $C_1$-$C_4$-alkoxy, or $R^4$ and $R^5$ form, together with the carbon atom to which they are attached, a 3- to 6-membered ring selected from the group consisting of $C_3$-$C_6$-cycloalkyl and 3- to 6-membered heterocycloalkyl, $R^6$ is selected from the group consisting of hydrogen, —OH, fluorine, $C_1$-$C_4$-alkyl, and $C_1$-$C_4$-alkoxy, $R^7$ is selected from the group consisting of hydrogen, —OH, fluorine, $C_1$-$C_4$-alkyl, and $C_1$-$C_4$-alkoxy, or $R^6$ and $R^7$ form, together with the carbon atom to which they are attached, a 3- to 6-membered ring selected from the group consisting of $C_3$-$C_6$-cycloalkyl and 3- to 6-membered heterocycloalkyl, $R^8$ is selected from the group consisting of hydrogen, $C_1$-$C_4$-alkyl, $C_1$-$C_4$-halogenoalkyl having 1 to 5 halogen atoms, and $C_1$-$C_4$-alkoxy, $R^9$ and $R^{10}$ are independently selected from the group consisting of hydrogen, —OH, —$NH_2$, —NH($C_1$-$C_4$-alkyl), —N($C_1$-$C_4$-alkyl)$_2$, —NH(—C(O)—$C_1$-$C_4$-alkyl), —N($C_1$-$C_4$-alkyl)(—C(O)—$C_1$-$C_4$-alkyl), $C_1$-$C_4$-alkoxy, $C_1$-$C_4$-alkoxy-C(O)—, $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and ($C_1$-$C_4$-alkoxy)$_2$P(=O)—, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, benzo-$C_5$-$C_6$-cycloalkyl, each of which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, a monocyclic or a bicyclic heterocycle selected from the group of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, $R^{11}$ is selected from the group consisting of
—$NH_2$, —NH($C_1$-$C_4$-alkyl), —N($C_1$-$C_4$-alkyl)$_2$, $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, $R^{12}$ is selected from the group consisting of hydrogen, $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, Q is selected from the group consisting of 6- or 10-membered aryl and 5- to 10-membered heteroaryl, each of which is optionally substituted by 1, 2, 3, 4 or 5 substituents selected from the group consisting of halogen, $SF_5$, cyano, —CHO, nitro, oxo, $C_1$-$C_4$-alkyl, $C_1$-$C_4$-hydroxyalkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, wherein when Y is O, S or N—$R^8$, none of $R^4$, $R^5$, $R^6$ and $R^7$ is —OH, and wherein when X is O, S or N—$R^8$, none of $R^6$ and $R^7$ is —OH, or a stereoisomer, a tautomer, an N-oxide, a hydrate, a solvate, or a salt thereof, or a mixture of any of the foregoing.

2. The compound according to claim 1, wherein:

A is A1 or A2,

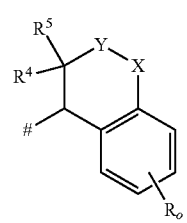

A1

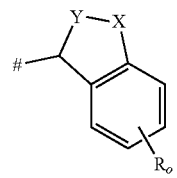

A2 o is 0, 1, 2, 3 or 4,

R is selected from the group consisting of hydrogen, halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl, —S(O)—$C_1$-$C_4$-halogenoalkyl, and —$SO_2$—$C_1$-$C_4$-halogenoalkyl having 1 to 5 halogen atoms, X and Y are independently selected from the group consisting of $CR^6R^7$, O, S, and N—$R^8$, wherein at least one of X and Y is $CR^6R^7$, or X and Y form together a group selected from —C(O)—O—, —C(O)—$NR^8$—, —S(O)—$NR^8$—, —$SO_2$—$NR^8$—, and —$SO_2$—O—, G is S, $R^1$ is selected from the group consisting of hydrogen, cyano, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, —NH—$C_1$-$C_4$-alkyl, —$N(C_1$-$C_4$-alkyl)_2$, $NH_2$—$C_1$-$C_4$-alkyl-, $C_1$-$C_4$-alkyl-NH—$C_1$-$C_4$-alkyl-, $(C_1$-$C_4$-alkyl)_2$N—$C_1$-$C_4$-alkyl-, $C_1$-$C_4$-alkyl-C(O)—, $C_1$-$C_4$-halogenoalkyl-C(O)— having 1 to 5 halogen atoms, $C_1$-$C_4$-alkoxy-C(O)—, benzyloxy-C(O)—, $C_1$-$C_4$-alkoxy-$C_1$-$C_4$-alkyl-C(O)—, —$SO_2$—$C_1$-$C_4$-alkyl, —$SO_2$—$C_1$-$C_4$-halogenoalkyl having 1 to 5 halogen atoms, phenyl-$C_1$-$C_4$-alkyl, optionally substituted by 1, 2, 3, 4 or 5 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, $R^2$ is selected from the group consisting of
hydrogen, halogen, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)_2$, —C(O)—$NH(C_3$-$C_6$-cycloalkyl), —C(O)—$N(C_1$-$C_4$-alkyl)(C_3$-$C_6$-cycloalkyl), —$NR^9R^{10}$, —$OR^{11}$, —$SR^{12}$, —$S(O)R^{12}$, —$SO_2R^{12}$, $C_1$-$C_6$-alkyl, $C_3$-$C_6$-cycloalkyl, $C_2$-$C_4$-alkenyl, $C_3$-$C_6$-cycloalkenyl, $C_2$-$C_4$-alkynyl, phenyl-$C_1$-$C_4$-alkyl, each of which is optionally substituted by 1, 2, 3, 4 or 5 substituents independently selected from the group consisting of halogen, —OH, —$NO_2$, cyano, $C_1$-$C_4$-alkyl-C(O)—, $C_1$-$C_4$-alkoxy-C(O)—, —C(O)—$NH_2$, —C(O)—$NH(C_1$-$C_4$-alkyl), —C(O)—$N(C_1$-$C_4$-alkyl)_2$, $C_1$-$C_4$-alkyl, $C_1$-$C_4$-halogenoalkyl having 1 to 5 halogen atoms, $C_1$-$C_4$-alkoxy, —$NH_2$, —$NH(C_1$-$C_4$-alkyl), —$N(C_1$-$C_4$-alkyl)_2$, —$NH(C_3$-$C_6$-cycloalkyl), —$N(C_1$-$C_4$-alkyl)(C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, —OH, —$NO_2$, cyano, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH_2$, —$NH(C_1$-$C_4$-alkyl), —$N(C_1$-$C_4$-alkyl)_2$, —$NH(C_3$-$C_6$-cycloalkyl), —$N(C_1$-$C_4$-alkyl)(C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)_2$, —$NH(C_3$-$C_6$-cycloalkyl), —$N(C_1$-$C_4$-alkyl)(C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, cyano, nitro, —OH, oxo, thiono, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)_2$, —$NH(C_3$-$C_6$-cycloalkyl), —$N(C_1$-$C_4$-alkyl)(C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —SO$_2$—C$_1$-C$_4$-halogenoalkyl having 1 to 5 halogen atoms, and 4- to 10-membered heterocycloalkyl, R$^3$ is selected from the group consisting of hydrogen, halogen, —OH, cyano, C$_1$-C$_4$-alkyl, C$_3$-C$_6$-cycloalkyl, C$_1$-C$_4$-halogenoalkyl having 1 to 5 halogen atoms, C$_1$-C$_4$-alkoxy-C$_1$-C$_4$-alkyl, C$_1$-C$_4$-alkoxy, C$_1$-C$_4$-alkyl-C(O)—, —NH$_2$, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), —S—C$_1$-C$_4$-alkyl, and —S(O)—C$_1$-C$_4$-alkyl, —SO$_2$—C$_1$-C$_4$-alkyl, R$^4$ is selected from the group consisting of hydrogen, —OH, C$_1$-C$_4$-alkyl, and C$_1$-C$_4$-alkoxy, R$^5$ is selected from the group consisting of hydrogen, C$_1$-C$_4$-alkyl, and C$_1$-C$_4$-alkoxy, R$^6$ is selected from the group consisting of hydrogen, —OH, fluorine, C$_1$-C$_4$-alkyl, and C$_1$-C$_4$-alkoxy, R$^7$ is selected from the group consisting of hydrogen, —OH, fluorine, C$_1$-C$_4$-alkyl, and C$_1$-C$_4$-alkoxy, R$^8$ is selected from the group consisting of hydrogen, C$_1$-C$_4$-alkyl, C$_1$-C$_4$-halogenoalkyl having 1 to 5 halogen atoms, and C$_1$-C$_4$-alkoxy, R$^9$ and R$^{10}$ are independently selected from the group consisting of hydrogen, —OH, —NH$_2$, —NH(C$_1$-C$_4$-alkyl), —N(C$_1$-C$_4$-alkyl)$_2$, —NH(—C(O)—C$_1$-C$_4$-alkyl), C$_1$-C$_4$-alkoxy, C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, —NH—C(O)—C$_1$-C$_4$-alkyl, —N(C$_1$-C$_4$-alkyl)-(—C(O)—C$_1$-C$_4$-alkyl), C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, —SO$_2$—C$_1$-C$_4$-halogenoalkyl having 1 to 5 halogen atoms, and (C$_1$-C$_4$-alkoxy)$_2$P(=O)—, heterocyclyl-C$_1$-C$_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, and —SO$_2$—C$_1$-C$_4$-halogenoalkyl having 1 to 5 halogen atoms, phenyl, benzo-C$_5$-C$_6$-cycloalkyl, each of which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, and —SO$_2$—C$_1$-C$_4$-halogenoalkyl having 1 to 5 halogen atoms, and a monocyclic or a bicyclic heterocycle selected from the group of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, and —SO$_2$—C$_1$-C$_4$-halogenoalkyl having 1 to 5 halogen atoms, R$^{11}$ is selected from the group consisting of —NH$_2$, —NH(C$_1$-C$_4$-alkyl), —N(C$_1$-C$_4$-alkyl)$_2$, C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, cyano, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, and —SO$_2$—C$_1$-C$_4$-halogenoalkyl having 1 to 5 halogen atoms, heterocyclyl-C$_1$-C$_4$-alkyl, wherein the heterocyclyl substitutent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, C$_1$-C$_4$-alkoxy-C(O)—, —C(O)—NH$_2$, —C(O)—NH(C$_1$-C$_4$-alkyl), —C(O)—N(C$_1$-C$_4$-alkyl)$_2$, C$_1$-C$_4$-alkyl, C$_1$-C$_4$-halogenoalkyl having 1 to 5 halogen atoms, C$_1$-C$_4$-alkoxy, hydroxy-C$_1$-C$_4$-alkyl, C$_1$-C$_4$-halogenoalkoxy having 1 to 5 halogen atoms, C$_3$-C$_6$-cycloalkyl, —NH$_2$, —NH(C$_1$-C$_4$-alkyl), —N(C$_1$-C$_4$-alkyl)$_2$, —S—C$_1$-C$_4$-alkyl, —S(O)—C$_1$-C$_4$-alkyl, —SO$_2$—C$_1$-C$_4$-alkyl, —S—C$_1$-C$_4$-halogenoalkyl having 1 to 5 halogen atoms, —S(O)—C$_1$-C$_4$-halogenoalkyl having 1 to 5 halogen atoms, and —SO$_2$—C$_1$-C$_4$-halogenoalkyl having 1 to 5 halogen atoms, phenyl, which is optionally substituted by 1, 2 or 3 substituents independently selected from the group consisting of halogen, cyano, nitro, —OH, C$_1$-C$_4$-alkyl, C$_1$-C$_4$-halogenoalkyl having 1 to 5 halogen atoms, C$_1$-C$_4$- alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, $R^{12}$ is selected from the group consisting of Hydrogen, $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, heterocyclyl-$C_1$-$C_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, phenyl, which is optionally substituted by 1, 2 or 3 substituents independently selected from the group consisting of halogen, cyano, nitro, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, nitro, —OH, oxo, thiono, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, hydroxy-$C_1$-$C_4$-alkyl, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, Q is a phenyl ring of formula (Q1)

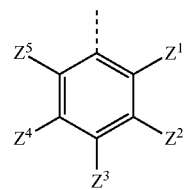

wherein $Z^1$, $Z^2$, $Z^3$, $Z^4$, and $Z^5$ are independently selected from the group consisting of hydrogen, halogen, $SF_5$, cyano, —CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocyclyl, which is optionally substituted with 1 or 2 substituents selected from the group consisting of fluorine, chlorine, bromine, methyl, and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocyclyl which itself is optionally substituted with 1 or 2 substituents selected from the group consisting of fluorine, chlorine, bromine, methyl and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO ($C_1$-$C_4$-halogenoalkyl) having 1 to 5 halogen atoms, or $Z^1$ and $Z^2$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine, and oxo, and $Z^3$, r, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-alkoxy-C(O)—, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl, and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl or cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH($C_1$-$C_4$-alkyl), —CONH($C_3$-$C_6$-cycloalkyl), —NHCO($C_1$-$C_4$-alkyl), —NHCO ($C_3$-$C_6$-cycloalkyl), and —NHCO($C_1$-$C_4$-halogenoalkyl) having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substitutents selected from the group consisting of methyl, fluorine, and oxo, and $Z^1$, $Z^4$, and $Z^5$ are independently selected from the group consisting of hydrogen, halogen, $SF_5$, cyano, CHO, nitro, $C_1$-$C_4$-alkyl, $C_1$-$C_4$-halogenoalkyl having 1 to 5 halogen atoms, hydroxy, $C_1$-$C_4$-alkoxy, $C_3$-$C_6$-cycloalkyl-$C_1$-$C_4$-alkoxy, cyano-$C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —NH—$SO_2$—($C_1$-$C_4$-alkyl), —N($SO_2$—[$C_1$-$C_4$-alkyl])($C_1$-$C_4$-alkyl), ($C_1$-$C_4$-alkoxyimino)-$C_1$-$C_4$-alkyl, 4- to 6-membered heterocycloalkyl which is optionally substituted with 1 or 2 substituents selected from the group consisting of fluorine, methyl, and cyano, —$CH_2$—O—($C_1$-$C_4$-alkyl), —$CH_2$—NH($C_1$-$C_4$-alkyl), —$CH_2$—N($C_1$-$C_4$-alkyl)$_2$, methyl substituted with a 4- to 6-membered heterocycloalkyl which itself is optionally substituted with 1 or 2 substituents selected from the group consisting of fluorine, methyl, and cyano, —$CH_2$—S—($C_1$-$C_4$-alkyl), —$CH_2$—S(O)—($C_1$-$C_4$-alkyl), —$CH_2$—$SO_2$—($C_1$-$C_4$-alkyl), —S—($C_1$-$C_4$-alkyl), —S(O)—($C_1$-$C_4$-alkyl), —$SO_2$—($C_1$-$C_4$-alkyl), —S—($C_1$-$C_4$-halogenoalkyl) having 1 to 5 halogen atoms, —S(O)—($C_1$-$C_4$-halogenoalkyl) having 1 to 5 halogen atoms, —$SO_2$—($C_1$-$C_4$-halogenoalkyl) having 1 to 5 halogen atoms, —CONH ($C_1$-$C_4$-alkyl), —CONH($C_3$-$C_6$-cycloalkyl), —NHCO($C_1$-$C_4$-alkyl), —NHCO($C_3$-$C_6$-cycloalkyl), and —NHCO($C_1$-$C_4$-halogenoalkyl) having 1 to 5 halogen atoms, or Q is a pyridine ring of formula (Q2)

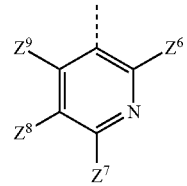

(Q2)

wherein $Z^6$, $Z^7$, $Z^8$ and $Z^9$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), and —N($C_1$-$C_4$-alkyl)($C_3$-$C_6$-cycloalkyl), or Q is a pyrimidine ring of formula (Q3)

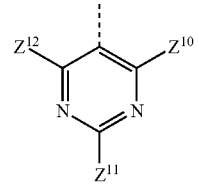

(Q3)

wherein $Z^{10}$, $Z^{11}$ and $Z^{12}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), and —N($C_1$-$C_4$-alkyl)($C_3$-$C_6$-cycloalkyl), or Q is a pyridine ring of formula (Q4)

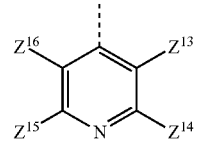

(Q4)

wherein $Z^{13}$, $Z^{14}$, $Z^{15}$ and $Z^{16}$ are independently selected from the group consisting of hydrogen halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-hydroxyalkyl, $NH_2$, —$NH(C_1$-$C_4$-alkyl), —$N(C_1$-$C_4$-alkyl)$_2$, —$NH(C_3$-$C_6$-cycloalkyl), —$N(C_1$-$C_4$-alkyl)($C_3$-$C_6$-cycloalkyl), —NH—CO—$C_1$-$C_4$-alkyl, and monocyclic heterocycles selected from the group of 4- to 7-membered heterocycloalkyl or 5-membered heteroaryls having at least one nitrogen atom via which the heteroaryl ring is connected to the pyridine ring, each of which is optionally substituted with 1, 2 or 3 substituents independently selected from the group consisting of halogen, cyano, nitro, —OH, oxo, thiono, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —$NH(C_1$-$C_4$-alkyl), —$N(C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—($C_1$-$C_4$-halogenoalkyl) having 1 to 5 halogen atoms, —S(O)—($C_1$-$C_4$-halogenoalkyl) having 1 to 5 halogen atoms, and —$SO_2$—($C_1$-$C_4$-halogenoalkyl) having 1 to 5 halogen atoms, or Q is a pyridine ring of formula (Q5)

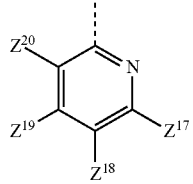

(Q5)

wherein
$Z^{17}$, $Z^{18}$, $Z^{19}$ and $Z^{20}$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, —$NH(C_1$-$C_4$-alkyl), —$N(C_1$-$C_4$-alkyl)$_2$, —$NH(C_3$-$C_6$-cycloalkyl), and —$N(C_1$-$C_4$-alkyl)($C_3$-$C_6$-cycloalkyl), or Q is a 5-membered aromatic heterocycle of formula (Q6)

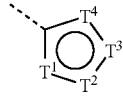

(Q6)

wherein
$T^1$-$T^4$ are independently selected from the group consisting of N, O, S, C-$Z^{21}$, and N—$Z^{22}$, wherein not more than one of $T^1$-$T^4$ is O, not more than one of $T^1$-$T^4$ is S, not more than one of $T^1$-$T^4$ is N—$Z^{22}$, and wherein
each $Z^{21}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and
each $Z^{22}$ is independently selected from the group consisting of hydrogen, $C_1$-$C_4$-alkyl, $C_1$-$C_4$-halogenoalkyl having 1 to 5 halogen atoms, $C_1$-$C_4$-alkyl-$C_3$-$C_6$-cycloalkyl, and $C_1$-$C_4$-alkoxy-$C_1$-$C_4$-alkyl, or Q is a 5-membered aromatic heterocycle of formula (Q7)

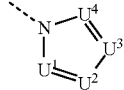

(Q7)

wherein
$U^1$-$U^4$ are independently selected from the group consisting of N and C—$Z^{23}$, wherein not more than three of $U^1$-$U^4$ are N, and wherein
each $Z^{23}$ is independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms,
wherein when Y is O, S or N—$R^8$, none of $R^4$, $R^5$, $R^6$ and $R^7$ is —OH, and wherein when X is O, S or N—$R^8$, none of $R^6$ and $R^7$ is —OH,
or a stereoisomer, a tautomer, an N-oxide, a hydrate, a solvate, or a salt thereof, or a mixture of any of the foregoing.

3. The compound according to claim 1, wherein:
A is A1 or A2,

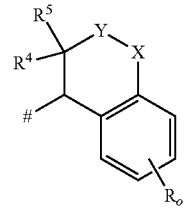

A1

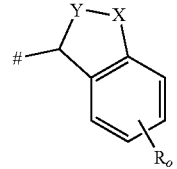

A2 o is 0, 1 or 2,
R is selected from the group consisting of hydrogen, halogen, $C_1$-$C_4$-alkyl, $C_1$-$C_4$-alkoxy, cyano, and $C_1$-$C_4$-halogenoalkyl having 1 to 5 halogen atoms,
X and Y are independently selected from the group consisting of $CR^6R^7$, O, S, and N—$R^8$, wherein at least one of X and Y is $CR^6R^7$,
G is S,
$R^1$ is selected from the group consisting of hydrogen, $C_1$-$C_4$-alkyl, $C_3$-$C_6$-cycloalkyl, $C_3$-$C_4$-alkenyl, $C_3$-$C_4$-alkynyl, $C_1$-$C_4$-alkoxy-$C_1$-$C_4$-alkyl, $C_3$-$C_6$-cycloalkyl-$C_1$-$C_3$-alkyl, and cyano-$C_1$-$C_4$-alkyl,
$R^2$ is selected from the group consisting of
hydrogen, halogen, cyano, —COOH, $C_1$-$C_4$-alkoxy-C(O)—, —C(O)—$NH_2$, —C(O)—$NH(C_1$-$C_4$-alkyl), —C(O)—$N(C_1$-$C_4$-alkyl)$_2$, —C(O)—$NH(C_3$-$C_6$-cycloalkyl), —C(O)—$N(C_1$-$C_4$-alkyl)($C_3$-$C_6$-cycloalkyl), —$NR^9R^{10}$, —$OR^{11}$, —$SR^{12}$, —$S(O)R^{12}$, —$SO_2R^{12}$, $C_1$-$C_4$-alkyl, $C_3$-$C_6$-cycloalkyl, $C_2$-$C_4$-alkenyl, $C_3$-$C_6$-cycloalkenyl, $C_2$-$C_4$-alkynyl or phenyl-$C_1$-$C_4$-alkyl, each of which is optionally substituted by 1, 2, 3, 4 or 5 substituents independently selected from the group consisting of halogen, —OH, cyano, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-halogenoalkyl having 1 to 5 halogen atoms, $C_1$-$C_4$-alkoxy, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, and —$SO_2$—$C_1$-$C_4$-halogenoalkyl having 1 to 5 halogen atoms, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, cyano, —OH, oxo, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, $C_1$-$C_4$-alkyl, $C_1$-$C_4$-alkyl-C(O)—, $C_1$-$C_4$-halogenoalkyl having 1 to 5 halogen atoms, $C_1$-$C_4$-alkoxy, hydroxy-$C_1$-$C_4$-alkyl, $C_1$-$C_4$-alkoxy-$C_1$-$C_4$-alkyl-, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), and 4- to 10-membered heterocycloalkyl, $R^3$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —$NH_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), —S—$C_1$-$C_4$-alkyl, —S(O)—$C_1$-$C_4$-alkyl, and —$SO_2$—$C_1$-$C_4$-alkyl, $R^4$ is selected from the group consisting of hydrogen, —OH, $C_1$-$C_4$-alkyl, and $C_1$-$C_4$-alkoxy, $R^5$ is hydrogen, $R^6$ is selected from the group consisting of hydrogen and $C_1$-$C_4$-alkyl, $R^7$ is selected from the group consisting of hydrogen and $C_1$-$C_4$-alkyl, $R^8$ is selected from the group consisting of hydrogen and $C_1$-$C_4$-alkyl, $R^9$ and $R^{10}$ are independently selected from the group consisting of hydrogen, —NH—(C(O)—$C_1$-$C_4$-alkyl), $C_1$-$C_4$-alkoxy, $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, —COOH, $C_1$-$C_4$-alkoxy-C(O)—, —C(O)—$NH_2$, —C(O)—NH($C_1$-$C_4$-alkyl), —C(O)—N($C_1$-$C_4$-alkyl)$_2$, —NH—C(O)—$C_1$-$C_4$-alkyl, —N($C_1$-$C_4$-alkyl)-(—C(O)—$C_1$-$C_4$-alkyl), $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, —$NH_2$, —NH($C_1$-$C_4$-alkyl), —N($C_1$-$C_4$-alkyl)$_2$, —S—$C_1$-$C_4$-alkyl, —S(O)—$C_1$-$C_4$-alkyl, —$SO_2$—$C_1$-$C_4$-alkyl, —S—$C_1$-$C_4$-halogenoalkyl having 1 to 5 halogen atoms, —S(O)—$C_1$-$C_4$-halogenoalkyl having 1 to 5 halogen atoms, —$SO_2$—$C_1$-$C_4$-halogenoalkyl having 1 to 5 halogen atoms, and ($C_1$-$C_4$-alkoxy)$_2$P(=O)—, heterocyclyl-$C_1$-$C_4$-alkyl, wherein the heterocyclyl substitutent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, phenyl, benzo-$C_5$-$C_6$-cycloalkyl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, and a monocyclic or a bicyclic heterocycle selected from the group of 4- to 10-membered heterocycloalkyl, 5-membered heteroaryl, and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{11}$ is selected from the group consisting of $C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, and $C_3$-$C_6$-cycloalkyl, and heterocyclyl-$C_1$-$C_4$-alkyl, wherein the heterocyclyl substitutent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, —OH, oxo, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, $R^{12}$ is selected from the group consisting of hydrogen, $C_1$-$C_4$-alkyl, phenyl-$C_1$-$C_4$-alkyl, each of which is optionally substituted by 1, 2 or 3 substituents independently selected from the group consisting of halogen, —OH, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, heterocyclyl-$C_1$-$C_4$-alkyl, wherein the heterocyclyl substitutent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, Q is a phenyl ring of formula (Q1)

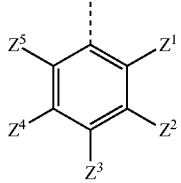
(Q1)

wherein
$Z^1$, $Z^2$, $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, hydroxy, $C_1$-$C_4$-alkoxy, $C_1$-$C_4$-halogenoalkoxy having 1 to 5 halogen atoms, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl), 4- to 6-membered heterocyclyl, which is optionally substituted with 1 or 2 substituents selected from the group consisting of fluorine, chlorine, bromine, methyl, and cyano, —S—($C_1$-$C_4$-alkyl), —S(O)—($C_1$-$C_4$-alkyl), and —SO$_2$—($C_1$-$C_4$-alkyl), or $Z^1$ and $Z^2$ form, together with the carbon atoms that they are connected to, a 5- or 6-membered heterocycloalkyl, a 5-membered heteroaryl, or a 6-membered heteroaryl, each of which may be optionally substituted with one or two substituents selected from the group consisting of methyl, fluorine, and oxo, and $Z^3$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, $C_1$-$C_4$-alkoxy-C(O)—, and $C_1$-$C_4$-halogenoalkoxy having 1 to 5 halogen atoms, or $Z^2$ and $Z^3$ form, together with the carbon atoms that they are connected to, a 5- or 6-membered saturated or partially saturated heterocyclic ring, a 5-membered heteroaryl, or a 6-membered heteroaryl, each of which may be optionally substituted with one or two substituents selected from the group consisting of methyl, fluorine, and oxo, and $Z^1$, $Z^4$, and $Z^5$ are independently selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms,
wherein when Y is O, S or N—$R^8$, $R^4$ is not —OH, or a stereoisomer, a tautomer, an N-oxide, a hydrate, a solvate, or a salt thereof, or a mixture of any of the foregoing.

4. The compound according to claim 1, wherein:
A is A1 or A2,

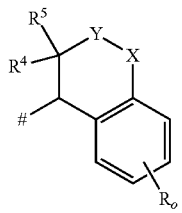
A1

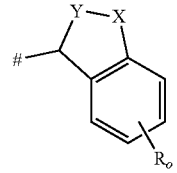
A2 o is 0 or 1,
R is selected from the group consisting of hydrogen, halogen, $C_1$-$C_4$-alkyl, and $C_1$-$C_4$-alkoxy,
X is selected from the group consisting of $CR^6R^7$, O, S, and N—$R^8$,
Y is $CR^6R^7$,
G is S,
$R^1$ is hydrogen or $C_1$-$C_4$-alkyl,
$R^2$ is selected from the group consisting of
hydrogen, halogen, —$NR^9R^{10}$, —$OR^{11}$, —$SR^{12}$, —$S(O)R^{12}$, —$SO_2R^{12}$, $C_1$-$C_4$ alkyl, $C_3$-$C_6$-cycloalkyl, $C_2$-$C_4$-alkenyl or $C_3$-$C_6$-cycloalkenyl, each of which is optionally substituted by 1, 2, 3, 4 or 5 substituents independently selected from the group consisting of halogen, cyano, $C_1$-$C_4$-alkoxy-C(O)—, and —C(O)—NH$_2$, and a monocyclic or a bicyclic heterocycle selected from the group consisting of 4- to 10-membered heterocycloalkyl, heterospirocycloalkyl, 5-membered heteroaryl, and 6-membered heteroaryl, each of which is optionally substituted by 1, 2, 3 or 4 substituents independently selected from the group consisting of halogen, —OH, oxo, —COOH, $C_1$-$C_4$-alkoxy-C(O)—, —C(O)—NH$_2$, $C_1$-$C_4$-alkyl, $C_1$-$C_4$-alkyl-C(O)—, $C_1$-$C_4$-halogenoalkyl having 1 to 5 halogen atoms, hydroxy-$C_1$-$C_4$-alkyl-, $C_1$-$C_4$-alkoxy-$C_1$-$C_4$-alkyl-, —NH$_2$, —N($C_1$-$C_4$-alkyl)$_2$, —NH($C_3$-$C_6$-cycloalkyl), —N($C_1$-$C_4$-alkyl)($C_3$-$C_6$-cycloalkyl), and 4- to 10-membered heterocycloalkyl, $R^3$ is selected from the group consisting of hydrogen, halogen, —OH, cyano, $C_1$-$C_4$-alkyl, $C_3$-$C_6$-cycloalkyl, $C_1$-$C_4$-halogenoalkyl having 1 to 5 halogen atoms, $C_1$-$C_4$-alkoxy-$C_1$-$C_4$-alkyl, $C_1$-$C_4$-alkoxy, $C_1$-$C_4$-alkyl-C(O)—, —NH$_2$, —NH($C_1$-$C_4$-alkyl), —N($C_1$-$C_4$-alkyl)$_2$, —NH($C_3$-$C_6$-cycloalkyl), —N($C_1$-$C_4$-alkyl)($C_3$-$C_6$-cycloalkyl)-S—$C_1$-$C_4$-alkyl, —S(O)—$C_1$-$C_4$-alkyl, and —SO$_2$—$C_1$-$C_4$-alkyl, $R^4$ is selected from the group consisting of hydrogen, —OH, and $C_1$-$C_4$-alkyl,
$R^5$ is hydrogen,
$R^6$ is selected from the group consisting of hydrogen and $C_1$-$C_4$-alkyl,
$R^7$ is selected from the group consisting of hydrogen and $C_1$-$C_4$-alkyl,
$R^8$ is selected from the group consisting of hydrogen and $C_1$-$C_4$-alkyl,
$R^9$ and $R^{10}$ are independently selected from the group consisting of
hydrogen, —NH(—C(O)—$C_1$-$C_4$-alkyl), $C_1$-$C_4$-alkoxy,
$C_1$-$C_4$-alkyl, $C_3$-$C_6$-cycloalkyl, phenyl-$C_1$-$C_4$-alkyl, each of which is optionally substituted by 1, 2 or 3 substituents independently selected from the group consisting of halogen, —OH, —COOH, $C_1$-$C_4$-alkoxy-C(O)—, —C(O)—NH$_2$, —C(O)—N($C_1$-$C_4$-alkyl)$_2$, —NH—C(O)—$C_1$-$C_4$-alkyl, $C_1$-$C_4$-alkyl, $C_1$-$C_4$-alkoxy, $C_3$-$C_6$-cycloalkyl, —NH$_2$, —N($C_1$-

C$_4$-alkyl)$_2$, —S—C$_1$-C$_4$-alkyl, —S(O)—C$_1$-C$_4$-alkyl, —SO$_2$—C$_1$-C$_4$-alkyl, and (C$_1$-C$_4$-alkoxy)$_2$P(=O)—, heterocyclyl-C$_1$-C$_4$-alkyl, wherein the heterocyclyl substituent is selected from the group consisting of 4- to 10-membered heterocycloalkyl, 5-membered heteroaryl, and 6-membered heteroaryl, each of which is optionally substituted by 1, 2 or 3 substituents independently selected from the group consisting of halogen, cyano, —OH, oxo, C$_1$-C$_4$-alkyl, C$_1$-C$_4$-halogenoalkyl having 1 to 5 halogen atoms, and C$_1$-C$_4$-alkoxy, phenyl, benzo-C$_5$-C$_6$-cycloalkyl, each of which is optionally substituted by 1, 2 or 3 substituents independently selected from the group consisting of halogen, cyano, C$_1$-C$_4$-alkyl, C$_1$-C$_4$-halogenoalkyl having 1 to 5 halogen atoms, C$_1$-C$_4$-alkoxy, and C$_1$-C$_4$-halogenoalkoxy having 1 to 5 halogen atoms, and a monocyclic or a bicyclic heterocycle selected from the group of 4- to 10-membered heterocycloalkyl, 5-membered heteroaryl, and 6-membered heteroaryl each of which is optionally substituted by 1, 2 or 3 substituents independently selected from the group consisting of halogen, —OH, oxo, cyano, C$_1$-C$_4$-alkyl, C$_1$-C$_4$-halogenoalkyl having 1 to 5 halogen atoms, C$_1$-C$_4$-alkoxy, and C$_1$-C$_4$-halogenoalkoxy having 1 to 5 halogen atoms, R$^{11}$ is selected from the group consisting of
C$_1$-C$_4$-alkyl, C$_3$-C$_6$-cycloalkyl, phenyl-C$_1$-C$_4$-alkyl, each of which is optionally substituted by 1, 2 or 3 substituents independently selected from the group consisting of halogen, —OH, C$_1$-C$_4$-alkyl, C$_1$-C$_4$-alkoxy, and C$_3$-C$_6$-cycloalkyl, and 4- to 10-membered heterocycloalkyl, R$^{12}$ is selected from the group consisting of
hydrogen,
C$_1$-C$_4$-alkyl, which is optionally substituted by 1, 2 or 3 substituents independently selected from the group consisting of —OH and —COOH, and a 6-membered heteroaryl, Q is a phenyl ring of formula (Q1)

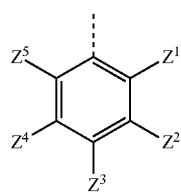

(Q1)

wherein
Z$^1$ is selected from the group consisting of hydrogen, halogen, C$_1$-C$_4$-alkyl, and C$_1$-C$_4$-alkoxy,
Z$^2$ is selected from the group consisting of hydrogen, halogen, —OH, C$_1$-C$_4$-alkyl, C$_1$-C$_4$-alkoxy, —NH(C$_1$-C$_4$-alkyl), —N(C$_1$-C$_4$-alkyl)$_2$, —NH(C$_3$-C$_6$-cycloalkyl), —N(C$_1$-C$_4$-alkyl)(C$_3$-C$_6$-cycloalkyl), C$_1$-C$_4$-halogenoalkyl having 1 to 5 halogen atoms, C$_1$-C$_4$-halogenoalkoxy having 1 to 5 halogen atoms, —S—(C$_1$-C$_4$-alkyl), and a 4- to 6-membered heterocycloalkyl, and
Z$^3$ is selected from the group consisting of hydrogen, halogen, C$_1$-C$_4$-alkyl, C$_1$-C$_4$-alkoxy, —NH(C$_1$-C$_4$-alkyl), and —N(C$_1$-C$_4$-alkyl)$_2$, Z$^4$ is selected from the group consisting of hydrogen, halogen, C$_1$-C$_4$-alkyl, and C$_1$-C$_4$-alkoxy,
Z$^5$ is selected from the group consisting of hydrogen, halogen, C$_1$-C$_4$-alkyl, and C$_1$-C$_4$-alkoxy, or a stereoisomer, a tautomer, an N-oxide, a hydrate, a solvate, or a salt thereof, or a mixture of any of the foregoing.

5. The compound according to claim 1, wherein:
A is selected from the group consisting of

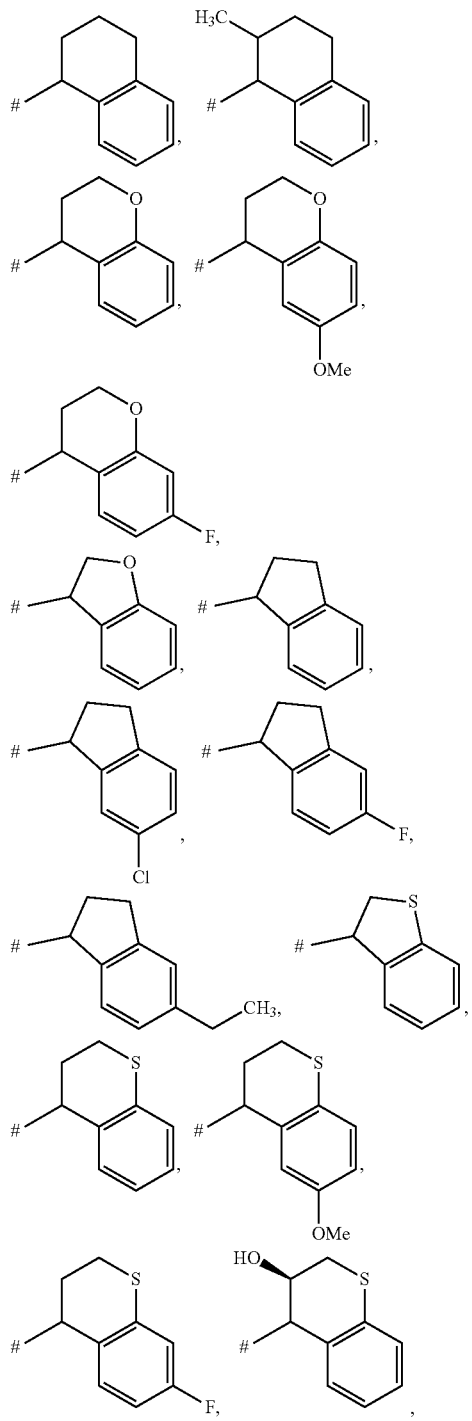

-continued

G is S,

R$^1$ is hydrogen or methyl,

R$^2$ is selected from the group consisting of hydrogen, chlorine, fluorine, —NR$^9$R$^{10}$, —OR$^{11}$, —SR$^{12}$, —S(O)R$^{12}$, —SO$_2$R$^{12}$, methyl, ethyl, propyl, isopropyl, cyclopropyl, cyclohexyl, propenyl, cyclopentenyl, cyclohexenyl, each of which is optionally substituted by 1 or 2 substituents independently selected from the group consisting of cyano, ethoxy-C(O)—, and —C(O)—NH$_2$; and a monocyclic or a bicyclic heterocycle selected from the group consisting of azetidine, pyrrolidine, pyrazolidine, imidazolidine, 1,2,4-triazolidine, piperidine, piperazine, tetrahydropyridine, dihydro-2H-pyrane, 1,2-oxazolidine, 1,2-oxazine, morpholine, thiomorpholine, 3,4-dihydroisoquinoline, 2,3-dihydro-indole, 1,3-dihydro-isoindoel, 3,9-dioxa-7-azabicyclo[3.3.1]nonane, 6-oxa-3-azabicyclo[3.1.1]heptane, 8-oxa-3-azabicyclo[3.2.1]octane, imidazole, pyrazole, 1,2,4-triazole, 1,2,3-triazole, 4-oxa-7-azaspiro[2.5]octane, each of which is optionally substituted by 1, 2, 3 or 4 substituents independently selected from the group consisting of fluorine, chlorine, cyano, —OH, oxo, —COOH, methoxy-C(O)—, ethoxy-C(O)—, tert-butoxy-C(O)—, —C(O)—NH$_2$, methyl, methyl-C(O)—, trifluoromethyl, hydroxymethyl-, methoxymethyl-, —NH$_2$, —NMe$_2$, and pyrrolidine, R$^3$ is selected from the group consisting of hydrogen, fluorine, chlorine, cyano, methyl, methoxy, and trifluoromethyl, R$^8$ is selected from the group consisting of hydrogen and methyl, R$^9$ and R$^{19}$ are independently selected from the group consisting of hydrogen, —NH(—C(O)-methyl), methoxy, methyl, ethyl, propyl, isopropyl, butyl, isobutyl, cyclopropyl, cyclobutyl, benzyl, 1-phenylethyl, each of which is optionally substituted by 1, 2 or 3 substituents independently selected from the group consisting of fluorine, —OH, —COOH, methoxy-C(O)—, ethoxy-C(O)—, tert-butoxy-C(O)—, —C(O)—NH$_2$, —C(O)—NMe$_2$, —NH—C(O)-methyl, methyl, methoxy, cyclopropyl, —NH$_2$, NMe$_2$, S-methyl, S(O)-methyl, SO$_2$-methyl, and (EtO)$_2$P(═O)—, heterocyclyl-methyl, heterocyclyl-ethyl, wherein the heterocyclyl substituent is selected from the group consisting of pyrrolidine, morpholine, pyrazole, 1,2,4-oxadiazole, pyridine, each of which is optionally substituted by 1 substituent independently selected from the group consisting of fluorine, chlorine, —OH, oxo, and methyl, phenyl, 2,3-dihydro-1H-indene, and a monocyclic or a bicyclic heterocycle selected from the group of oxetane, thietane, pyrrolidine, morpholine, tetrahydropyrane, pyridine, and pyrazole, each of which is optionally substituted by 1 or 2 substituents independently selected from the group consisting of fluorine, chlorine, —OH, oxo, and methyl;

R$^{11}$ is selected from the group consisting of methyl, ethyl, isopropyl, butyl, cyclopentyl, benzyl, each of which is optionally substituted by 1 or 2 substituents independently selected from the group consisting of fluorine, —OH, methyl, methoxy, and cyclopentyl; and a monocyclic or a bicyclic heterocycle selected from the group consisting of pyrrolidin and tetrahydropyran, R$^{12}$ is selected from the group consisting of methyl, ethyl, each of which is optionally substituted by 1 substituent independently selected from the group consisting of —OH and —COOH; and pyridine, Q is a phenyl ring of formula (Q1)

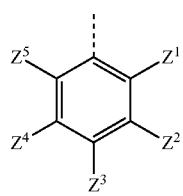

(Q1)

wherein

Z$^1$ is selected from the group consisting of hydrogen, fluorine, chlorine, methyl, and methoxy, Z$^2$ is selected from the group consisting of hydrogen, fluorine, chlorine, —OH, methyl, ethyl, methoxy, ethoxy, —NH(CH$_3$), —N(CH$_3$)$_2$, trifluoromethyl, and trifluoromethoxy, $Z^3$ is selected from the group consisting of hydrogen, fluorine, chlorine, methyl, methoxy, —NH(CH$_3$), and —N(CH$_3$)$_2$, $Z^4$ is selected from the group consisting of hydrogen, fluorine, chlorine, methyl, and methoxy, $Z^5$ is selected from the group consisting of hydrogen, fluorine, chlorine methyl, and methoxy, or a stereoisomer, a tautomer, an N-oxide, a hydrate, a solvate, or a salt thereof, or a mixture of any of the foregoing.

6. The compound according to claim 1, wherein:

A is selected from the group consisting of

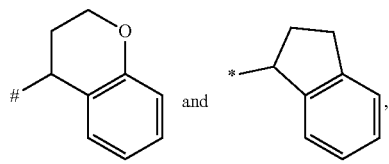

G is S, $R^1$ is hydrogen or methyl, $R^2$ is selected from the group consisting of hydrogen, chlorine, fluorine, —NH$_2$, —NH(CH$_3$), —N(CH$_3$)$_2$, methoxy, ethoxy, methyl, ethyl, propyl, isopropyl, cyclopropyl, trifluoromethyl, and trifluoromethoxy, $R^3$ is selected from the group consisting of hydrogen, chlorine, fluorine, methyl, methoxy, and trifluoromethyl, Q is a phenyl ring of formula (Q1)

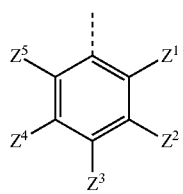

(Q1)

wherein $Z^1$ is selected from the group consisting of hydrogen, fluorine, chlorine, methyl, and methoxy, $Z^2$ is selected from the group consisting of hydrogen, fluorine, chlorine, —OH, methyl, ethyl, methoxy, ethoxy, —NH(CH$_3$), —N(CH$_3$)$_2$, trifluoromethyl, and trifluoromethoxy, $Z^3$ is selected from the group consisting of hydrogen, fluorine, chlorine, methyl, methoxy, —NH(CH$_3$), and —N(CH$_3$)$_2$, $Z^4$ is selected from the group consisting of hydrogen, fluorine, chlorine, methyl, and methoxy, $Z^5$ is selected from the group consisting of hydrogen, fluorine, chlorine, methyl, and methoxy, or a stereoisomer, a tautomer, an N-oxide, a hydrate, a solvate, or a salt thereof, or a mixture of any of the foregoing.

7. A compound of formula (II):

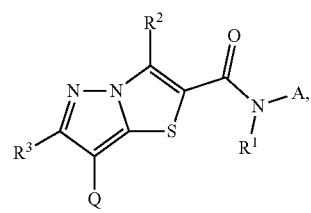

(II)

wherein

A is selected from the group consisting of

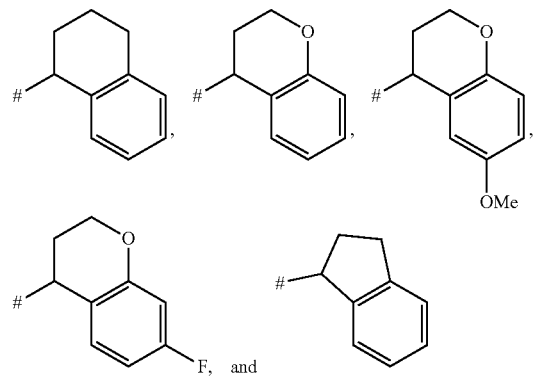

$R^1$ is hydrogen or methyl, $R^2$ is selected from the group consisting of hydrogen, chlorine, fluorine, methoxy, methyl, ethyl, propyl, isopropyl, trifluoromethyl, and trifluoromethoxy, $R^3$ is selected from the group consisting of hydrogen, chlorine, fluorine, methyl, methoxy, and trifluoromethyl, Q is a phenyl ring of formula (Q1)

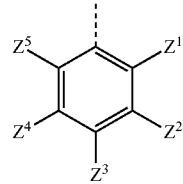

(Q1)

wherein $Z^1$ is selected from the group consisting of hydrogen and halogen, $Z^2$ is selected from the group consisting of hydrogen, halogen, —N(C$_1$-C$_4$-alkyl)$_2$, —C$_1$-C$_4$-halogenoalkyl having 1 to 5 halogen atoms, and C$_1$-C$_4$-halogenoalkoxy having 1 to 5 halogen atoms, $Z^3$ is selected from the group consisting of hydrogen and halogen, $Z^4$ is selected from the group consisting of hydrogen and halogen, $Z^5$ is selected from the group consisting of hydrogen and halogen, or a stereoisomer, a tautomer, an N-oxide, a hydrate, a solvate, or a salt thereof, or a mixture of any of the foregoing.

8. The compound according to claim 7, wherein A is selected from the group consisting of

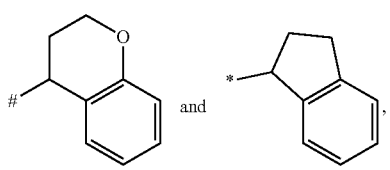

R¹ is hydrogen,
R² is isopropyl,
R³ is methyl,
Q is a phenyl ring of formula (Q1)

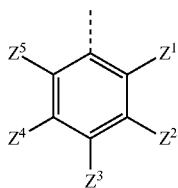

wherein
$Z^1$, $Z^3$, $Z^4$ and $Z^5$ are independently selected from the group consisting of hydrogen, fluorine, and chlorine, and
$Z^2$ is selected from the group consisting of hydrogen, fluorine, chlorine, —N(CH₃)₂, trifluoromethyl, and trifluoromethoxy,
or a stereoisomer, a tautomer, an N-oxide, a hydrate, a solvate, or a salt thereof, or a mixture of any of the foregoing.

9. A pharmaceutical composition comprising a compound of formula (I) according to claim 1, or a stereoisomer, a tautomer, an N-oxide, a hydrate, a solvate, or a salt thereof, or a mixture of any of the foregoing, and one or more pharmaceutically acceptable excipients.

10. A method for controlling helminth infections in humans and/or animals comprising administering an anthelminthically effective amount of at least one compound of formula (I) according to claim 1, or a stereoisomer, a tautomer, an N-oxide, a hydrate, a solvate, or a salt thereof, or a mixture of any of the foregoing, to a human or an animal in need thereof.

11. A pharmaceutical composition comprising a compound of formula (II) according to claim 7, or a stereoisomer, a tautomer, an N-oxide, a hydrate, a solvate, or a salt thereof, or a mixture of any of the foregoing, and one or more pharmaceutically acceptable excipients.

12. A method for controlling helminth infections in humans and/or animals comprising administering an anthelminthically effective amount of at least one compound of formula (II) according to claim 7, or a stereoisomer, a tautomer, an N-oxide, a hydrate, a solvate, or a salt thereof, or a mixture of any of the foregoing, to a human or an animal in need thereof.

13. A compound of formula (I)

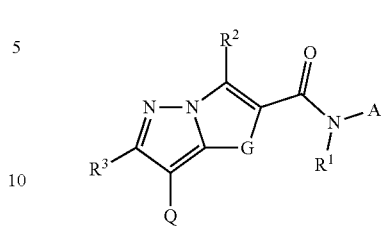

(I)

wherein
(a) G is S, R¹ is H, R² is isopropyl, R³ is methyl, Q is 3,5-dichlorophenyl, and A is (4S)-3,4-dihydro-2H-chromen-4-yl,
(b) G is S, R¹ is H, R² is isopropyl, R³ is methyl, Q is 2,3-dichlorophenyl, and A is (4S)-3,4-dihydro-2H-chromen-4-yl,
(c) G is S, R¹ is H, R² is isopropyl, R³ is methyl, Q is 2-fluoro-3-(trifluoromethyl)-phenyl, and A is (4S)-3,4-dihydro-2H-chromen-4-yl,
(d) G is S, R¹ is H, R² is isopropyl, R³ is methyl, Q is 2-fluoro-3-(trifluoromethoxy)-phenyl, and A is (4S)-3,4-dihydro-2H-chromen-4-yl,
(e) G is S, R¹ is H, R² is isopropyl, R³ is methyl, Q is 3,5-dichloro-4-fluorophenyl, and A is (4S)-3,4-dihydro-2H-chromen-4-yl,
(f) G is S, R¹ is H, R² is isopropyl, R³ is methyl, Q is 2,4-difluoro-3-(dimethylamino)-phenyl, and A is (4S)-3,4-dihydro-2H-chromen-4-yl,
(g) G is S, R¹ is H, R² is isopropyl, R³ is methyl, Q is 3,4-dichlorophenyl, and A is (4S)-3,4-dihydro-2H-chromen-4-yl,
(h) G is S, R¹ is H, R² is isopropyl, R³ is methyl, Q is 3,4-difluorophenyl, and A is (4S)-3,4-dihydro-2H-chromen-4-yl,
(i) G is S, R¹ is H, R² is isopropyl, R³ is methyl, Q is 2,3,4-trifluorophenyl, and A is (4S)-3,4-dihydro-2H-chromen-4-yl,
(j) G is S, R¹ is H, R² is isopropyl, R³ is methyl, Q is 2,6-dichlorophenyl, and A is (4S)-3,4-dihydro-2H-chromen-4-yl,
(k) G is S, R¹ is H, R² is isopropyl, R³ is methyl, Q is 2-chloro-3-(trifluoromethyl)-phenyl, and A is (4S)-3,4-dihydro-2H-chromen-4-yl,
(l) G is S, R¹ is H, R² is isopropyl, R³ is methyl, Q is 2,3,5-trifluorophenyl, and A is (4S)-3,4-dihydro-2H-chromen-4-yl,
(m) G is S, R¹ is H, R² is isopropyl, R³ is methyl, Q is 2-fluoro-3-(dimethylamino)-phenyl, and A is (4S)-3,4-dihydro-2H-chromen-4-yl,
(n) G is S, R¹ is H, R² is isopropyl, R³ is methyl, Q is 3,5-dichloro-4-fluorophenyl, and A is (1S)-2,3-dihydro-1H-inden-1-yl, and
(o) G is S, R¹ is H, R² is isopropyl, R³ is methyl, Q is 2,3-dichlorophenyl, and A is (1S)-2,3-dihydro-1H-inden-1-yl.

* * * * *